United States Patent
Popp et al.

(10) Patent No.: US 11,129,713 B2
(45) Date of Patent: Sep. 28, 2021

(54) PROSTHETIC HEART VALVE DELIVERY APPARATUS

(71) Applicant: Edwards Lifesciences Corporation, Irvine, CA (US)

(72) Inventors: Michael J. Popp, Irvine, CA (US); David Alon, Zichron Yaacov (IL); Jun Liu, Corona, CA (US); Luca Pesce, Huntington Beach, CA (US); Mohammad Jafari, Foothill Ranch, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 17/077,860

(22) Filed: Oct. 22, 2020

(65) Prior Publication Data

US 2021/0038385 A1 Feb. 11, 2021

Related U.S. Application Data

(63) Continuation of application No. 16/783,005, filed on Feb. 5, 2020, which is a continuation of application
(Continued)

(51) Int. Cl.
*A61F 2/24* (2006.01)
*A61F 2/00* (2006.01)
(Continued)

(52) U.S. Cl.
CPC .......... *A61F 2/2427* (2013.01); *A61F 2/0095* (2013.01); *A61F 2/2418* (2013.01);
(Continued)

(58) Field of Classification Search
None
See application file for complete search history.

(56) References Cited

U.S. PATENT DOCUMENTS

| 519,297 A | 5/1894 | Bauer |
| 3,409,013 A | 11/1968 | Berry |

(Continued)

FOREIGN PATENT DOCUMENTS

| CA | 2363099 A1 | 8/2000 |
| CA | 2767527 A1 | 1/2011 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Shaun L David
(74) *Attorney, Agent, or Firm* — Edwards Lifesciences; Sandon M. Duncan

(57) ABSTRACT

A prosthetic heart valve delivery system can include a catheter portion having a sheath that can cover and uncover the prosthetic heart valve mounted on an inner shaft, a handle having a sheath actuator operatively coupled to a proximal portion of the sheath, the inner shaft extending through the handle, and a shaft retractor releasably coupled to a proximal portion of the handle and fixedly coupled to a proximal portion of the inner shaft. A sheath actuator can move the sheath axially relative to the inner shaft when the shaft retractor is coupled to the handle, and a proximal movement of the sheath relative to the inner shaft can cause the sheath to uncover the prosthetic heart valve. The shaft retractor can be operable to retract the inner shaft and the nosecone proximally relative to the sheath when the shaft retractor is released from the handle.

18 Claims, 46 Drawing Sheets

Related U.S. Application Data

No. 16/353,905, filed on Mar. 14, 2019, which is a continuation of application No. 14/794,690, filed on Jul. 8, 2015, now Pat. No. 10,561,494, which is a continuation of application No. 13/405,119, filed on Feb. 24, 2012, now Pat. No. 9,155,619.

(60) Provisional application No. 61/446,972, filed on Feb. 25, 2011.

(51) Int. Cl.
*A61F 2/966* (2013.01)
*A61F 2/95* (2013.01)
*A61M 25/00* (2006.01)
*A61F 2/915* (2013.01)

(52) U.S. Cl.
CPC .......... *A61F 2/2436* (2013.01); *A61F 2/9517* (2020.05); *A61F 2/9522* (2020.05); *A61F 2002/9155* (2013.01); *A61F 2002/9665* (2013.01); *A61F 2220/005* (2013.01); *A61F 2220/0058* (2013.01); *A61F 2220/0075* (2013.01); *A61F 2230/0054* (2013.01); *A61F 2230/0069* (2013.01); *A61M 25/0051* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,955,895 A | 9/1990 | Sugiyama et al. |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,176,698 A | 1/1993 | Burns et al. |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,325,845 A | 7/1994 | Adair |
| 5,332,402 A | 7/1994 | Teitelbaum |
| 5,358,496 A | 10/1994 | Ortiz et al. |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,599,305 A | 2/1997 | Hermann et al. |
| 5,607,464 A | 3/1997 | Trescony et al. |
| 5,609,626 A | 3/1997 | Quijano et al. |
| 5,628,792 A | 5/1997 | Lentell |
| 5,632,760 A | 5/1997 | Sheiban et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,782,809 A | 7/1998 | Umeno et al. |
| 5,800,508 A | 9/1998 | Goicoechea et al. |
| 5,824,044 A | 10/1998 | Quiachon et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,908,405 A | 6/1999 | Imran et al. |
| 5,916,147 A | 6/1999 | Boury |
| 5,925,063 A | 7/1999 | Khosravi |
| 5,957,949 A | 9/1999 | Leonhardt et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,027,525 A | 2/2000 | Suh et al. |
| 6,033,381 A | 3/2000 | Kontos |
| 6,040,416 A | 3/2000 | Sekharipuram et al. |
| 6,132,473 A | 10/2000 | Williams et al. |
| 6,143,016 A | 11/2000 | Bleam et al. |
| 6,162,208 A | 12/2000 | Hipps |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |

(56) References Cited

U.S. PATENT DOCUMENTS

| | | |
|---|---|---|
| 6,231,602 B1 | 5/2001 | Carpentier et al. |
| 6,235,050 B1 | 5/2001 | Quiachon et al. |
| 6,245,102 B1 | 6/2001 | Jayaraman |
| 6,251,092 B1 | 6/2001 | Qin et al. |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,379,372 B1 | 4/2002 | Dehdashtian et al. |
| 6,383,171 B1 | 5/2002 | Gifford et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,471,672 B1 | 10/2002 | Brown et al. |
| 6,482,228 B1 | 11/2002 | Norred |
| 6,488,704 B1 | 12/2002 | Connelly et al. |
| 6,500,147 B2 | 12/2002 | Omaleki et al. |
| 6,514,228 B1 | 2/2003 | Hamilton et al. |
| 6,527,979 B2 | 3/2003 | Constantz |
| 6,569,196 B1 | 5/2003 | Vesely |
| 6,579,305 B1 | 6/2003 | Lashinski |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,096,554 B2 | 8/2006 | Austin et al. |
| 7,137,993 B2 | 11/2006 | Acosta et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,579,381 B2 | 8/2009 | Dove |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,618,447 B2 | 11/2009 | Case et al. |
| 7,655,034 B2 | 2/2010 | Mitchell et al. |
| 7,712,606 B2 | 5/2010 | Salahieh et al. |
| 7,749,266 B2 | 7/2010 | Forster et al. |
| 7,780,723 B2 | 8/2010 | Taylor |
| 7,780,726 B2 | 8/2010 | Seguin |
| 7,785,366 B2 | 8/2010 | Maurer et al. |
| 7,914,569 B2 | 3/2011 | Nguyen et al. |
| 7,959,661 B2 | 6/2011 | Hijlkema et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,007,992 B2 | 8/2011 | Tian et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang |
| 8,182,530 B2 | 5/2012 | Huber |
| 8,291,570 B2 | 10/2012 | Eidenschink et al. |
| RE43,882 E | 12/2012 | Hopkins et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,475,523 B2 | 7/2013 | Duffy |
| 8,568,472 B2 | 10/2013 | Marchand et al. |
| 8,652,145 B2 | 2/2014 | Maimon et al. |
| 8,652,203 B2 | 2/2014 | Quadri et al. |
| 8,747,463 B2 | 6/2014 | Fogarty et al. |
| 8,801,776 B2 | 8/2014 | House et al. |
| 9,061,119 B2 | 6/2015 | Le et al. |
| 9,078,781 B2 | 7/2015 | Ryan et al. |
| 9,119,716 B2 | 9/2015 | Lee et al. |
| 9,155,619 B2 | 10/2015 | Liu et al. |
| 9,168,131 B2 | 10/2015 | Yohanan et al. |
| 9,216,082 B2 | 12/2015 | Von Segesser et al. |
| 9,795,477 B2 | 10/2017 | Tran et al. |
| 9,867,700 B2 | 1/2018 | Bakis et al. |
| 2001/0002445 A1 | 5/2001 | Vesely |
| 2001/0007082 A1 | 7/2001 | Dusbabek et al. |
| 2001/0021872 A1 | 9/2001 | Bailey et al. |
| 2001/0023372 A1 | 9/2001 | Chen et al. |
| 2002/0016624 A1 | 2/2002 | Patterson et al. |
| 2002/0026094 A1 | 2/2002 | Roth |
| 2002/0032481 A1 | 3/2002 | Gabbay |
| 2002/0058995 A1 | 5/2002 | Stevens |
| 2002/0138135 A1 | 9/2002 | Duerig et al. |
| 2002/0143390 A1 | 10/2002 | Ishii |
| 2002/0161377 A1 | 10/2002 | Rabkin |
| 2002/0165461 A1 | 11/2002 | Hayzelden et al. |
| 2002/0173842 A1 | 11/2002 | Buchanan |
| 2003/0014105 A1 | 1/2003 | Cao |
| 2003/0040792 A1 | 2/2003 | Gabbay |
| 2003/0050694 A1 | 3/2003 | Yang et al. |
| 2003/0100939 A1 | 5/2003 | Yodfat et al. |
| 2003/0120341 A1 | 6/2003 | Shennib et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0236411 A1 | 11/2004 | Sarac et al. |
| 2004/0260389 A1 | 12/2004 | Case et al. |
| 2005/0010285 A1 | 1/2005 | Lambrecht et al. |
| 2005/0027305 A1 | 2/2005 | Shiu et al. |
| 2005/0075725 A1 | 4/2005 | Rowe |
| 2005/0075728 A1 | 4/2005 | Nguyen et al. |
| 2005/0075731 A1 | 4/2005 | Artof et al. |
| 2005/0080474 A1 | 4/2005 | Andreas et al. |
| 2005/0096736 A1 | 5/2005 | Osse et al. |
| 2005/0096738 A1 | 5/2005 | Cali et al. |
| 2005/0113910 A1 | 5/2005 | Paniagua et al. |
| 2005/0137688 A1 | 6/2005 | Salahieh et al. |
| 2005/0137689 A1 | 6/2005 | Salahieh et al. |
| 2005/0137693 A1 | 6/2005 | Haug et al. |
| 2005/0137697 A1 | 6/2005 | Salahieh et al. |
| 2005/0149159 A1 | 7/2005 | Andreas et al. |
| 2005/0149160 A1 | 7/2005 | McFerran |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0245894 A1 | 11/2005 | Zadno-Azizi |
| 2005/0288766 A1 | 12/2005 | Plain et al. |

(56) References Cited

U.S. PATENT DOCUMENTS

| | | |
|---|---|---|
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0149360 A1 | 7/2006 | Schwammenthal et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0276813 A1 | 12/2006 | Greenberg |
| 2006/0282150 A1 | 12/2006 | Olson et al. |
| 2006/0287717 A1 | 12/2006 | Rowe et al. |
| 2006/0287719 A1 | 12/2006 | Rowe et al. |
| 2007/0005131 A1 | 1/2007 | Taylor |
| 2007/0005231 A1 | 1/2007 | Seguchi |
| 2007/0010876 A1 | 1/2007 | Salahieh et al. |
| 2007/0010877 A1 | 1/2007 | Salahieh et al. |
| 2007/0061008 A1 | 3/2007 | Salahieh et al. |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0219612 A1 | 9/2007 | Andreas et al. |
| 2007/0233228 A1 | 10/2007 | Eberhardt et al. |
| 2007/0239254 A1 | 10/2007 | Chia et al. |
| 2007/0244546 A1 | 10/2007 | Francis |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0065011 A1* | 3/2008 | Marchand ......... A61M 25/0662 604/103.02 |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294230 A1 | 11/2008 | Parker |
| 2008/0294248 A1 | 11/2008 | Yang et al. |
| 2008/0319526 A1 | 12/2008 | Hill et al. |
| 2009/0024428 A1 | 1/2009 | Hudock, Jr. |
| 2009/0069889 A1 | 3/2009 | Suri et al. |
| 2009/0099638 A1 | 4/2009 | Grewe |
| 2009/0118826 A1 | 5/2009 | Khaghani |
| 2009/0125118 A1 | 5/2009 | Gong |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1* | 11/2009 | Le ..................... A61F 2/2433 623/2.11 |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0299456 A1 | 12/2009 | Melsheimer |
| 2009/0319037 A1 | 12/2009 | Rowe et al. |
| 2010/0023372 A1 | 1/2010 | Gonzalez |
| 2010/0030318 A1 | 2/2010 | Berra |
| 2010/0036472 A1 | 2/2010 | Papp |
| 2010/0036473 A1 | 2/2010 | Roth |
| 2010/0036484 A1 | 2/2010 | Hariton et al. |
| 2010/0049313 A1 | 2/2010 | Alon et al. |
| 2010/0057185 A1 | 3/2010 | Melsheimer et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0121425 A1 | 5/2010 | Shimada |
| 2010/0121434 A1 | 5/2010 | Paul et al. |
| 2010/0145431 A1 | 6/2010 | Wu et al. |
| 2010/0161036 A1 | 6/2010 | Pintor et al. |
| 2010/0168844 A1 | 7/2010 | Toomes et al. |
| 2010/0174363 A1 | 7/2010 | Castro |
| 2010/0185277 A1 | 7/2010 | Braido et al. |
| 2010/0191326 A1 | 7/2010 | Alkhatib |
| 2010/0198347 A1 | 8/2010 | Zakay et al. |
| 2010/0204781 A1 | 8/2010 | Alkhatib |
| 2010/0256749 A1 | 10/2010 | Tran et al. |
| 2010/0274227 A1 | 10/2010 | Khairkhahan et al. |
| 2010/0274344 A1 | 10/2010 | Dusbabek et al. |
| 2011/0004299 A1 | 1/2011 | Essinger et al. |
| 2011/0015729 A1 | 1/2011 | Jimenez et al. |
| 2011/0040374 A1 | 2/2011 | Goetz et al. |
| 2011/0046712 A1 | 2/2011 | Melsheimer et al. |
| 2011/0054596 A1 | 3/2011 | Taylor |
| 2011/0066224 A1 | 3/2011 | White |
| 2011/0137331 A1 | 6/2011 | Walsh et al. |
| 2011/0137397 A1 | 6/2011 | Chau et al. |
| 2011/0160846 A1 | 6/2011 | Bishop et al. |
| 2011/0218619 A1 | 9/2011 | Benichou et al. |
| 2011/0295354 A1* | 12/2011 | Bueche ................ A61F 2/966 623/1.11 |
| 2011/0301700 A1 | 12/2011 | Fish et al. |
| 2011/0301702 A1* | 12/2011 | Rust .................. A61F 2/2436 623/2.11 |
| 2011/0301703 A1 | 12/2011 | Glazier |
| 2011/0307048 A1* | 12/2011 | Ivancev ............... A61F 2/95 623/1.11 |
| 2011/0307049 A1* | 12/2011 | Kao .................... A61F 2/966 623/1.11 |
| 2011/0319991 A1 | 12/2011 | Hariton et al. |
| 2012/0041547 A1* | 2/2012 | Duffy ................ A61F 2/2436 623/2.11 |
| 2012/0071969 A1 | 3/2012 | Li et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0239142 A1 | 9/2012 | Liu et al. |
| 2012/0259409 A1 | 10/2012 | Nguyen et al. |
| 2012/0265296 A1 | 10/2012 | McNamara et al. |
| 2012/0290078 A1 | 11/2012 | Bourang et al. |
| 2012/0316642 A1 | 12/2012 | Yu et al. |
| 2013/0013047 A1* | 1/2013 | Ramos ................ A61F 2/966 623/1.11 |
| 2013/0023985 A1 | 1/2013 | Khairkhahan et al. |
| 2013/0030519 A1 | 1/2013 | Tran et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0172978 A1 | 7/2013 | Vidlund et al. |
| 2013/0178930 A1* | 7/2013 | Straubinger ........... A61F 2/966 623/2.1 |
| 2013/0190857 A1 | 7/2013 | Mitra et al. |
| 2013/0190861 A1* | 7/2013 | Chau ................ A61F 2/2418 623/2.18 |
| 2013/0211508 A1 | 8/2013 | Lane et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0046433 A1 | 2/2014 | Kovalsky |
| 2014/0052237 A1 | 2/2014 | Lane et al. |
| 2014/0194981 A1 | 7/2014 | Menk et al. |
| 2014/0194982 A1 | 7/2014 | Kovalsky et al. |
| 2014/0200661 A1 | 7/2014 | Pintor et al. |
| 2014/0209238 A1 | 7/2014 | Bonyuet et al. |
| 2014/0214159 A1 | 7/2014 | Vidlund et al. |
| 2014/0222136 A1 | 8/2014 | Geist et al. |
| 2014/0243965 A1 | 8/2014 | Benson et al. |
| 2014/0277417 A1 | 9/2014 | Schraut et al. |
| 2014/0277419 A1 | 9/2014 | Garde et al. |

(56) References Cited

U.S. PATENT DOCUMENTS

| | | |
|---|---|---|
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2015/0297381 A1 | 10/2015 | Essinger et al. |
| 2017/0014229 A1 | 1/2017 | Nguyen-Thien-Nhon et al. |
| 2017/0056149 A1 | 3/2017 | Rajpara et al. |
| 2017/0065415 A1 | 3/2017 | Rupp et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0258584 A1 | 9/2017 | Chang et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | | |
|---|---|---|---|
| CN | 101291637 A | | 10/2008 |
| CN | 101309654 A | | 11/2008 |
| CN | 101641061 A | | 2/2010 |
| DE | 0144167 C | | 9/1903 |
| DE | 2246526 A1 | | 3/1973 |
| DE | 19532846 A1 | | 3/1997 |
| DE | 19546692 A1 | | 6/1997 |
| DE | 19857887 A1 | | 7/2000 |
| DE | 19907646 A1 | | 8/2000 |
| DE | 10049812 A1 | | 4/2002 |
| DE | 10049813 C1 | | 4/2002 |
| DE | 10049814 A1 | | 4/2002 |
| DE | 10049815 A1 | | 4/2002 |
| EP | 0103546 A1 | | 3/1984 |
| EP | 0592410 B1 | | 10/1995 |
| EP | 0850607 A1 | | 7/1998 |
| EP | 1057460 A1 | | 12/2000 |
| EP | 1088529 A2 | | 4/2001 |
| EP | 1570809 A1 | | 9/2005 |
| EP | 1796597 A2 | | 6/2007 |
| EP | 2218403 A1 | | 8/2010 |
| FR | 2788217 A1 | | 7/2000 |
| FR | 2815844 A1 | | 5/2002 |
| GB | 2056023 A | | 3/1981 |
| SU | 1271508 A1 | | 11/1986 |
| WO | 9117720 A1 | | 11/1991 |
| WO | 9217118 A1 | | 10/1992 |
| WO | 9301768 A1 | | 2/1993 |
| WO | 9724080 A1 | | 7/1997 |
| WO | 9829057 A1 | | 7/1998 |
| WO | 9912483 A1 | | 3/1999 |
| WO | 9930646 A1 | | 6/1999 |
| WO | 9933414 A1 | | 7/1999 |
| WO | 0018333 A1 | | 4/2000 |
| WO | 0041652 A1 | | 7/2000 |
| WO | 0135878 A2 | | 5/2001 |
| WO | 0149213 A2 | | 7/2001 |
| WO | 0154624 A1 | | 8/2001 |
| WO | 0154625 A1 | | 8/2001 |
| WO | 0162189 A1 | | 8/2001 |
| WO | 0047139 A9 | | 9/2001 |
| WO | 0164137 A1 | | 9/2001 |
| WO | 0176510 A2 | | 10/2001 |
| WO | 0222054 A1 | | 3/2002 |
| WO | 0236048 A1 | | 5/2002 |
| WO | 0241789 A2 | | 5/2002 |
| WO | 0243620 A1 | | 6/2002 |
| WO | 0247575 A2 | | 6/2002 |
| WO | 0249540 A2 | | 6/2002 |
| WO | 02060352 | | 8/2002 |
| WO | 03030776 A2 | | 4/2003 |
| WO | 33047468 A1 | | 6/2003 |
| WO | 2004019825 A1 | | 3/2004 |
| WO | 2005034812 A1 | | 4/2005 |
| WO | 2005055883 A1 | | 6/2005 |
| WO | 2005084595 A1 | | 9/2005 |
| WO | 2006014233 A2 | | 2/2006 |
| WO | 2006032051 A2 | | 3/2006 |
| WO | 2006034008 A2 | | 3/2006 |
| WO | 2006111391 A1 | | 10/2006 |
| WO | 2006127089 A1 | | 11/2006 |
| WO | 2006138173 A2 | | 12/2006 |
| WO | 2007033093 A2 | | 3/2007 |
| WO | 2005102015 A3 | | 4/2007 |
| WO | 2007047488 A2 | | 4/2007 |
| WO | 2007067942 A1 | | 6/2007 |
| WO | 2007097983 A2 | | 8/2007 |
| WO | 2008005405 A2 | | 1/2008 |
| WO | 2008015257 A2 | | 2/2008 |
| WO | 2008031103 A2 | | 3/2008 |
| WO | 2008035337 A2 | | 3/2008 |
| WO | 2008091515 A2 | | 7/2008 |
| WO | 2008124844 A1 | | 10/2008 |
| WO | 2008147964 A1 | | 12/2008 |
| WO | 2008150529 A1 | | 12/2008 |
| WO | 2009033469 A1 | | 3/2009 |
| WO | 2009042196 A2 | | 4/2009 |
| WO | 2009053497 A1 | | 4/2009 |
| WO | 2009061389 A2 | | 5/2009 |
| WO | 2009116041 A2 | | 9/2009 |
| WO | 2009149462 A2 | | 12/2009 |
| WO | 2010011699 A2 | | 1/2010 |
| WO | 2010022138 A2 | | 2/2010 |
| WO | 2010121076 A2 | | 10/2010 |
| WO | 2013106585 A1 | | 7/2013 |
| WO | 2015085218 A1 | | 6/2015 |

OTHER PUBLICATIONS

Bailey, S. "Percutaneous Expandable Prosthetic Valves," Textbook of Interventional Cardiology vol. 2, 2nd Ed. pp. 1268-1276. 1994.
H.R. Andersen "History of Percutaneous Aortic Valve Prosthesis," Herz No. 34. pp. 343-346. 2009.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Uchida, "Modifications of Gianturco Expandable Wire Stents," American Journal of Roentgenology, vol. 150. pp. 1185-1187 1986.
Wheatley, "Valve Prostheses," Operative Surgery, 4th ed. pp. 415-424. 1986.

\* cited by examiner

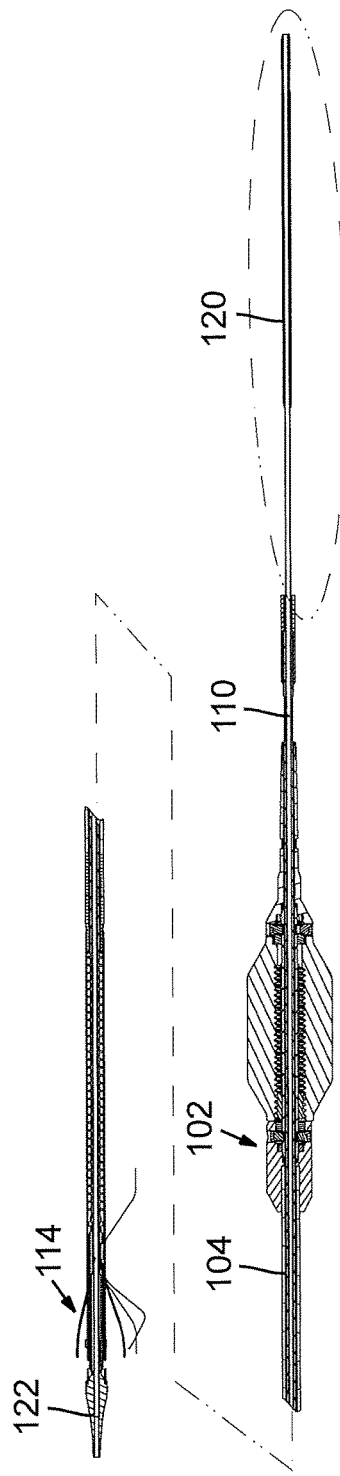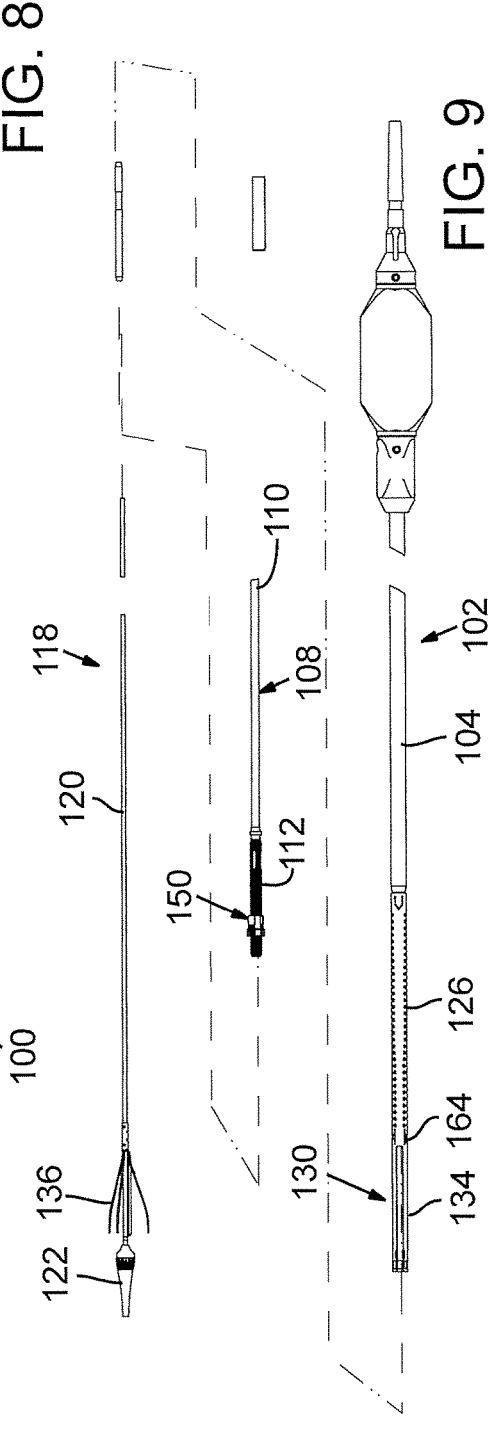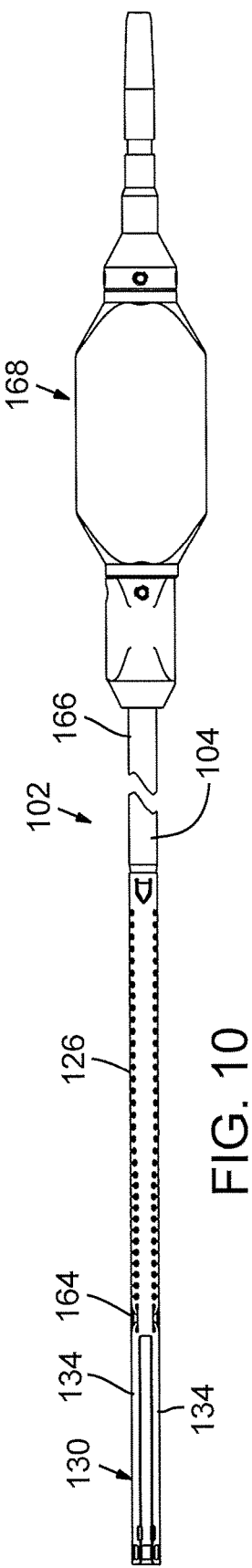

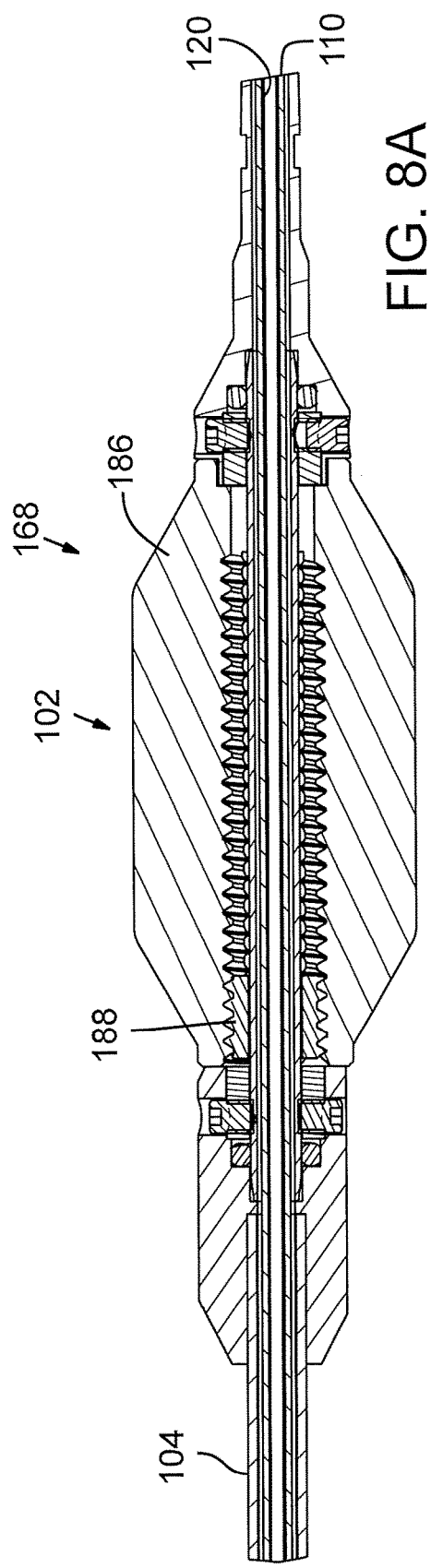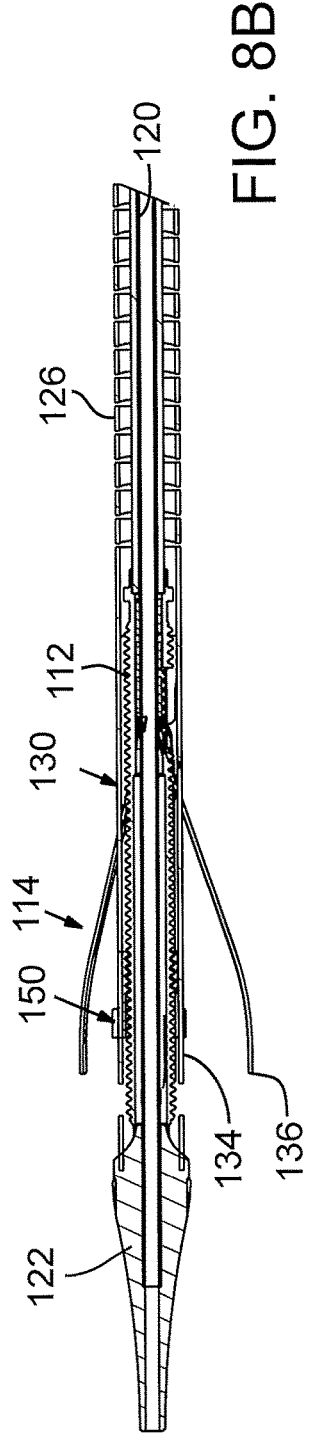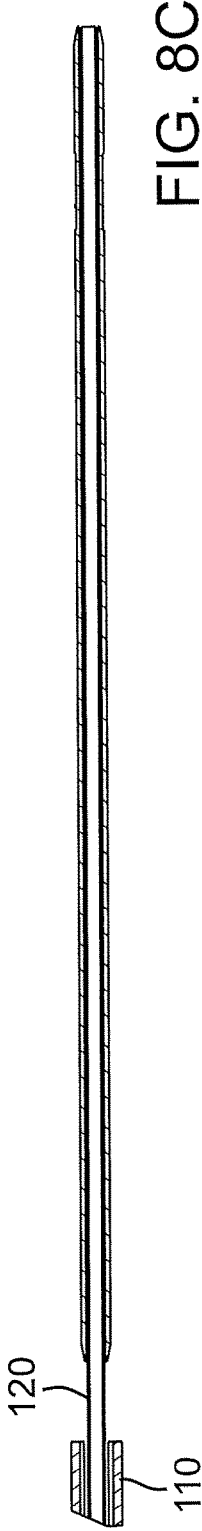

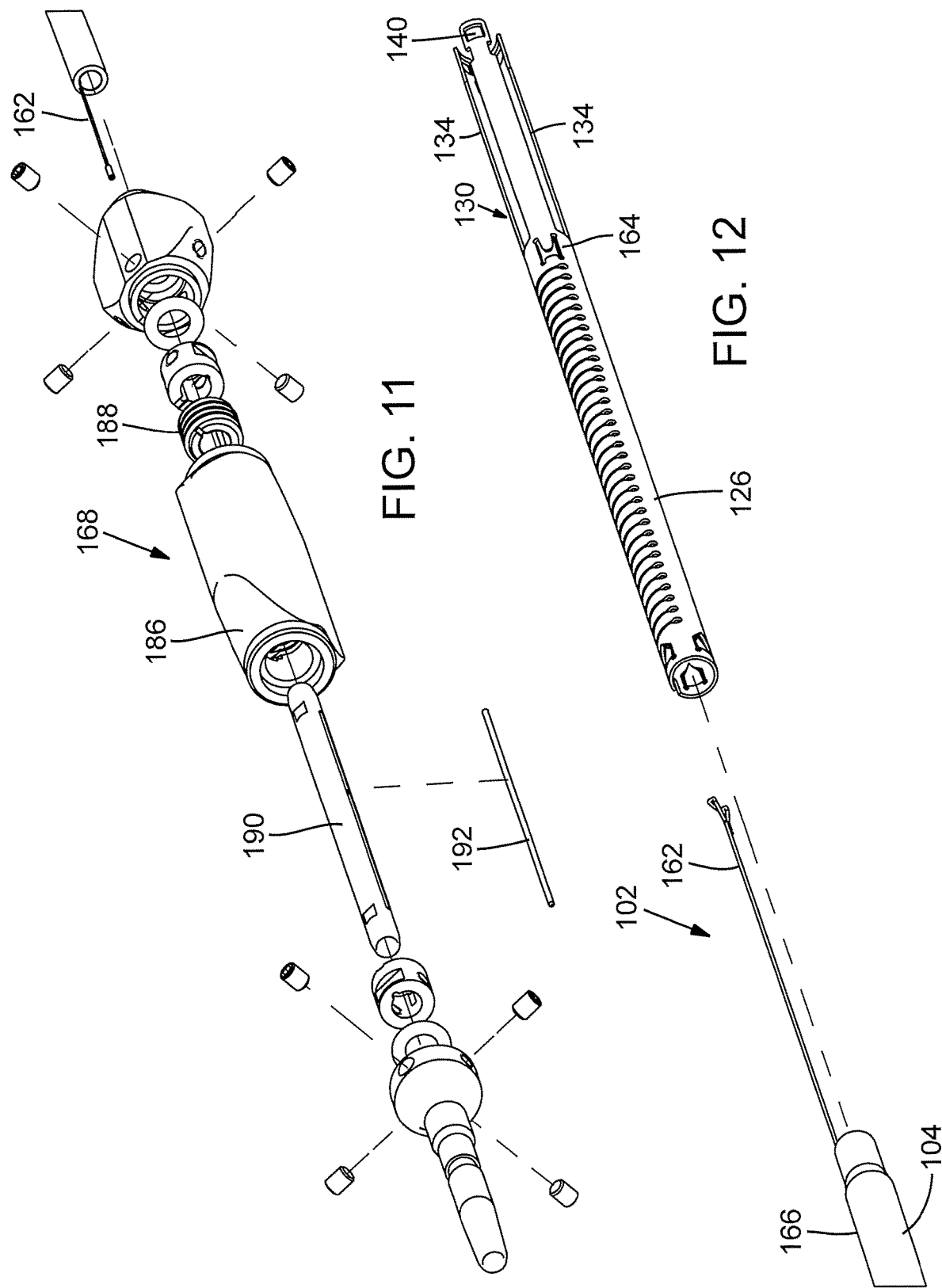

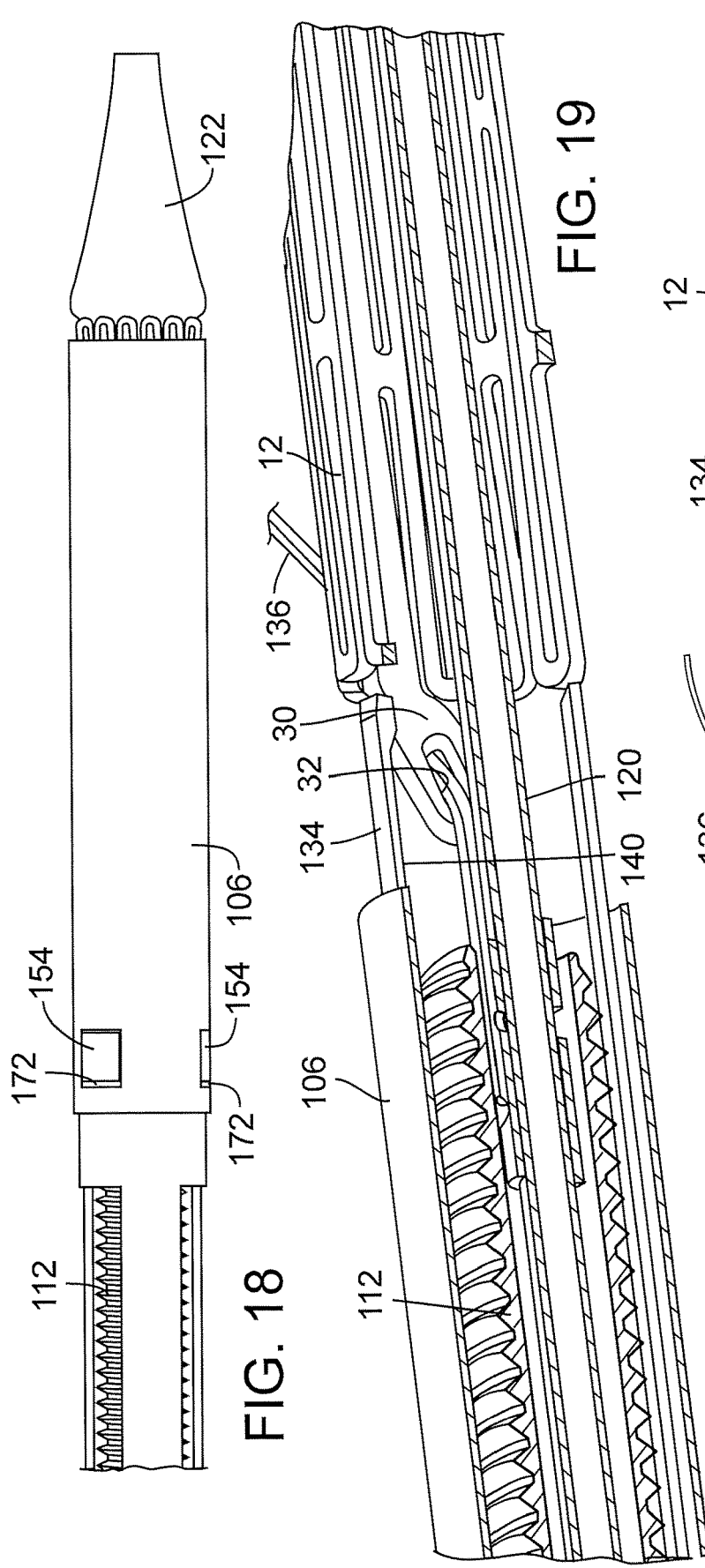
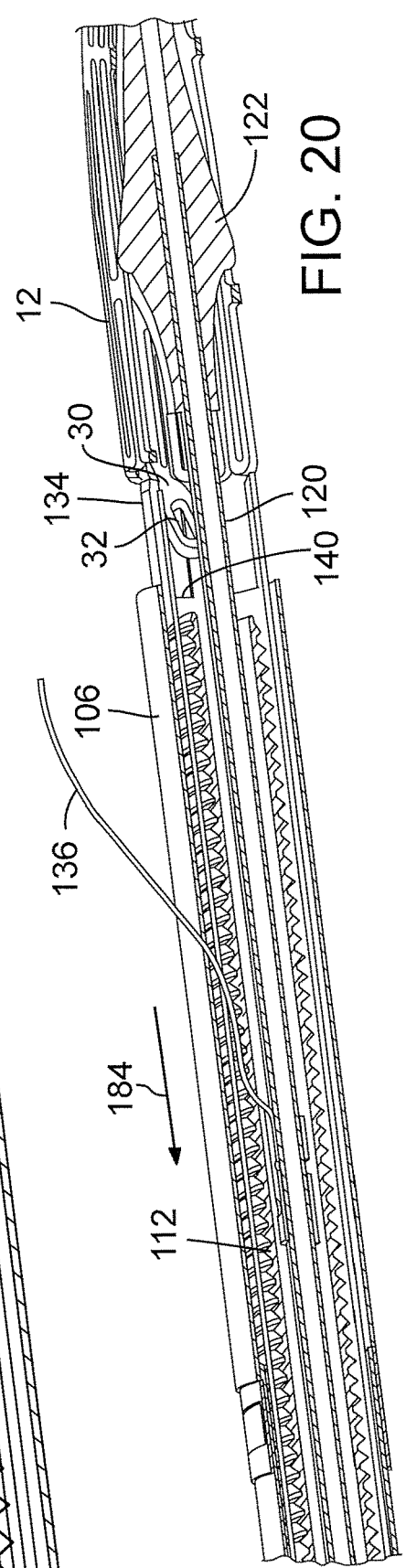

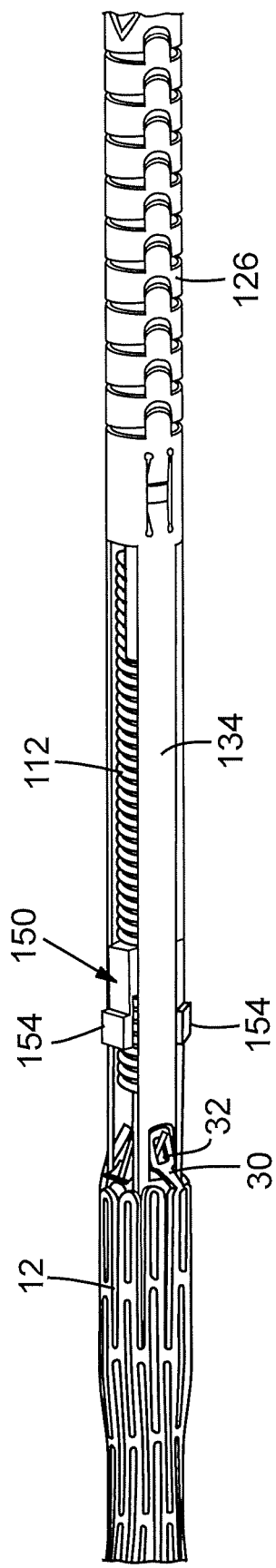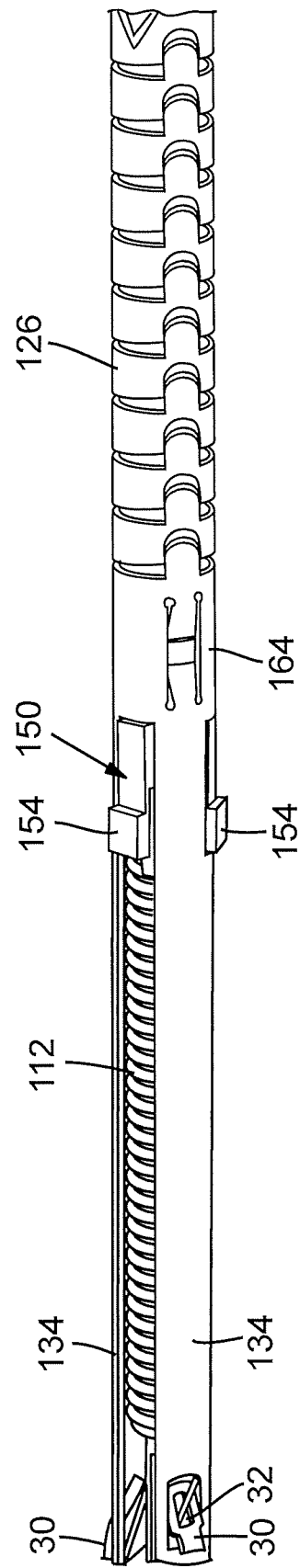

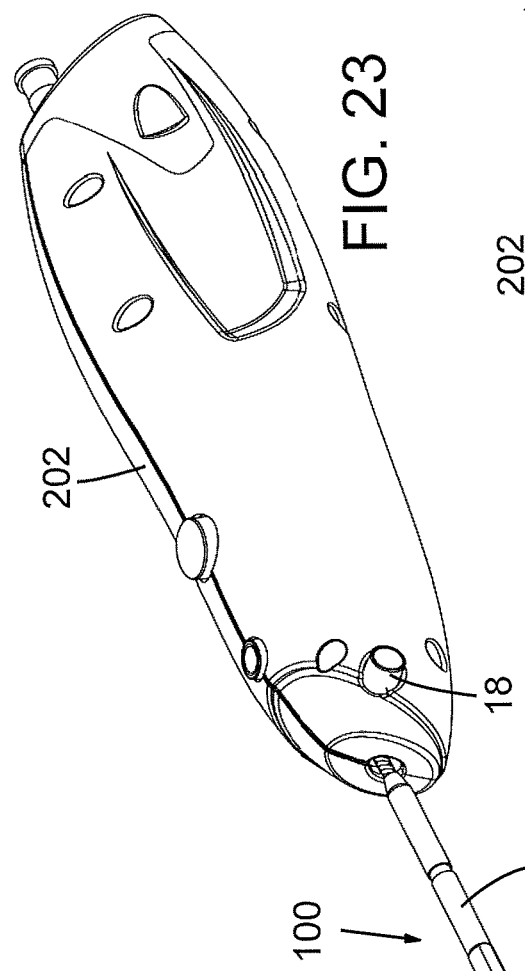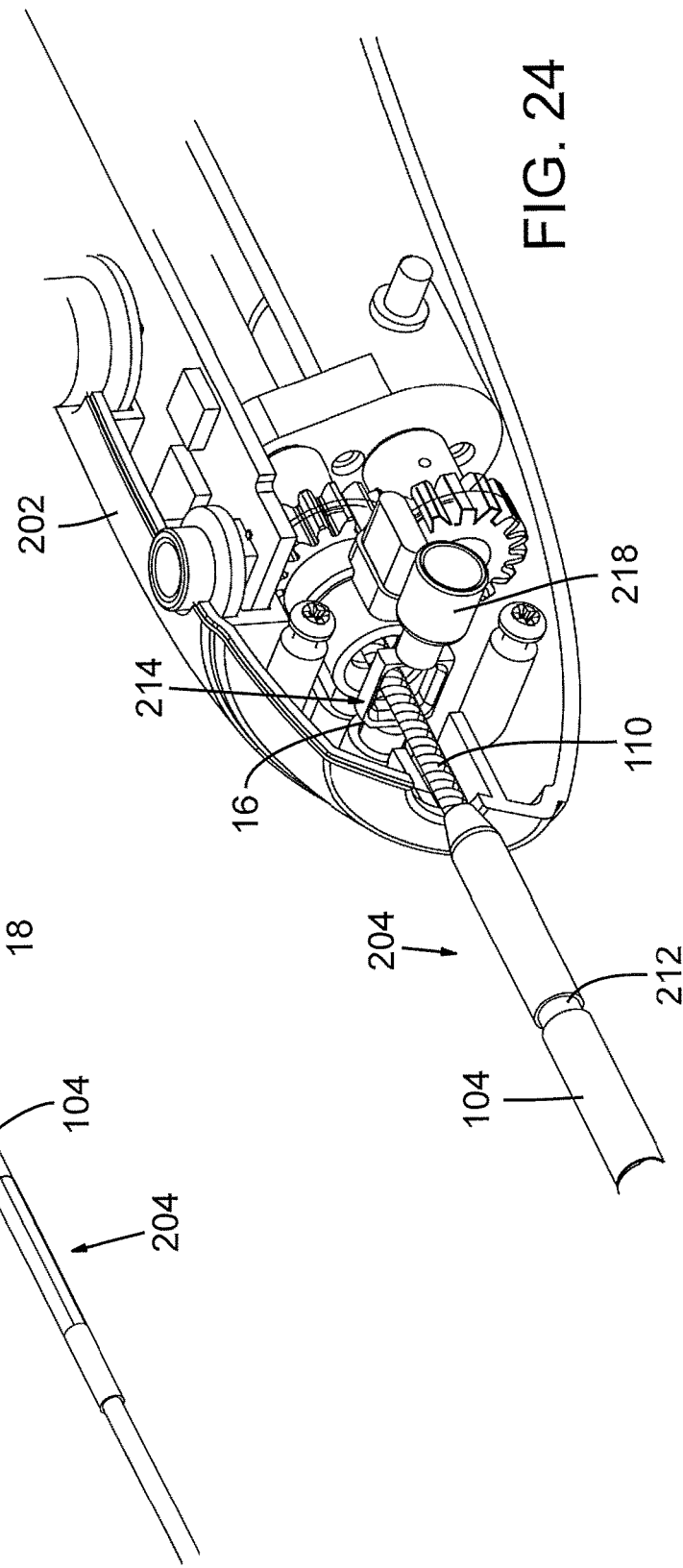

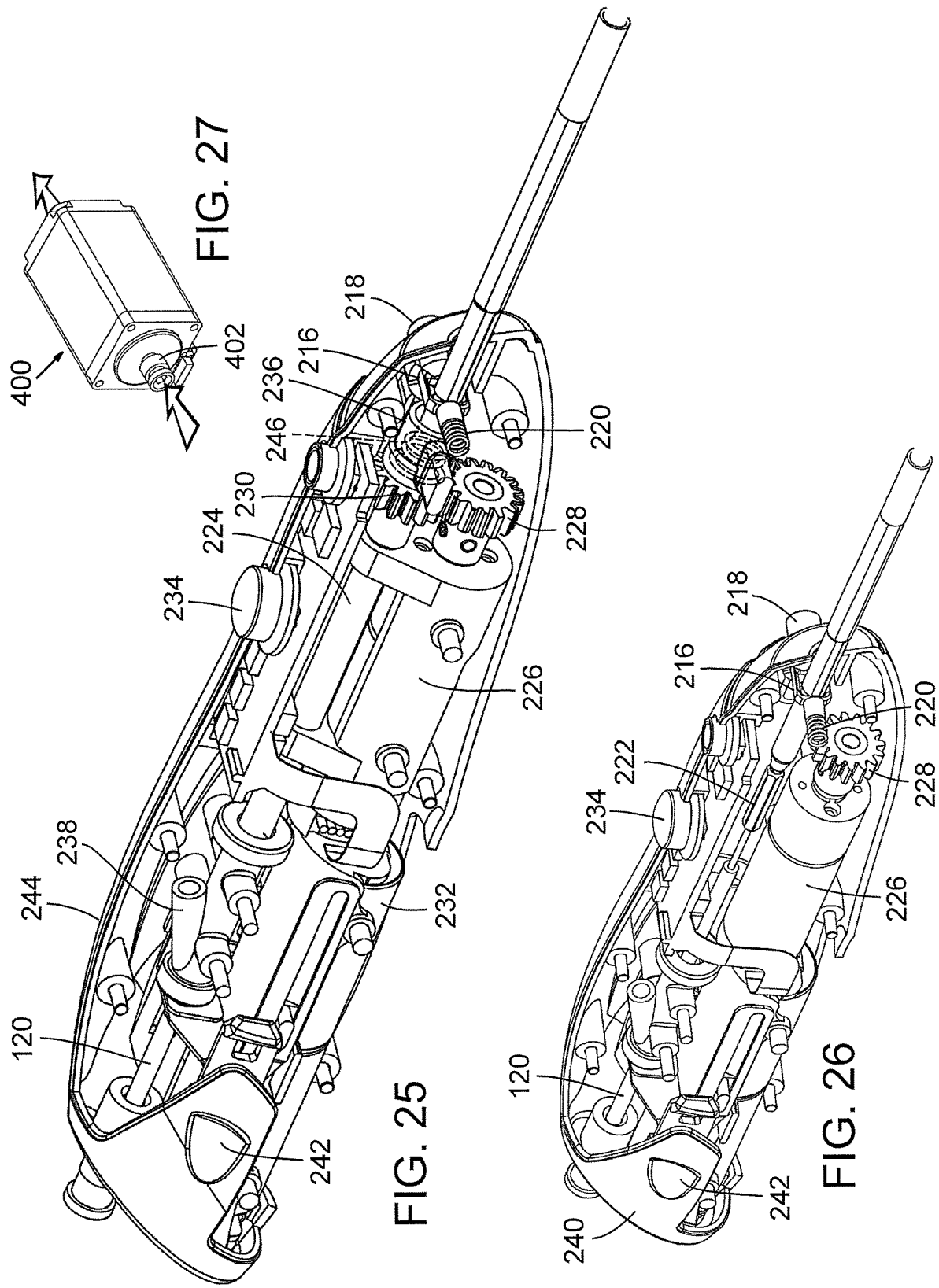

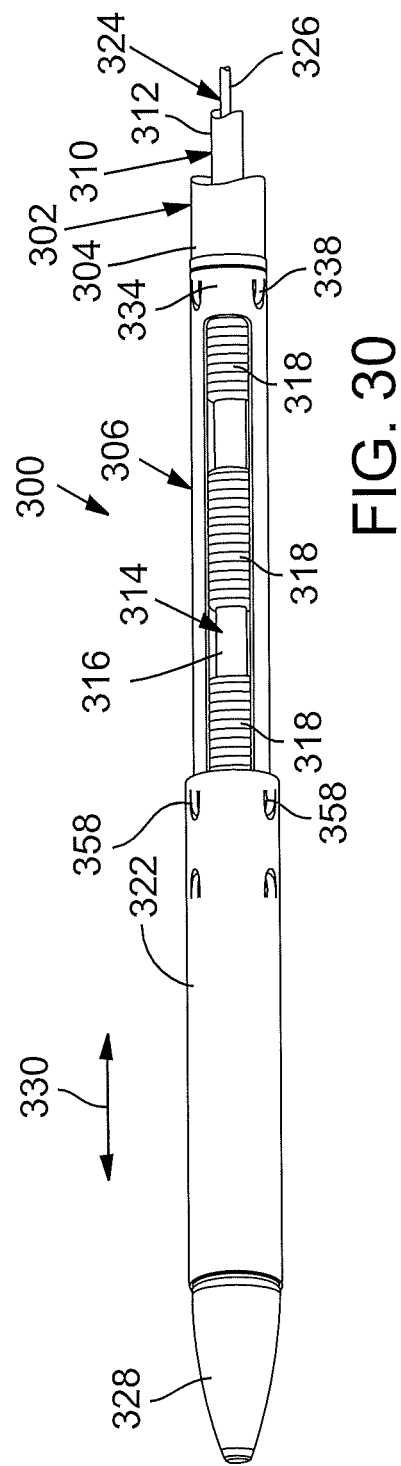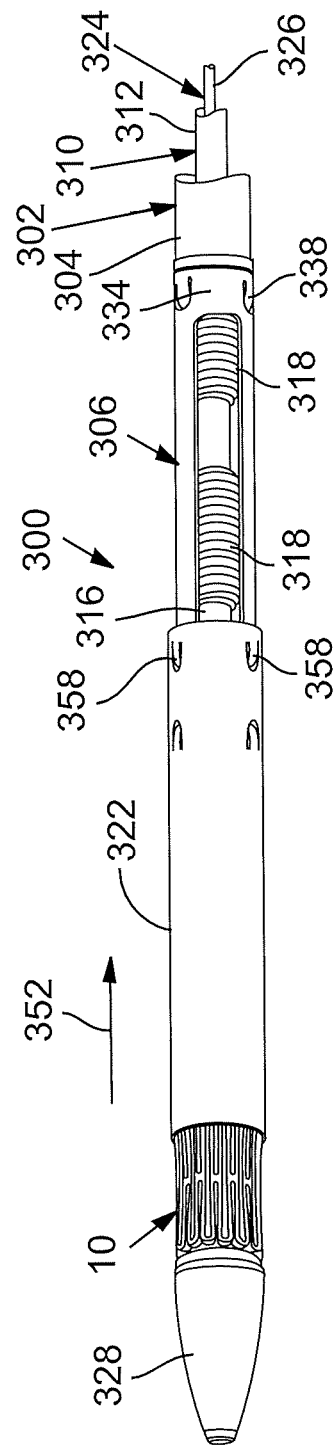

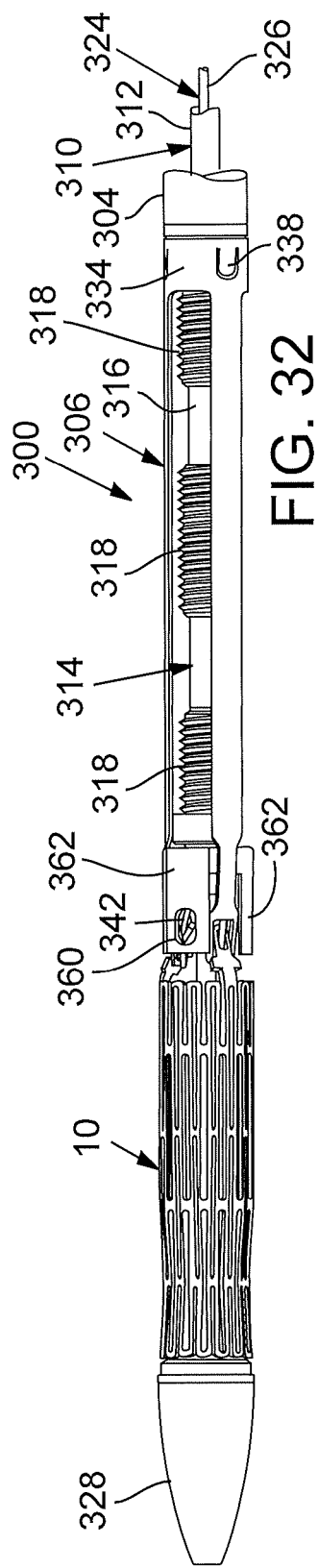
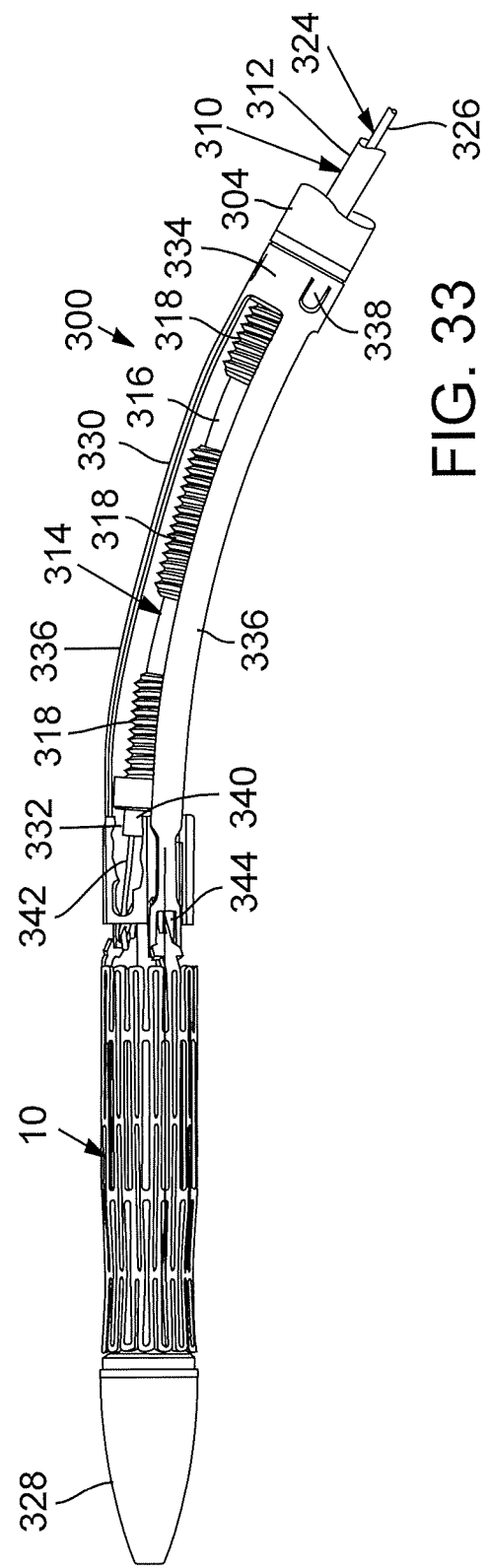

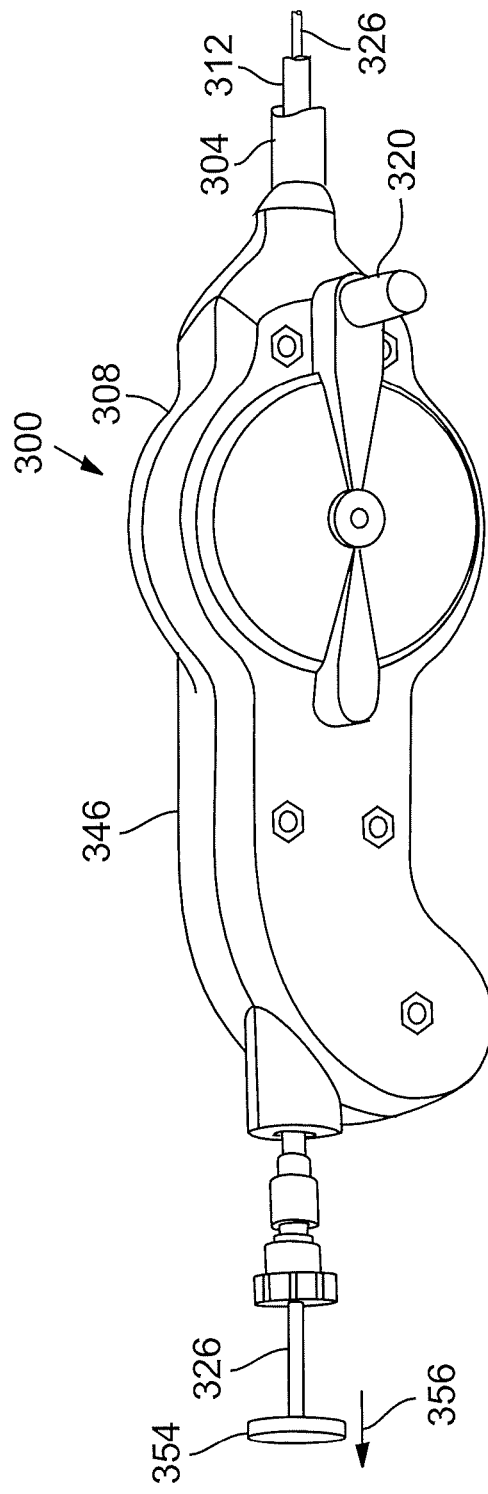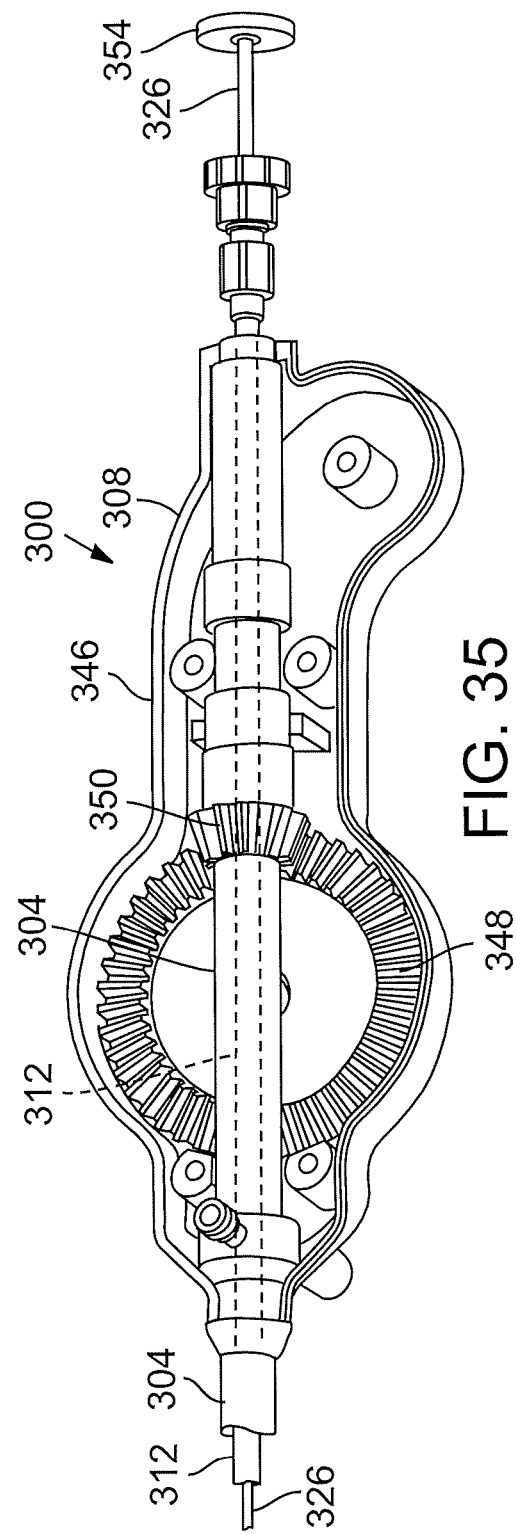

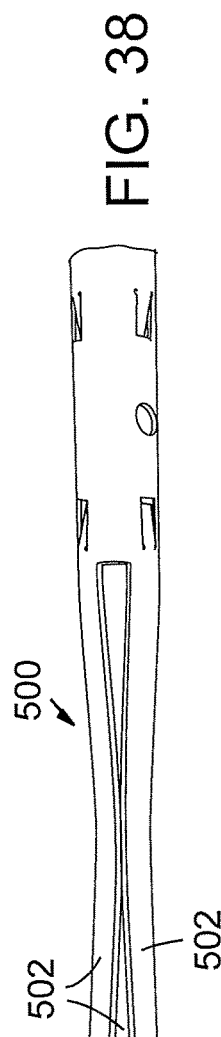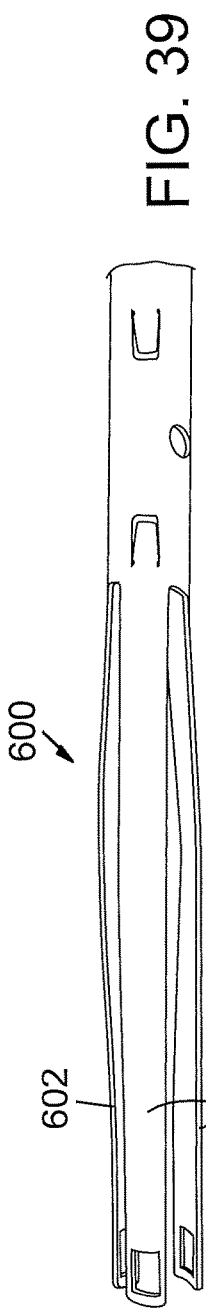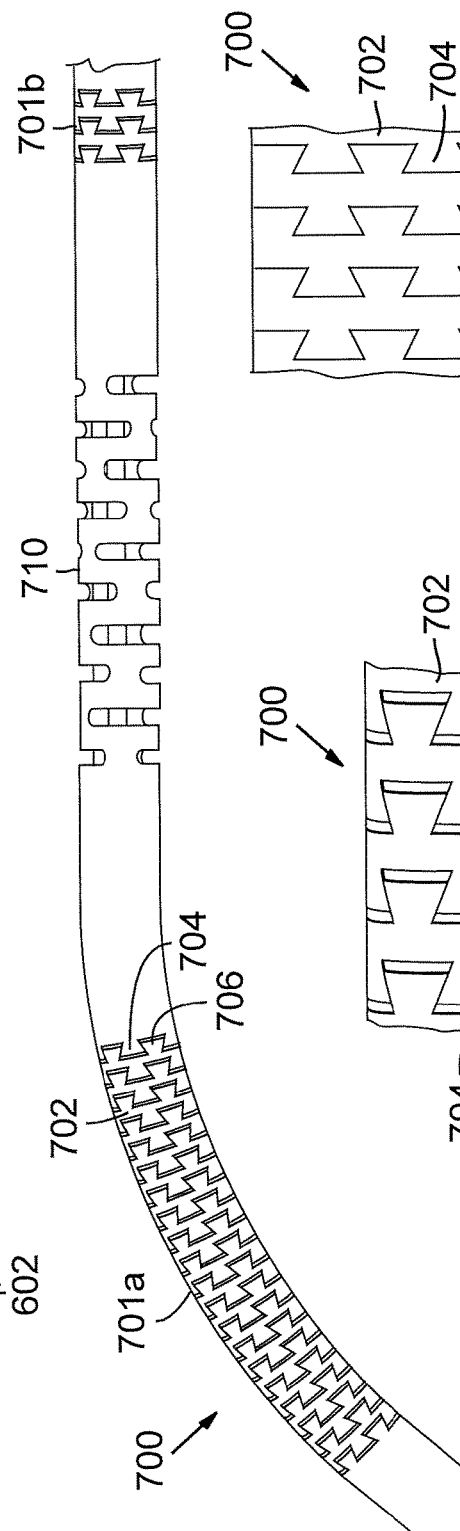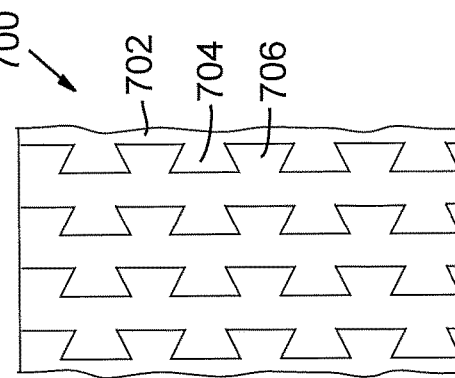

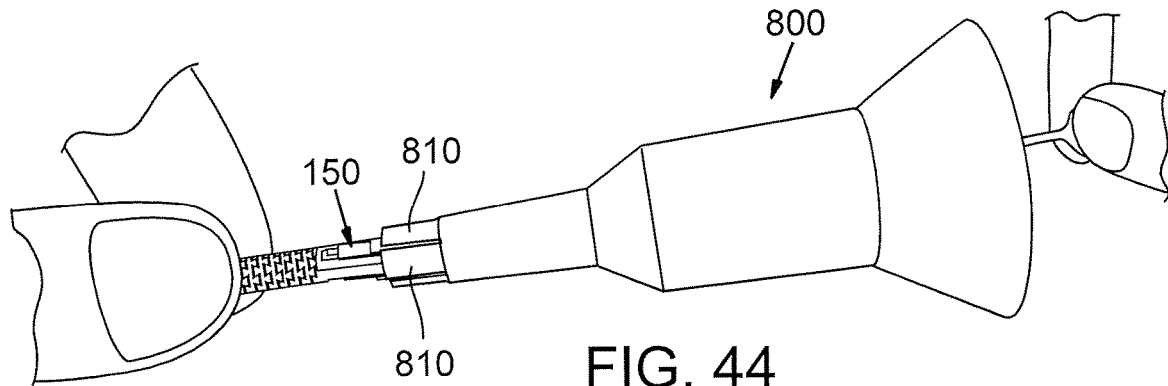
FIG. 44
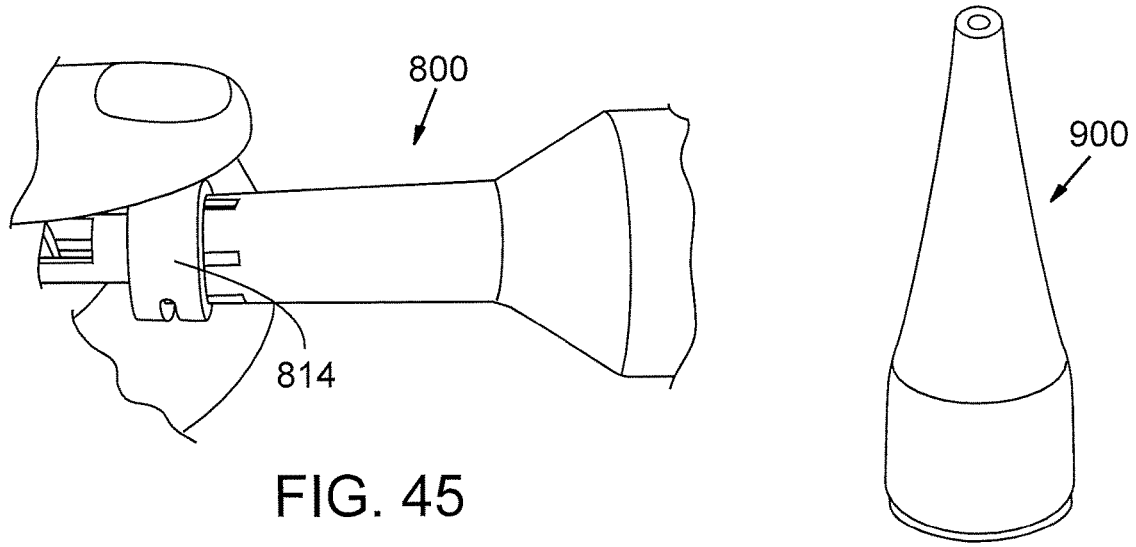
FIG. 45
FIG. 46
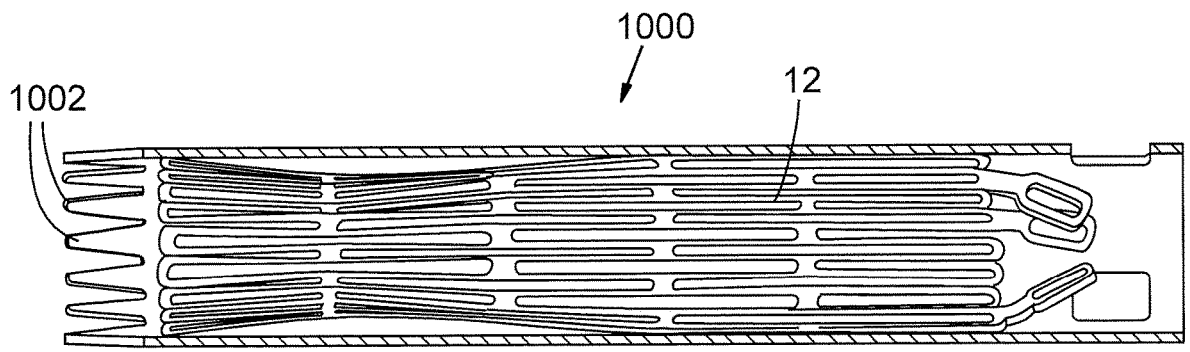
FIG. 47

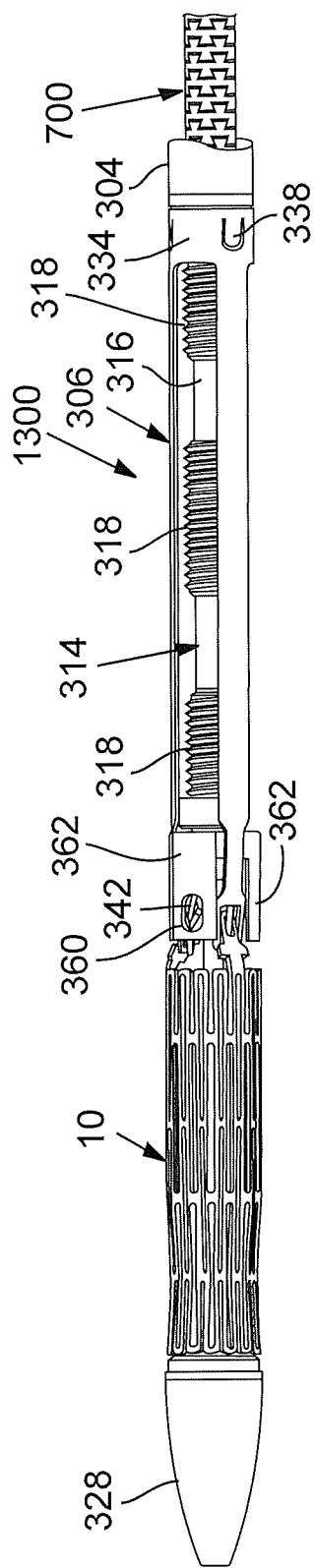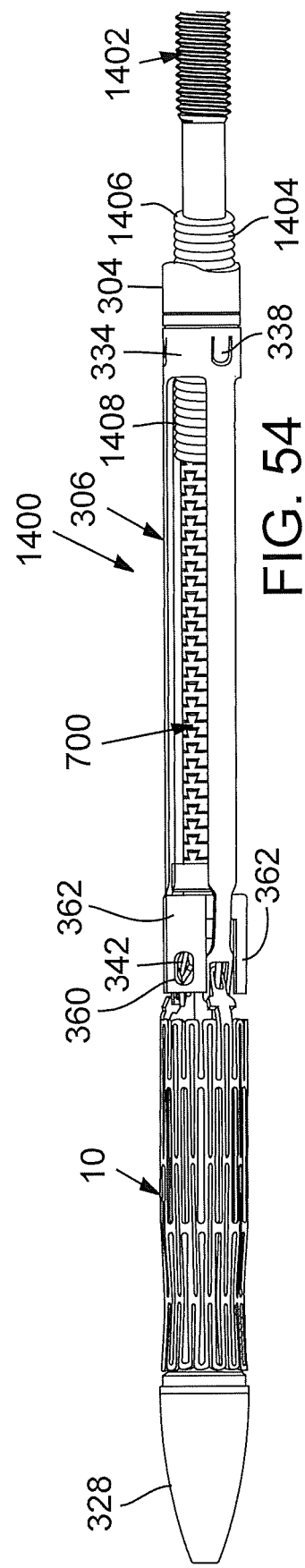

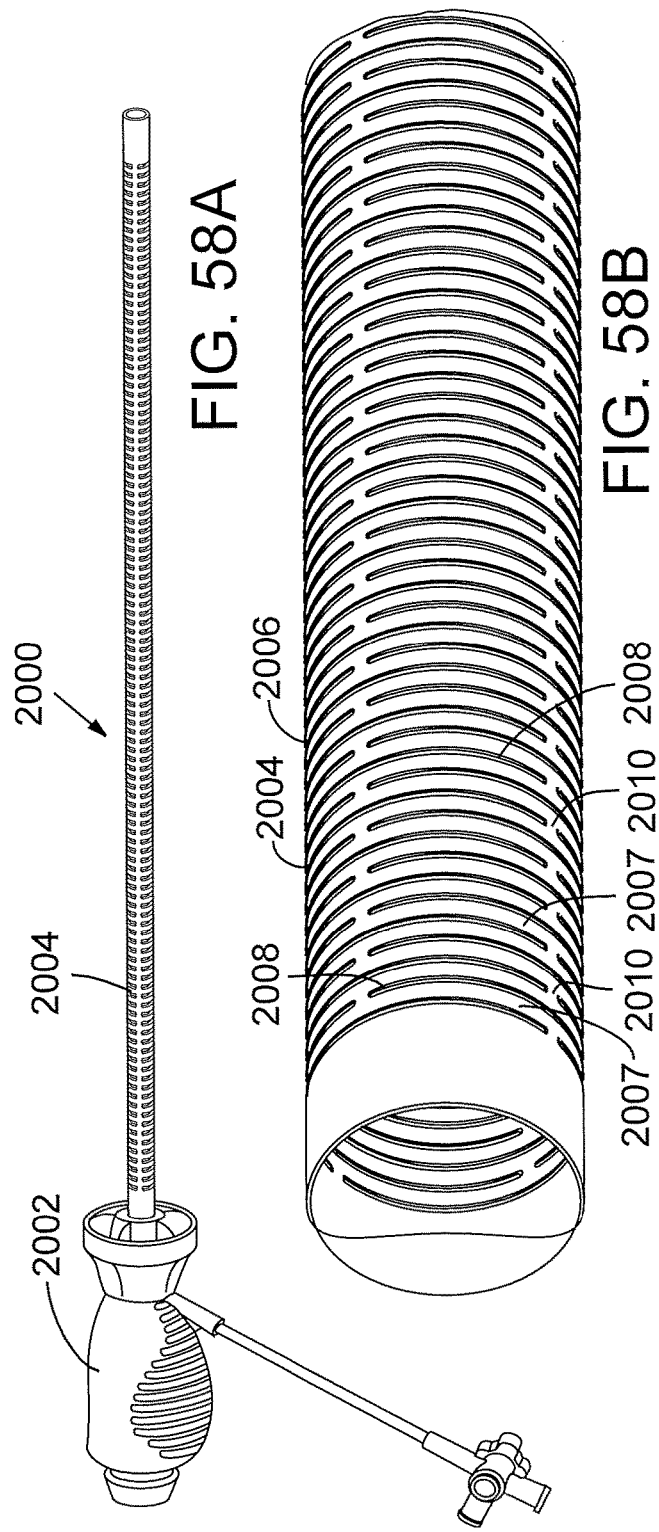
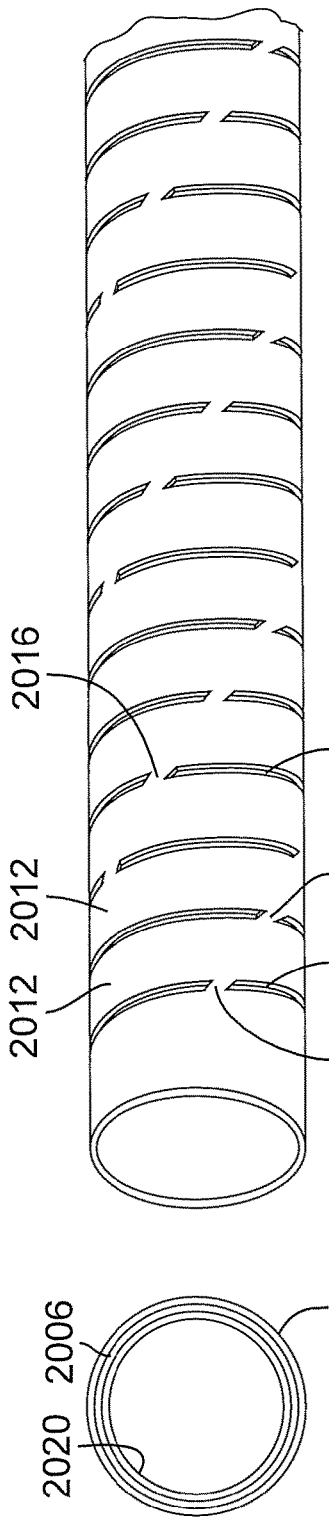
FIG. 58A
FIG. 58B
FIG. 59
FIG. 60

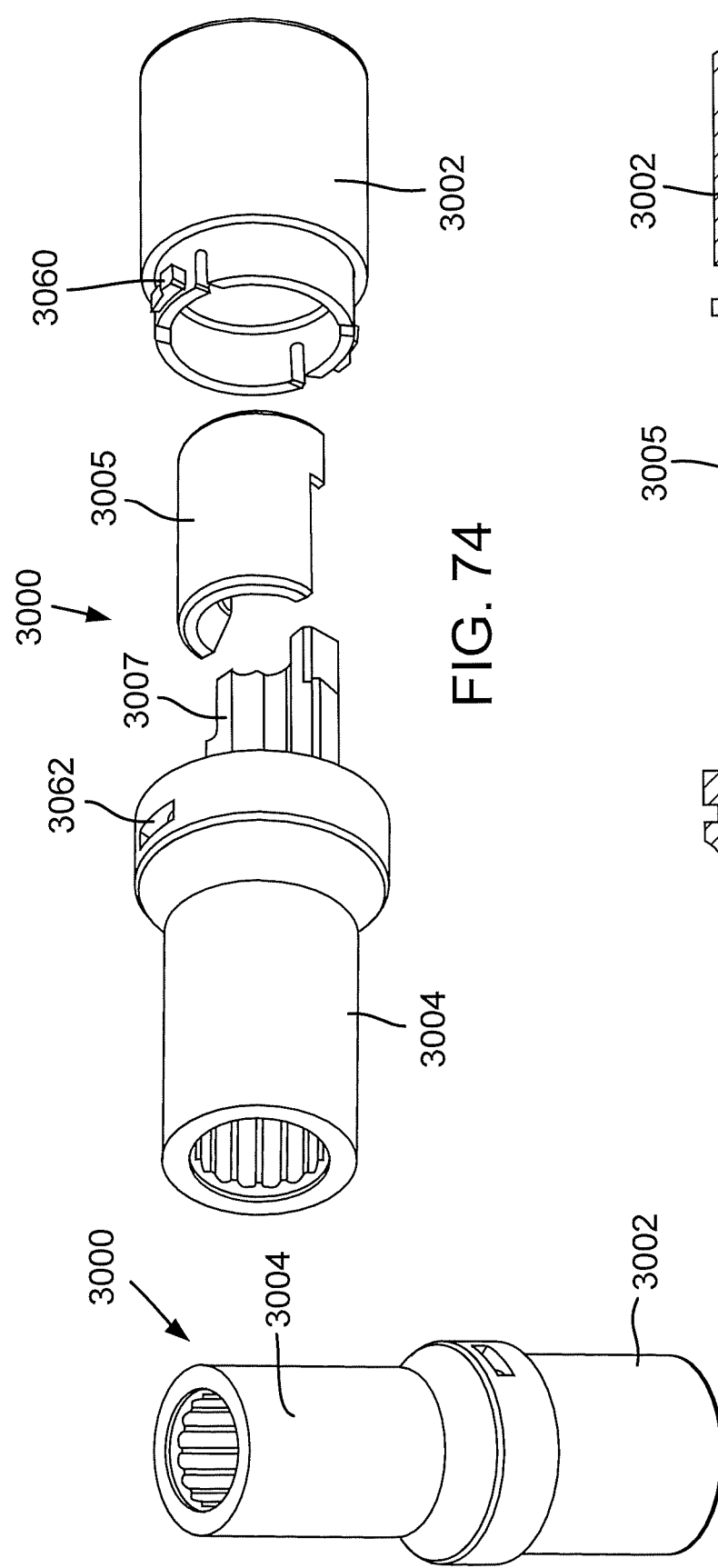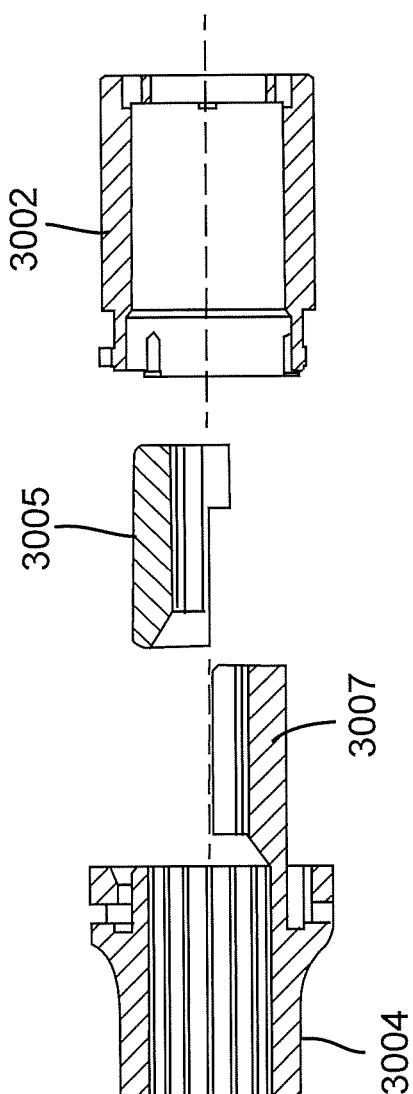

PROSTHETIC HEART VALVE DELIVERY APPARATUS

CROSS-REFERENCE TO RELATED APPLICATIONS

This application is a continuation of U.S. application Ser. No. 16/783,005, filed Feb. 5, 2020, which is a continuation of U.S. application Ser. No. 16/353,905, filed Mar. 14, 2019, which is a continuation of U.S. application Ser. No. 14/794,690, filed Jul. 8, 2015, now U.S. Pat. No. 10,561,494, which is a continuation of U.S. application Ser. No. 13/405,119, filed Feb. 24, 2012, now U.S. Pat. No. 9,155,619, which claims the benefit of U.S. Provisional Application No. 61/446,972, filed Feb. 25, 2011, all of which are incorporated by reference herein.

FIELD

The present disclosure concerns embodiments of prosthetic valves (e.g., prosthetic heart valves) and delivery apparatus for implanting a prosthetic valve.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

Balloon-expandable prosthetic valves typically are preferred for replacing calcified native valves because the catheter balloon can apply sufficient expanding force to anchor the frame of the prosthetic valve to the surrounding calcified tissue. On the other hand, self-expanding prosthetic valves sometimes are preferred for replacing a defective, non-stenotic (non-calcified) native valve, although they also can be used to replace stenotic valves. One drawback associated with implanting a self-expanding prosthetic valve is that as the operator begins to advance the prosthetic valve from the open end of the delivery sheath, the prosthetic valve tends to "jump" out very quickly from the end of the sheath; in other words, the outward biasing force of the prosthetic valve's frame tends to cause the prosthetic valve to be ejected very quickly from the distal end of the delivery sheath, making it difficult to deliver the prosthetic valve from the sheath in a precise and controlled manner and increasing the risk of trauma to the patient.

Another problem associated with implanting a percutaneous prosthetic valve in a non-stenotic native valve is that the prosthetic valve may not be able to exert sufficient force against the surrounding tissue to resist migration of the prosthetic valve. Typically, the stent of the prosthetic valve must be provided with additional anchoring or attachment devices to assist in anchoring the prosthetic valve to the surrounding tissue. Moreover, such anchoring devices or portions of the stent that assist in anchoring the prosthetic valve typically extend into and become fixed to non-diseased areas of the vasculature, which can result in complications if future intervention is required, for example, if the prosthetic valve needs to be removed from the patient.

SUMMARY

Certain embodiments of the present disclosure provide a prosthetic valve (e.g., a prosthetic heart valve) and a valve delivery apparatus for delivery of the prosthetic valve to a native valve site via the human vasculature. The delivery apparatus is particularly suited for advancing a prosthetic valve through the aorta (i.e., in a retrograde approach) for replacing a diseased native aortic valve. The delivery apparatus in particular embodiments is configured to deploy a prosthetic valve from a delivery sheath in a precise and controlled manner at the target location within the body.

In one representative embodiment, a delivery apparatus for implanting a prosthetic valve comprises a first elongated shaft having a proximal end portion and a distal end portion, and a second elongated shaft extending through the first shaft and having a proximal end portion and a distal end portion. The second shaft is rotatable relative to the first shaft but is fixed against axial movement relative to the first shaft. The distal end portion of the second shaft has an outer surface comprising external threads or grooves. A sheath retaining ring is disposed on the threads or grooves of the second shaft and is fixed against rotational movement relative to the distal end portion of the second shaft. A delivery sheath is configured to receive and retain a prosthetic valve in a compressed delivery state, the delivery sheath being connected to the sheath retaining ring. The second shaft is configured to be rotatable relative to the first shaft such that rotation of the second shaft causes the sheath retaining ring to move axially along the threads or grooves, thereby moving the sheath axially relative to the first and second shafts to deploy a prosthetic valve contained within the sheath.

In one implementation, the distal end portion of the second shaft comprises a screw having external threads and the sheath retaining ring comprises a nut having internal threads that engage the external threads on the screw. In another implementation, the distal end portion of the second shaft comprises a coil having external grooves and the sheath retaining ring comprises a washer that engages the grooves on the coil.

In another representative embodiment, a delivery apparatus for implanting a prosthetic valve comprises a first elongated shaft having a proximal end portion and a distal end portion, and a second elongated shaft extending through the first shaft and having a proximal end portion and a distal end portion. The second shaft is rotatable relative to the first shaft but is desirably fixed against axial movement relative to the first shaft. A third elongated shaft extends through the second shaft and has a proximal end portion and a distal end portion. A delivery sheath coupled to the second shaft is configured to receive and retain a prosthetic valve in a compressed delivery state. The delivery apparatus can further include a valve-retaining mechanism comprising first and second components on the distal end portion of the third shaft and the distal end portion of the first shaft, respectively, the first and second components cooperating to form a releasable connection with a stent of the prosthetic valve. The second shaft is configured to be rotatable relative to the first shaft such that rotation of the second shaft causes the sheath to move axially relative to the first, second and third shafts to deploy a prosthetic valve contained within the sheath. The valve-retaining mechanism prevents axial and rotational movement of the prosthetic valve relative to the first and third shafts as the second shaft is rotated to move the sheath axially to deploy the prosthetic valve.

BRIEF DESCRIPTION OF THE DRAWINGS

FIG. 8 is a cross-sectional view of an embodiment of a delivery apparatus that can be used to deliver and implant a prosthetic valve, such as the prosthetic valve shown in FIG. 1.

FIGS. 8A-8C are enlarged cross-sectional views of sections of FIG. 8.

FIG. 9 is an exploded view of the delivery apparatus of FIG. 8.

FIG. 10 is a side view of the guide catheter of the delivery apparatus of FIG. 8.

FIG. 11 is a perspective, exploded view of the proximal end portion of the guide catheter of FIG. 10.

FIG. 12 is a perspective, exploded view of the distal end portion of the guide catheter of FIG. 10.

FIG. 18 is an enlarged side view of the distal end portion of the delivery apparatus of FIG. 8 showing the delivery sheath in a delivery position covering a prosthetic valve in a compressed state for delivery into a patient.

FIG. 19 is an enlarged cross-sectional view of a section of the distal end portion of the delivery apparatus of FIG. 8 showing the valve-retaining mechanism securing the stent of a prosthetic valve to the delivery apparatus.

FIG. 20 is an enlarged cross-sectional view similar to FIG. 19, showing the inner fork of the valve-retaining mechanism in a release position for releasing the prosthetic valve from the delivery apparatus.

FIGS. 21 and 22 are enlarged side views of distal end portion of the delivery apparatus of FIG. 8, illustrating the operation of the torque shaft for deploying a prosthetic valve from a delivery sheath.

FIGS. 23-26 are various views of an embodiment of a motorized delivery apparatus that can be used to operate the torque shaft of the delivery apparatus shown in FIG. 8.

FIG. 27 is a perspective view of an alternative motor that can be used to operate the torque shaft of the delivery apparatus shown in FIG. 8.

FIG. 30 is a side view of the distal end portion of another embodiment of a delivery apparatus.

FIG. 31 is a side view similar to FIG. 30 showing the sheath of the delivery apparatus in a partially retracted position.

FIG. 32 is a side view similar to FIG. 30 shown with the sheath removed for purposes of illustration.

FIG. 33 is a side view similar to FIG. 32 showing a portion of the delivery apparatus in a bent position. This figure illustrates that the delivery apparatus can exhibit sufficient flexibility along the portion containing the screw mechanism.

FIG. 34 is a perspective view of the handle portion of the delivery apparatus shown in FIG. 30, according to one embodiment.

FIG. 35 is a perspective view illustrating the inside of the handle portion.

FIG. 38 is a side view of a modified valve-retaining mechanism, according to one embodiment.

FIG. 39 is a side view of a modified valve-retaining mechanism, according to another embodiment.

FIG. 40 is a side view of a section of a torque shaft that can be used in a delivery apparatus, according to one embodiment.

FIG. 40A is an enlarged view of a section of the torque shaft shown in FIG. 40.

FIG. 41 shows the cut pattern for forming the torque shaft of FIG. 40, such as by laser cutting a metal tube.

FIGS. 42-45 illustrate a loading cone and method of using the loading cone to load a prosthetic valve into the sheath of a delivery apparatus (e.g., the delivery apparatus of FIG. 8), according to one embodiment.

FIG. 46 is a perspective view of an alternative embodiment of a loading cone.

FIGS. 47-48 show an alternative embodiment of a sheath of a delivery apparatus.

FIGS. 53-57 are side views of the distal end portions of five additional embodiments of delivery apparatuses.

FIG. 58A is a perspective view of an introducer sheath, according to another embodiment.

FIG. 58B is an enlarged, perspective view of the sleeve of the introducer sheath of FIG. 58A.

FIG. 59 is an enlarged, perspective view of another embodiment of a sleeve that can be used with the introducer sheath of FIG. 58A.

FIG. 60 is an end view of a sleeve that can be used with the introducer sheath of FIG. 58A.

FIG. 73 is a perspective view of a storage tube assembly for storing a prosthetic valve in a partially crimped state, according to one embodiment.

FIG. 74 is an exploded, perspective view of the storage tube assembly of FIG. 73

FIG. 75 is an exploded, cross-sectional view of the storage tube assembly of FIG. 75.

FIGS. 89-113 are various views illustrating an exemplary method for partially crimping a prosthetic valve for storage and eventual use.

DETAILED DESCRIPTION

Figure 1:
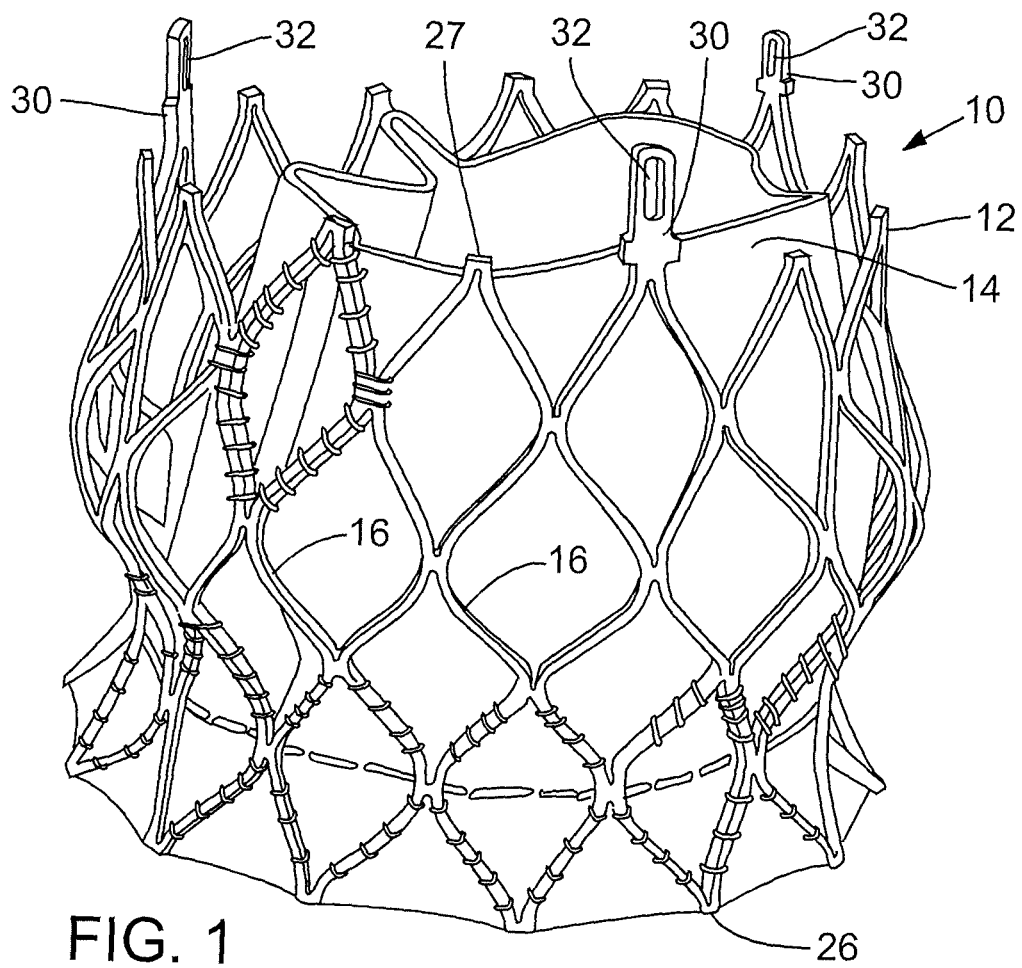
FIG. 1 is a perspective view of a prosthetic valve that can be used to replace the native aortic valve of the heart, according to one embodiment.

Referring first to FIG. 1, there is shown a prosthetic aortic heart valve 10, according to one embodiment. The prosthetic valve 10 includes an expandable frame member, or stent, 12 that supports a flexible leaflet section 14. The prosthetic valve 10 is radially compressible to a compressed state for delivery through the body to a deployment site and expandable to its functional size shown in FIG. 1 at the deployment site. In certain embodiments, the prosthetic valve 10 is self-expanding; that is, the prosthetic valve can radially expand to its functional size when advanced from the distal end of a delivery sheath. Apparatuses particularly suited for percutaneous delivery and implantation of a self-expanding prosthetic valve are described in detail below. In other embodiments, the prosthetic valve can be a balloon-expandable prosthetic valve that can be adapted to be mounted in a compressed state on the balloon of a delivery catheter. The prosthetic valve can be expanded to its functional size at a deployment site by inflating the balloon.

The illustrated prosthetic valve 10 is adapted to be deployed in the native aortic annulus, although it also can be used to replace the other native valves of the heart. Moreover, the prosthetic valve 10 can be adapted to replace other valves within the body, such as venous valves.

Figure 3:
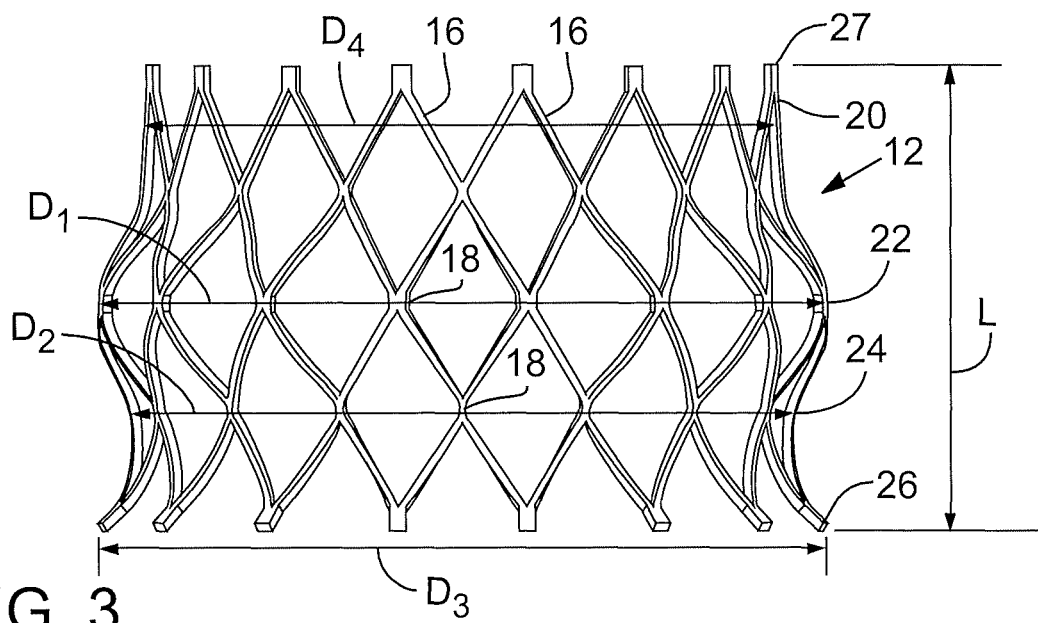
FIG. 3 is side elevation view of the support frame of the prosthetic valve of FIG. 1.
Figure 4:
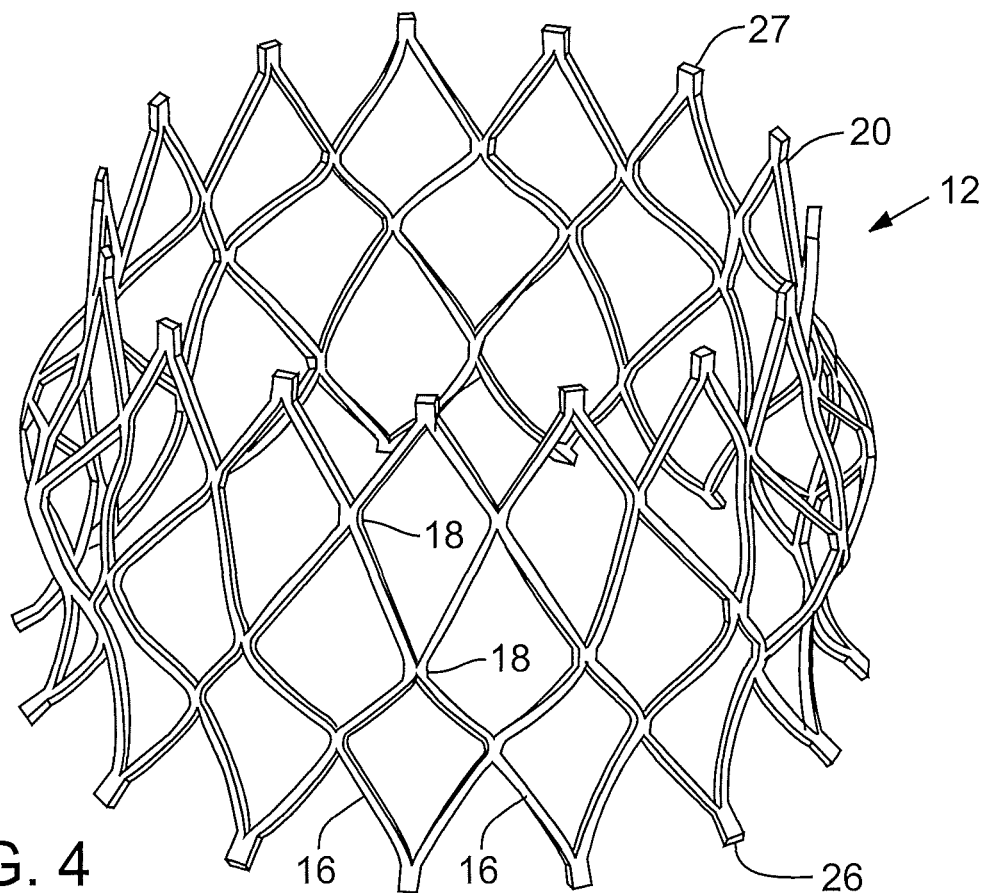
FIG. 4 is a perspective view of the support frame of the prosthetic valve of FIG. 1.

FIGS. 3 and 4 show the stent 12 without the leaflet section 14 for purposes of illustration. As shown, the stent 12 can be formed from a plurality of longitudinally extending, generally sinusoidal shaped frame members, or struts, 16. The struts 16 are formed with alternating bends and are welded or otherwise secured to each other at nodes 18 formed from the vertices of adjacent bends so as to form a mesh structure. The struts 16 can be made of a suitable shape memory material, such as the nickel titanium alloy known as Nitinol, that allows the prosthetic valve to be compressed to a reduced diameter for delivery in a delivery apparatus (such as described below) and then causes the prosthetic valve to expand to its functional size inside the patient's body when deployed from the delivery apparatus. If the prosthetic valve is a balloon-expandable prosthetic valve that is adapted to be crimped onto an inflatable balloon of a delivery apparatus and expanded to its functional size by inflation of the balloon, the stent 12 can be made of a suitable ductile material, such as stainless steel.

The stent 12 has an inflow end 26 and an outflow end 27. The mesh structure formed by struts 16 comprises a generally cylindrical "upper" or outflow end portion 20, an outwardly bowed or distended intermediate section 22, and an inwardly bowed "lower" or inflow end portion 24. The intermediate section 22 desirably is sized and shaped to extend into the Valsalva sinuses in the root of the aorta to assist in anchoring the prosthetic valve in place once implanted. As shown, the mesh structure desirably has a curved shape along its entire length that gradually increases in diameter from the outflow end portion 20 to the intermediate section 22, then gradually decreases in diameter from the intermediate section 22 to a location on the inflow end portion 24, and then gradually increases in diameter to form a flared portion terminating at the inflow end 26.

Figure 5A:
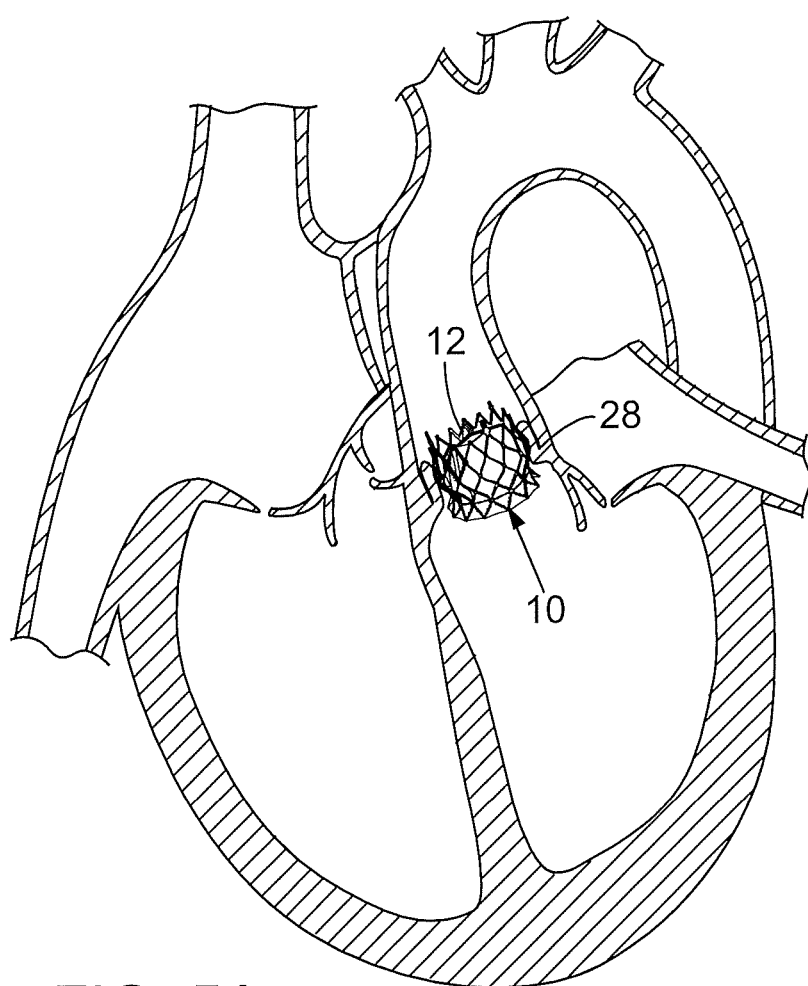
FIG. 5A is a cross-sectional view of the heart showing the prosthetic valve of FIG. 1 implanted within the aortic annulus.
Figure 5B:
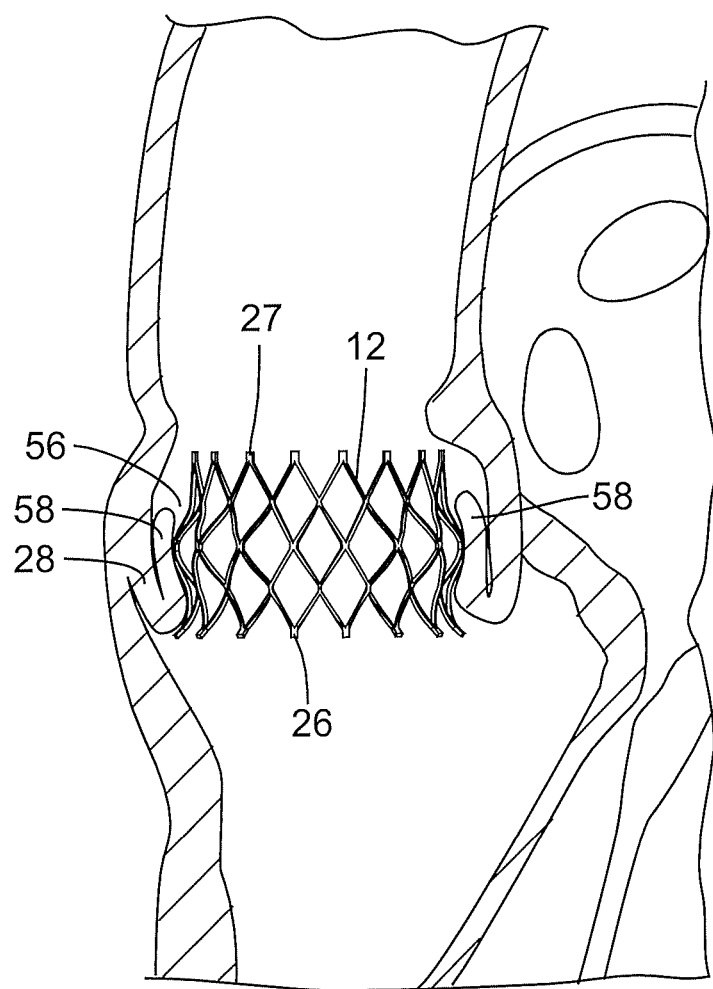
FIG. 5B is an enlarged view of FIG. 5A illustrating the prosthetic valve implanted within the aortic annulus, shown with the leaflet structure of the prosthetic valve removed for clarity.

When the prosthetic valve is in its expanded state, the intermediate section 22 has a diameter $D_1$, the inflow end portion 24 has a minimum diameter $D_2$, the inflow end 26 has a diameter $D_3$, and the outflow end portion 20 has a diameter $D_4$, where $D_2$ is less than $D_1$ and $D_3$, and $D_4$ is less than $D_2$. In addition, $D_1$ and $D_3$ desirably are greater than the diameter of the native annulus in which the prosthetic valve is to be implanted. In this manner, the overall shape of the stent 12 assists in retaining the prosthetic valve at the implantation site. More specifically, and referring to FIGS. 5A and 5B, the prosthetic valve 10 can be implanted within a native valve (the aortic valve in the illustrated example) such that the lower section 24 is positioned within the aortic annulus 28, the intermediate section 24 extends above the aortic annulus into the Valsalva's sinuses 56, and the lower flared end 26 extends below the aortic annulus. The prosthetic valve 10 is retained within the native valve by the radial outward force of the lower section 24 against the surrounding tissue of the aortic annulus 28 as well as the geometry of the stent. Specifically, the intermediate section 24 and the flared lower end 26 extend radially outwardly beyond the aortic annulus 28 to better resist against axial dislodgement of the prosthetic valve in the upstream and downstream directions (toward and away from the aorta). Depending on the condition of the native leaflets 58, the prosthetic valve typically is deployed within the native annulus 28 with the native leaflets 58 folded upwardly and compressed between the outer surface of the stent 12 and the walls of the Valsalva sinuses, as depicted in FIG. 5B. In some cases, it may be desirable to excise the leaflets 58 prior to implanting the prosthetic valve 10.

Known prosthetic valves having a self-expanding frame typically have additional anchoring devices or frame portions that extend into and become fixed to non-diseased areas of the vasculature. Because the shape of the stent 12 assists in retaining the prosthetic valve, additional anchoring devices are not required and the overall length L of the stent can be minimized to prevent the stent upper portion 20 from extending into the non-diseased area of the aorta, or to at least minimize the extent to which the upper portion 20 extends into the non-diseased area of the aorta. Avoiding the non-diseased area of the patient's vasculature helps avoid complications if future intervention is required. For example, the prosthetic valve can be more easily removed from the patient because the stent is primarily anchored to the diseased part of the native valve. Furthermore, a shorter prosthetic valve is more easily navigated around the aortic arch.

In particular embodiments, for a prosthetic valve intended for use in a 22-mm to 24-mm annulus, the diameter D1 is about 28 mm to about 32 mm, with 30 mm being a specific example; the diameter D2 is about 24 mm to about 28 mm, with 26 mm being a specific example; the diameter D3 is about 28 mm to about 32 mm, with 30 mm being a specific example; and the diameter D4 is about 24 mm to about 28 mm, with 26 mm being a specific example. The length L in particular embodiments is about 20 mm to about 24 mm, with 22 mm being a specific example.

Referring to FIG. 1, the stent 12 can have a plurality of angularly spaced retaining arms, or projections, in the form of posts 30 (three in the illustrated embodiment) that extend from the stent upper portion 20. Each retaining arm 30 has a respective aperture 32 that is sized to receive prongs of a valve-retaining mechanism that can be used to form a releasable connection between the prosthetic valve and a delivery apparatus (described below). In alternative embodiments, the retaining arms 30 need not be provided if a valve-retaining mechanism is not used.

Figure 6:
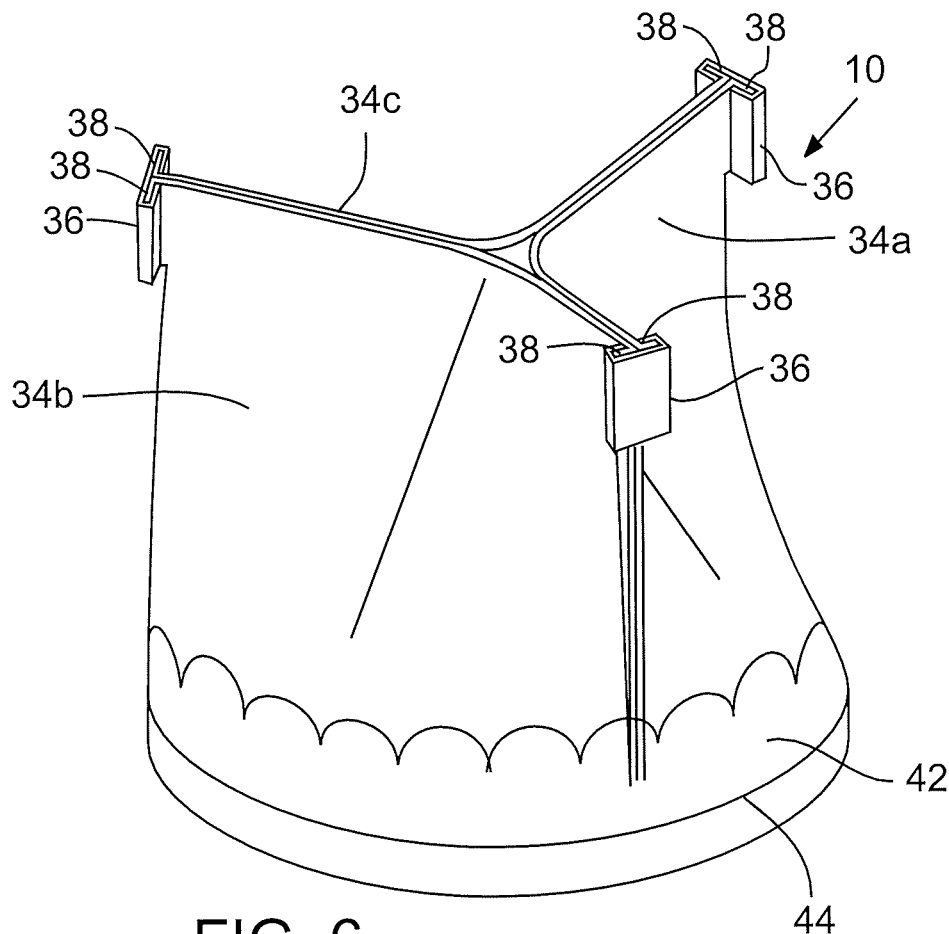
FIG. 6 is a perspective view of the leaflet structure of the prosthetic valve of FIG. 1 shown prior to being secured to the support frame.
Figure 7:
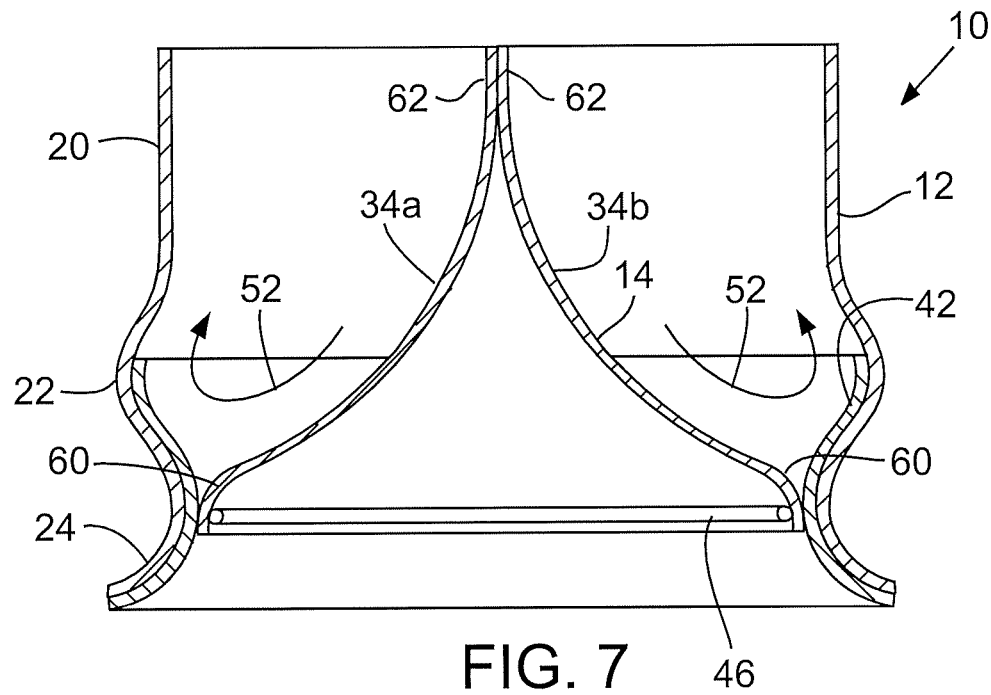
FIG. 7 is a cross-sectional view of the prosthetic valve of FIG. 1.

As best shown in FIGS. 6 and 7, the leaflet assembly 14 in the illustrated embodiment comprises three leaflets 34a, 34b, 34c made of a flexible material. Each leaflet has an inflow end portion 60 and an outflow end portion 62. The leaflets can comprise any suitable biological material (e.g., pericardial tissue, such as bovine or equine pericardium), bio-compatible synthetic materials, or other such materials, such as those described in U.S. Pat. No. 6,730,118, which is incorporated herein by reference. The leaflet assembly 14 can include an annular reinforcing skirt 42 that is secured to the outer surfaces of the inflow end portions of the leaflets 34a, 34b, 34c at a suture line 44 adjacent the inflow end of the prosthetic valve. The inflow end portion of the leaflet assembly 14 can be secured to the stent 12 by suturing the skirt 42 to struts 16 of the lower section 24 of the stent (best shown in FIG. 1). As shown in FIG. 7, the leaflet assembly 14 can further include an inner reinforcing strip 46 that is secured to the inner surfaces of the inflow end portions 60 of the leaflets.

Figure 2:
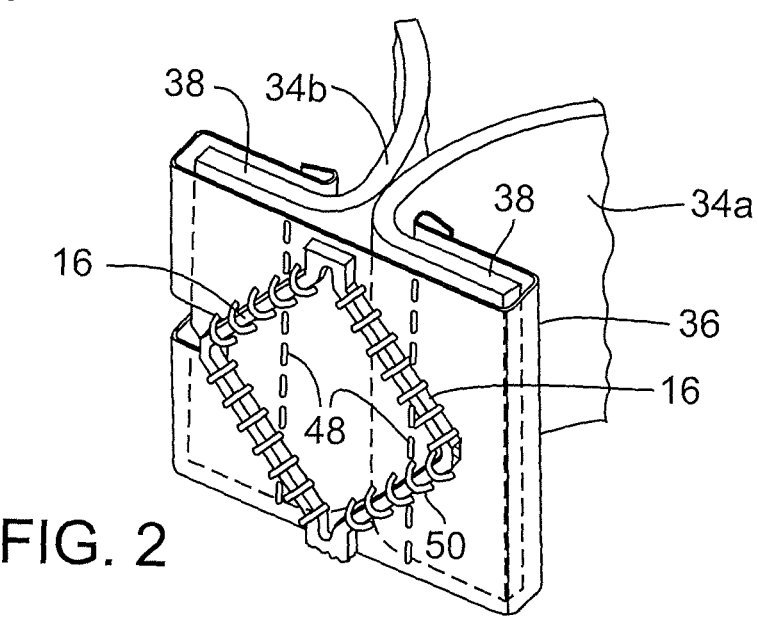
FIG. 2 is a perspective view of a portion of the prosthetic valve of FIG. 1 illustrating the connection of two leaflets to the support frame of the prosthetic valve.

Referring to FIGS. 1 and 2, the outflow end portion of the leaflet assembly 14 can be secured to the upper portion of the stent 12 at three angularly spaced commissure attachments of the leaflets 34a, 34b, 34c. As best shown in FIG. 2, each commissure attachment can be formed by wrapping a reinforcing section 36 around adjacent upper edge portions 38 of a pair of leaflets at the commissure formed by the two leaflets and securing the reinforcing section 36 to the edge portions 38 with sutures 48. The sandwiched layers of the reinforcing material and leaflets can then be secured to the struts 16 of the stent 12 with sutures 50 adjacent the outflow end of the stent. The leaflets therefore desirably extend the entire length or substantially the entire length of the stent from the inflow end 26 to the outflow end 27. The reinforcing sections 36 reinforces the attachment of the leaflets to the stent so as to minimize stress concentrations at the suture lines and avoid "needle holes" on the portions of the leaflets that flex during use. The reinforcing sections 36, the skirt 42, and the inner reinforcing strip 46 desirably are made of a bio-compatible synthetic material, such as polytetrafluoroethylene (PTFE), or a woven fabric material, such as woven polyester (e.g., polyethylene terephtalate) (PET)).

FIG. 7 shows the operation of the prosthetic valve 10. During diastole, the leaflets 34a, 34b, 34c collapse to effectively close the prosthetic valve. As shown, the curved shape of the intermediate section 22 of the stent 12 defines a space between the intermediate section and the leaflets that mimics the Valsalva sinuses. Thus, when the leaflets close, backflow entering the "sinuses" creates a turbulent flow of blood along the upper surfaces of the leaflets, as indicated by arrows 52. This turbulence assists in washing the leaflets and the skirt 42 to minimize clot formation.

The prosthetic valve 10 can be implanted in a retrograde approach where the prosthetic valve, mounted in a crimped state at the distal end of a delivery apparatus, is introduced into the body via the femoral artery and advanced through the aortic arch to the heart, as further described in U.S. Patent Publication No. 2008/0065011, which is incorporated herein by reference.

FIGS. 8 and 9 show a delivery apparatus 100, according to one embodiment, that can be used to deliver a self-expanding prosthetic valve, such as prosthetic valve 10 described above, through a patient's vasculature. The delivery apparatus 100 comprises a first, outermost or main catheter 102 (shown alone in FIG. 10) having an elongated shaft 104, the distal end of which is coupled to a delivery sheath 106 (FIG. 18; also referred to as a delivery cylinder). The proximal end of the main catheter 102 is connected to a handle of the delivery apparatus. FIGS. 23-26 show an embodiment of a handle mechanism having an electric motor for operating the delivery apparatus. The handle mechanism is described in detail below. During delivery of a prosthetic valve, the handle can be used by a surgeon to advance and retract the delivery apparatus through the patient's vasculature. Although not required, the main catheter 102 can comprise a guide catheter that is configured to allow a surgeon to guide or control the amount the bending or flexing of a distal portion of the shaft 104 as it is advanced through the patient's vasculature, such as further described below. Another embodiment of a guide catheter is disclosed in U.S. Patent Publication No. 2008/0065011, which is incorporated herein by reference.

As best shown in FIG. 9, the delivery apparatus 100 also includes a second, intermediate catheter 108 (also referred to herein as a torque shaft catheter) having an elongated shaft 110 (also referred to herein as a torque shaft) and an elongated screw 112 connected to the distal end of the shaft 110. The shaft 110 of the intermediate catheter 108 extends coaxially through the shaft 104 of the main catheter 102. The delivery apparatus 100 can also include a third, nosecone catheter 118 having an elongated shaft 120 and a nose piece, or nose cone, 122 secured to the distal end portion of the shaft 120. The nose piece 122 can have a tapered outer surface as shown for atraumatic tracking through the patient's vasculature. The shaft 120 of the nosecone catheter extends through the prosthetic valve 10 (not shown in FIGS. 8-9) and the shaft 110 of the intermediate catheter 108. In the illustrated configuration, the innermost shaft 120 is configured to be moveable axially and rotatably relative to the shafts 104, 110, and the torque shaft 110 is configured to be rotatable relative to the shafts 104, 120 to effect valve deployment and release of the prosthetic valve from the delivery apparatus, as described in detail below. Additionally, the innermost shaft 120 can have a lumen for receiving a guide wire so that the delivery apparatus can be advanced over the guide wire inside the patient's vasculature.

As best shown in FIG. 10, the outer catheter 102 can comprise a flex control mechanism 168 at a proximal end thereof to control the amount the bending or flexing of a distal portion of the outer shaft 104 as it is advanced through the patient's vasculature, such as further described below. The outer shaft 104 can comprise a proximal segment 166 that extends from the flex control mechanism 168 and a distal segment 126 that comprises a slotted metal tube that increases the flexibility of the outer shaft at this location. The distal end portion of the distal segment 126 can comprises an outer fork 130 of a valve-retaining mechanism 114 that is configured to releasably secure a prosthetic valve 10 to the delivery apparatus 100 during valve delivery, as described in detail below.

Figure 28A:
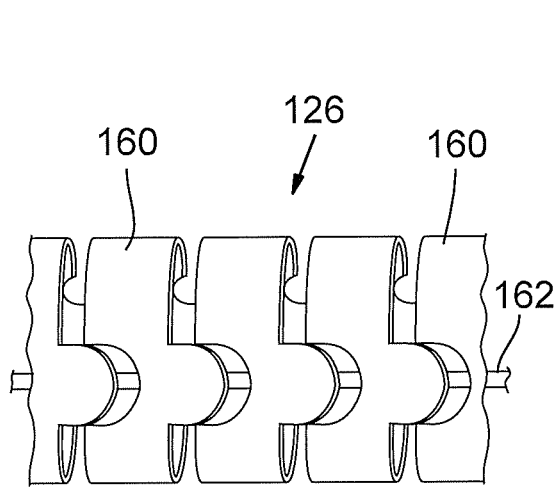
FIG. 28A is an enlarged view of a distal segment of the guide catheter shaft of FIG. 10.
Figure 28B:
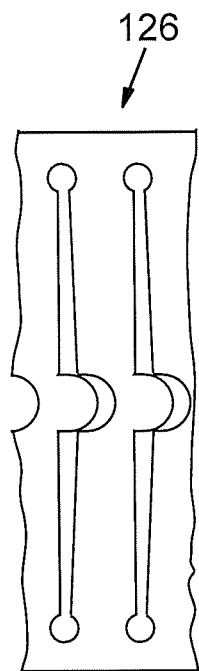
FIG. 28B shows the cut pattern for forming the portion of the shaft shown in FIG. 28A, such as by laser cutting a metal tube.

FIG. 28A is an enlarged view of a portion of the distal segment 126 of the outer shaft 104. FIG. 28B shows the cut pattern that can be used to form the distal segment 126 by laser cutting the pattern in a metal tube. The distal segment 126 comprises a plurality of interconnected circular bands or links 160 forming a slotted metal tube. A pull wire 162 can be positioned inside the distal segment 126 and can extend from a location 164 of the distal segment 126 (FIGS. 10 and 12) to the flex control mechanism. The distal end of the pull wire 162 can be secured to the inner surface of the distal segment 126 at location 164, such as by welding. The proximal end of the pull wire 162 can be operatively connected to the flex control mechanism 168, which is configured to apply and release tension to the pull wire in order to control bending of the shaft, as further described below. The links 160 of the shaft and the gaps between adjacent links are shaped to allow bending of the shaft upon application of light pulling force on the pull wire 162. In the illustrated embodiment, as best shown in FIG. 12, the distal segment 126 is secured to a proximal segment 166 having a different construction (e.g., one or more layers of polymeric tubing). In the illustrated embodiment, the proximal segment 166 extends from the flex control mechanism 168 to the distal segment 126 and therefore makes up the majority of the length of the outer shaft 104. In alternative embodiments, the entire length or substantially the entire length of the outer shaft 104 can be formed from a slotted metal tube comprising one or more sections of interconnected links 160. In any case, the use of a main shaft having such a construction can allow the delivery apparatus to be highly steerable, especially when use in combination with a torque shaft having the construction shown in FIGS. 40 and 41 (described below).

The width of the links 160 can be varied to vary the flexibility of the distal segment along its length. For example, the links within the distal end portion of the slotted tube can be relatively narrower to increase the flexibility of the shaft at that location while the links within the proximal end portion of the slotted tube can be relatively wider so that the shaft is relatively less flexible at that location.

Figure 29A:
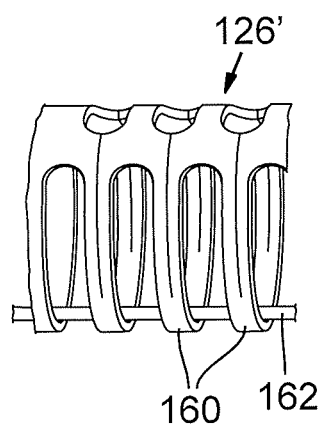
FIG. 29A is an enlarged view of a distal segment of a guide catheter shaft, according to another embodiment.
Figure 29B:
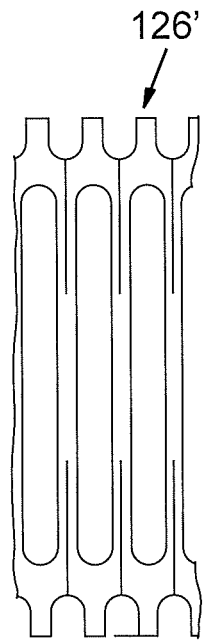
FIG. 29B shows the cut pattern for forming the shaft of FIG. 29A, such as by laser cutting a metal tube.

FIG. 29A shows an alternative embodiment of a distal segment, indicated at 126', which can be formed, for example, by laser cutting a metal tube. The segment 126' can comprise the distal segment of an outer shaft of a delivery apparatus (as shown in FIG. 12) or substantially the entire length of an outer shaft can have the construction shown in FIG. 29A. FIG. 29B shows the cut pattern for forming the segment 126'. In another embodiment, a delivery apparatus can include a composite outer shaft comprising a laser-cut metal tube laminated with a polymeric outer layer that is fused within the gaps in the metal layer. In one example, a composite shaft can comprise a laser cut metal tube having the cut pattern of FIGS. 29A and 29B and a polymeric outer layer fused in the gaps between the links 160 of the metal tube. In another example, a composite shaft can comprise a laser cut metal tube having the cut pattern of FIGS. 28A and 28B and a polymeric outer 49

Referring to FIGS. 8A and 11, the flex control mechanism 168 can comprise a rotatable housing, or handle portion, 186 that houses a slide nut 188 mounted on a rail 192. The slide nut 188 is prevented from rotating within the housing by one or more rods 192, each of which is partially disposed in a corresponding recess within the rail 192 and a slot or recess on the inside of the nut 188. The proximal end of the pull wire 162 is secured to the nut 188. The nut 188 has external threads that engage internal threads of the housing. Thus, rotating the housing 186 causes the nut 188 to move axially within the housing in the proximal or distal direction, depending on the direction of rotation of the housing. Rotating the housing in a first direction (e.g., clockwise), causes the nut to travel in the proximal direction, which applies tension to the pull wire 162, which causes the distal end of the delivery apparatus to bend or flex. Rotating the housing in a second direction (e.g., counterclockwise), causes the nut to travel in the distal direction, which relieves tension in the pull wire 162 and allows the distal end of the delivery apparatus to flex back to its pre-flexed configuration under its own resiliency.

Figure 13:
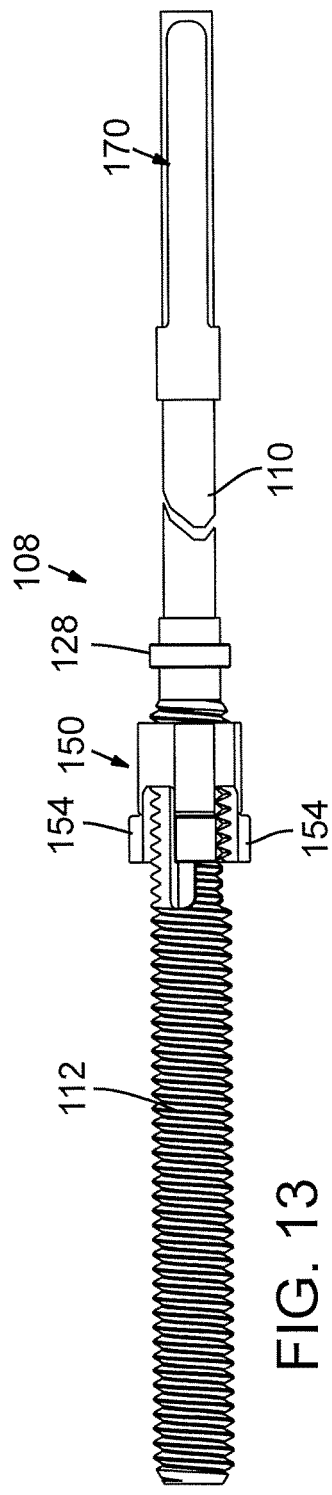
FIG. 13 is a side view of the torque shaft catheter of the delivery apparatus of FIG. 8.
Figure 14:
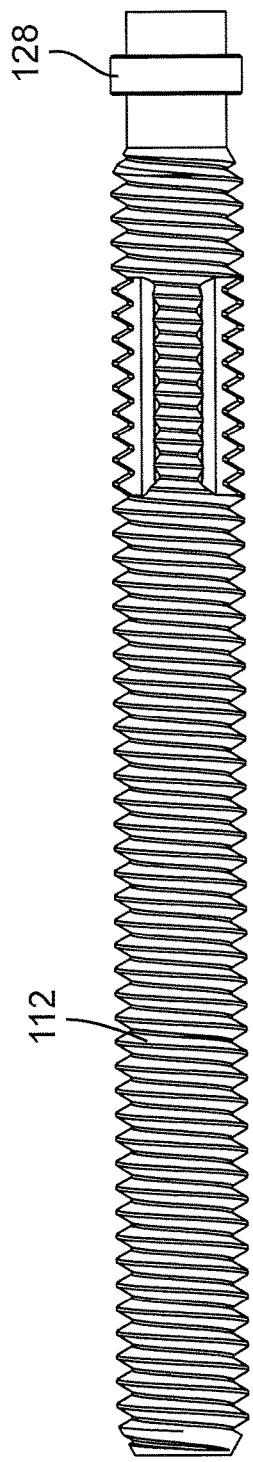
FIG. 14 is an enlarged side view of the rotatable screw of the torque shaft catheter of FIG. 13.

As best shown in FIG. 13, the torque shaft catheter 108 includes an annular projection in the form of a ring 128 (also referred to as an anchoring disc) mounted on the distal end portion of the torque shaft 110 adjacent the screw 112. The ring 128 is secured to the outer surface of the torque shaft 110 such that it cannot move axially or rotationally relative to the torque shaft. The inner surface of the outer shaft 104 is formed with a feature, such as a slot or recess, that receives the ring 128 in such a manner that the ring and the corresponding feature on the inner surface of the outer shaft 104 allow the torque shaft 110 to rotate relative to the outer shaft 104 but prevent the torque shaft from moving axially relative to the outer shaft. The corresponding feature on the outer shaft 104 that receives the ring 128 can be inwardly extending tab portions formed in the distal segment 126, such as shown at 164 in FIG. 12. In the illustrated embodiment (as best shown in FIG. 14), the ring 128 is an integral part of the screw 112 (i.e., the screw 112 and the ring 128 are portions of single component). Alternatively, the screw 112 and the ring are separately formed components but are both fixedly secured to the distal end of the torque shaft 110.

Figure 16:
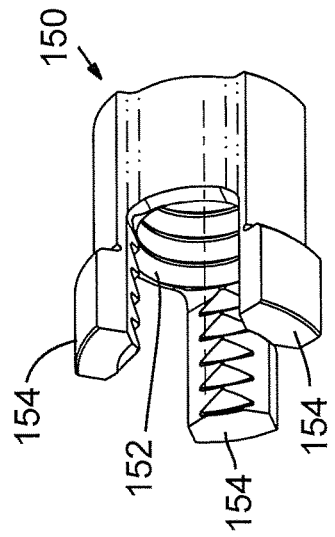
FIG. 16 is an enlarged perspective view of the threaded nut used in the torque shaft catheter of FIG. 13.

The torque shaft 110 desirably is configured to be rotatable relative to the delivery sheath 106 to effect incremental and controlled advancement of the prosthetic valve 10 from the delivery sheath 106. To such ends, and according to one embodiment, the delivery apparatus 100 can include a sheath retaining ring in the form of a threaded nut 150 mounted on the external threads of the screw 112. As best shown in FIG. 16, the nut 150 includes internal threads 152 that engage the external threads of the screw and axially extending legs 154. Each leg 154 has a raised distal end portion that extends into and/or forms a snap fit connection with openings 172 in the proximal end of the sheath 106 (as best shown in FIG. 18) so as to secure the sheath 106 to the nut 150. As illustrated in FIGS. 17B and 18, the sheath 106 extends over the prosthetic valve 10 and retains the prosthetic valve in a radially compressed state until the sheath 106 is retracted by the user to deploy the prosthetic valve.

As best shown in FIGS. 21 and 22, the outer fork 130 of the valve-retaining mechanism comprises a plurality of prongs 134, each of which extends through a region defined between two adjacent legs 154 of the nut so as to prevent rotation of the nut relative to the screw 112 upon rotation of the screw. As such, rotation of the torque shaft 110 (and thus the screw 112) causes corresponding axial movement of the nut 150. The connection between the nut 150 and the sheath 106 is configured such that axially movement of the nut along the screw 112 (in the distal or proximal direction) causes the sheath 106 to move axially in the same direction relative to the screw and the valve-retaining mechanism. FIG. 21 shows the nut 150 in a distal position wherein the sheath 106 (not shown in FIG. 21) extends over and retains the prosthetic valve 10 in a compressed state for delivery. Movement of the nut 150 from the distal position (FIG. 21) to a proximal position (FIG. 22) causes the sheath 106 to move in the proximal direction, thereby deploying the prosthetic valve from the sheath 106. Rotation of the torque shaft 110 to effect axial movement of the sheath 106 can be accomplished with a motorized mechanism (such as shown in FIGS. 23-26 and described below) or by manually turning a crank or wheel (such as shown in the embodiment of FIGS. 30-37, described below).

Figure 17:
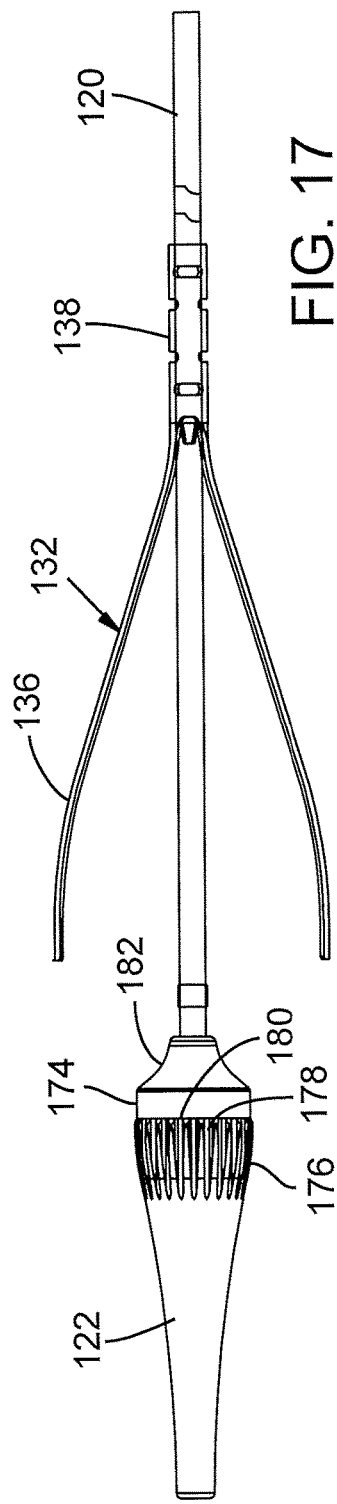
FIG. 17 is an enlarged side view of the distal end portion of the nose cone catheter of the delivery apparatus of FIG. 8.
Figure 17B:
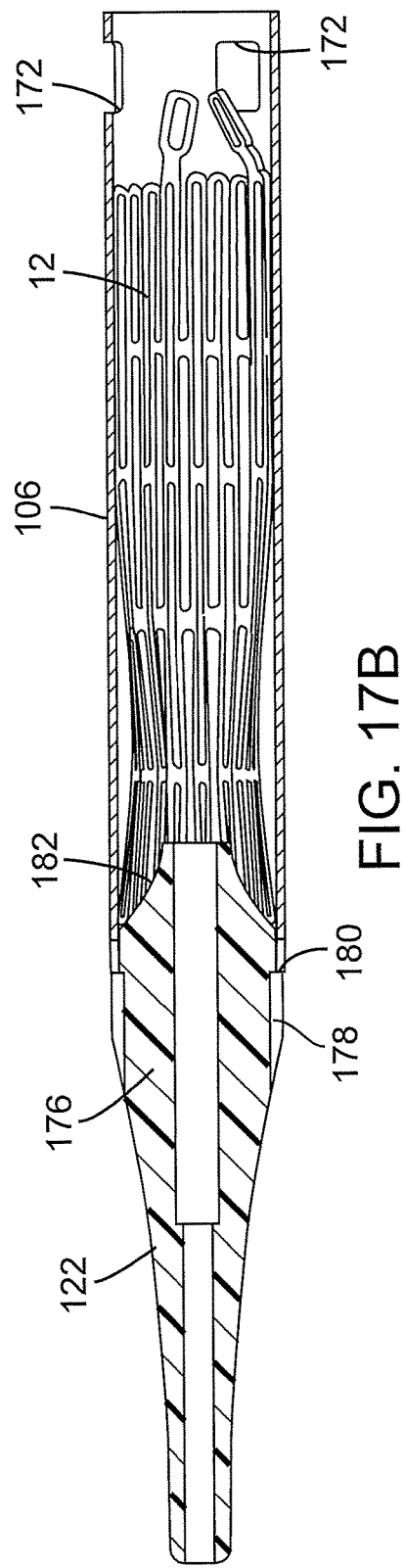
FIG. 17B is an enlarged cross-sectional view of the distal end portion of the delivery apparatus of FIG. 8 showing the stent of a prosthetic valve retained in a compressed state within a delivery sheath.
Figure 17A:
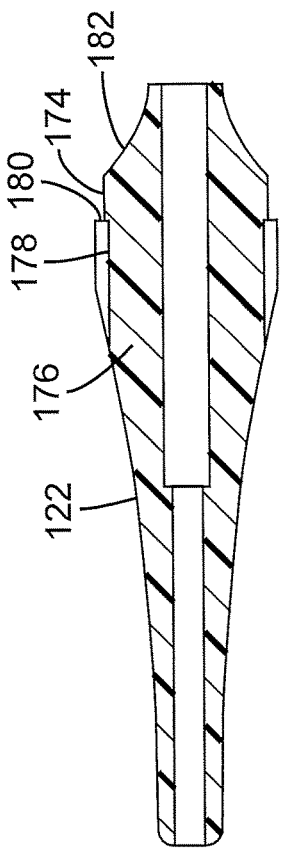
FIG. 17A is an enlarged, cross-sectional view of the nose cone of the catheter shown FIG. 17.

FIG. 17 shows an enlarged view of the nose cone 122 secured to the distal end of the innermost shaft 120. The nose cone 122 in the illustrated embodiment includes a proximal end portion 174 that is sized to fit inside the distal end of the sheath 106. An intermediate section 176 of the nose cone is positioned immediately adjacent the end of the sheath in use and is formed with a plurality of longitudinal grooves, or recessed portions, 178. The diameter of the intermediate section 176 at its proximal end 180 desirably is slightly larger than the outer diameter of the sheath 106. The proximal end 180 can be held in close contact with the distal end of the sheath 106 to protect surrounding tissue from coming into contact with the metal edge of the sheath. The grooves 178 allow the intermediate section to be compressed radially as the delivery apparatus is advanced through an introducer sheath. This allows the nose cone to be slightly oversized relative to the inner diameter of the introducer sheath. FIG. 17B shows a cross-section the nose cone 122 and the sheath 106 in a delivery position with the prosthetic valve retained in a compressed delivery state inside the sheath 106 (for purposes of illustration, only the stent 12 of the prosthetic valve is shown). As shown, the proximal end 180 of the intermediate section 176 can abut the distal end of the sheath 106 and a tapered proximal surface 182 of the nose cone can extend within a distal portion of the stent 12.

As noted above, the delivery apparatus 100 can include a valve-retaining mechanism 114 (FIG. 8B) for releasably retaining a stent 12 of a prosthetic valve. The valve-retaining mechanism 114 can include a first valve-securement component in the form of an outer fork 130 (as best shown in FIG. 12) (also referred to as an "outer trident" or "release trident"), and a second valve-securement component in the form of an inner fork 132 (as best shown in FIG. 17) (also referred to as an "inner trident" or "locking trident"). The outer fork 130 cooperates with the inner fork 132 to form a releasably connection with the retaining arms 30 of the stent 12.

The proximal end of the outer fork 130 is connected to the distal segment 126 of the outer shaft 104 and the distal end of the outer fork is releasably connected to the stent 12. In the illustrated embodiment, the outer fork 130 and the distal segment 126 can be integrally formed as a single component (e.g., the outer fork and the distal segment can be laser cut or otherwise machined from a single piece of metal tubing), although these components can be separately formed and subsequently connected to each other. The inner fork 132 can be mounted on the nose catheter shaft 120 (as best shown in FIG. 17). The inner fork 132 connects the stent to the distal end portion of the nose catheter shaft 120. The nose catheter shaft 120 can be moved axially relative to the outer shaft 104 to release the prosthetic valve from the valve-retaining mechanism, as further described below.

As best shown in FIG. 12, the outer fork 130 includes a plurality of angularly-spaced prongs 134 (three in the illustrated embodiment) corresponding to the retaining arms 30 of the stent 12, which prongs extend from the distal end of distal segment 126. The distal end portion of each prong 134 includes a respective opening 140. As best shown in FIG. 17, the inner fork 132 includes a plurality of angularly-spaced prongs 136 (three in the illustrated embodiment) corresponding to the retaining arms 30 of the stent 12, which prongs extend from a base portion 138 at the proximal end of the inner fork. The base portion 138 of the inner fork is fixedly secured to the nose catheter shaft 120 (e.g., with a suitable adhesive) to prevent axial and rotational movement of the inner fork relative to the nose catheter shaft 120.

Figure 42:
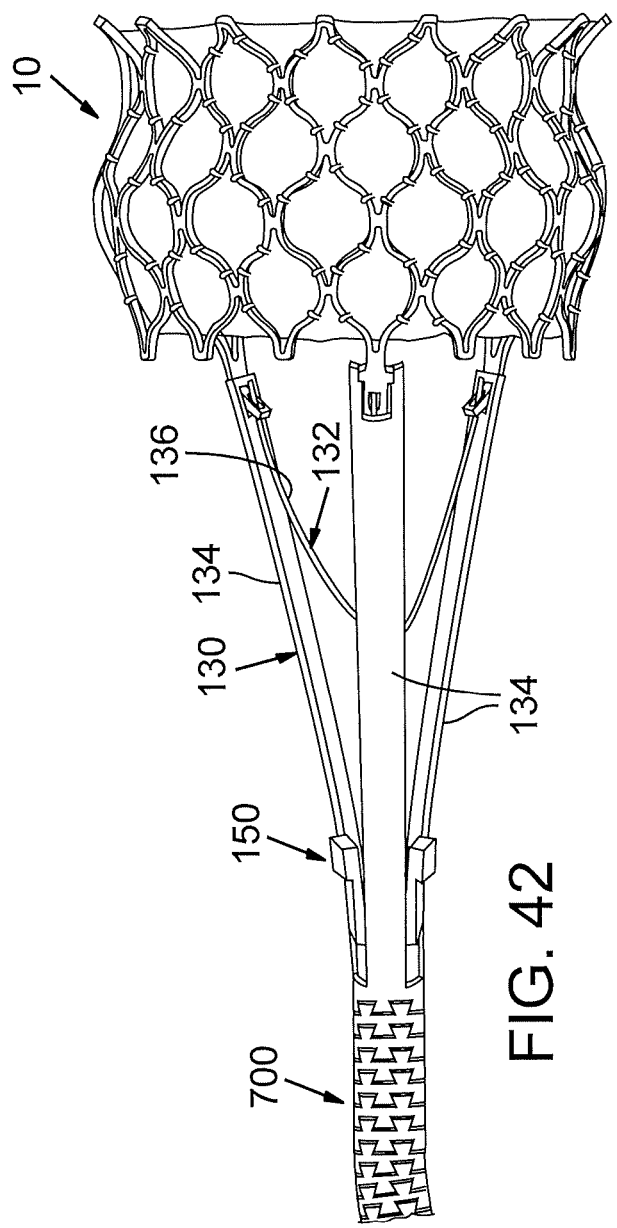

Each prong of the outer fork cooperates with a corresponding prong of the inner fork to form a releasable connection with a retaining arm 30 of the stent. In the illustrated embodiment, for example, the distal end portion of each prong 134 is formed with an opening 140. When the prosthetic valve is secured to the delivery apparatus (as best shown in FIG. 19), each retaining arm 30 of the stent 12 extends inwardly through an opening 140 of a prong 134 of the outer fork and a prong 136 of the inner fork is inserted through the opening 32 of the retaining arm 30 so as to retain the retaining arm 30 from backing out of the opening 140. FIG. 42 also shows the prosthetic valve 10 secured to the delivery apparatus by the inner and outer forks before the prosthetic valve is loaded into the sheath 106. Retracting the inner prongs 136 proximally (in the direction of arrow 184 in FIG. 20) to remove the prongs from the openings 32 is effective to release the prosthetic valve 10 from the retaining mechanism. When the inner fork 132 is moved to a proximal position (FIG. 20), the retaining arms 30 of the stent can move radially outwardly from the openings 140 in the outer fork 130 under the resiliency of the stent. In this manner, the valve-retaining mechanism 114 forms a releasable connection with the prosthetic valve that is secure enough to retain the prosthetic valve relative to the delivery apparatus to allow the user to fine tune or adjust the position of the prosthetic valve after it is deployed from the delivery sheath. When the prosthetic valve is positioned at the desired implantation site, the connection between the prosthetic valve and the retaining mechanism can be released by retracting the nose catheter shaft 120 relative to the outer shaft 104 (which retracts the inner fork 132 relative to the outer fork 130).

Techniques for compressing and loading the prosthetic valve 10 into the sheath 106 are described below. Once the prosthetic valve 10 is loaded in the delivery sheath 106, the delivery apparatus 100 can be inserted into the patient's body for delivery of the prosthetic valve. In one approach, the prosthetic valve can be delivered in a retrograde procedure where delivery apparatus is inserted into a femoral artery and advanced through the patient's vasculature to the heart. Prior to insertion of the delivery apparatus, an introducer sheath can be inserted into the femoral artery followed by a guide wire, which is advanced through the patient's vasculature through the aorta and into the left ventricle. The delivery apparatus 100 can then be inserted through the introducer sheath and advanced over the guide wire until the distal end portion of the delivery apparatus containing the prosthetic valve 10 is advanced to a location adjacent to or within the native aortic valve.

Thereafter, the prosthetic valve 10 can be deployed from the delivery apparatus 100 by rotating the torque shaft 110 relative to the outer shaft 104. As described below, the proximal end of the torque shaft 110 can be operatively connected to a manually rotatable handle portion or a motorized mechanism that allows the surgeon to effect rotation of the torque shaft 110 relative to the outer shaft 104. Rotation of the torque shaft 110 and the screw 112 causes the nut 150 and the sheath 106 to move in the proximal direction toward the outer shaft (FIG. 22), which deploys the prosthetic valve from the sheath. Rotation of the torque shaft 110 causes the sheath to move relative to the prosthetic valve in a precise and controlled manner as the prosthetic valve advances from the open distal end of the delivery sheath and begins to expand. Hence, unlike known delivery apparatus, as the prosthetic valve begins to advance from the delivery sheath and expand, the prosthetic valve is held against uncontrolled movement from the sheath caused by the expansion force of the prosthetic valve against the distal end of the sheath. In addition, as the sheath 106 is retracted, the prosthetic valve 10 is retained in a stationary position relative to the ends of the inner shaft 120 and the outer shaft 104 by virtue of the valve-retaining mechanism 114. As such, the prosthetic valve 10 can be held stationary relative to the target location in the body as the sheath is retracted. Moreover, after the prosthetic valve is partially advanced from the sheath, it may be desirable to retract the prosthetic valve back into the sheath, for example, to reposition the prosthetic valve or to withdraw the prosthetic valve entirely from the body. The partially deployed prosthetic valve can be retracted back into the sheath by reversing the rotation of the torque shaft, which causes the sheath 106 to advance back over the prosthetic valve in the distal direction.

In known delivery devices, the surgeon must apply push-pull forces to the shaft and/or the sheath to unsheathe the prosthetic valve. It is therefore difficult to transmit forces to the distal end of the device without distorting the shaft (e.g., compressing or stretching the shaft axially), which in turn causes uncontrolled movement of the prosthetic valve during the unsheathing process. To mitigate this effect, the shaft and/or sheath can be made more rigid, which is undesirable because the device becomes harder to steer through the vasculature. In contrast, the manner of unsheathing the prosthetic valve described above eliminates the application of push-pull forces on the shaft, as required in known devices, so that relatively high and accurate forces can be applied to the distal end of the shaft without compromising the flexibility of the device. In certain embodiments, as much as 20 lbs. of force can be transmitted to the end of the torque shaft without adversely affecting the unsheathing process. In contrast, prior art devices utilizing push-pull mechanisms typically cannot exceed about 5 lbs. of force during the unsheathing process.

After the prosthetic valve 10 is advanced from the delivery sheath and expands to its functional size (the expanded prosthetic valve 10 secured to the delivery apparatus is depicted in FIG. 42), the prosthetic valve remains connected to the delivery apparatus via the retaining mechanism 114. Consequently, after the prosthetic valve is advanced from the delivery sheath, the surgeon can reposition the prosthetic valve relative to the desired implantation position in the native valve such as by moving the delivery apparatus in the proximal and distal directions or side to side, or rotating the delivery apparatus, which causes corresponding movement of the prosthetic valve. The retaining mechanism 114 desirably provides a connection between the prosthetic valve and the delivery apparatus that is secure and rigid enough to retain the position of the prosthetic valve relative to the delivery apparatus against the flow of the blood as the position of the prosthetic valve is adjusted relative to the desired implantation position in the native valve. Once the surgeon positions the prosthetic valve at the desired implantation position in the native valve, the connection between the prosthetic valve and the delivery apparatus can be released by retracting the innermost shaft 120 in the proximal direction relative to the outer shaft 104, which is effective to retract the inner fork 132 to withdraw its prongs 136 from the openings 32 in the retaining arms 30 of the prosthetic valve (FIG. 20). Slightly retracting of the outer shaft 104 allows the outer fork 130 to back off the retaining arms 30 of the prosthetic valve, which slide outwardly through openings 140 in the outer fork to completely disconnect the prosthetic valve from the retaining mechanism 114. Thereafter, the delivery apparatus can be withdrawn from the body, leaving the prosthetic aortic valve 10 implanted within the native valve (such as shown in FIGS. 5A and 5B).

The delivery apparatus 100 has at its distal end a semi-rigid segment comprised of relatively rigid components used to transform rotation of the torque shaft into axial movement of the sheath. In particular, this semi-rigid segment in the illustrated embodiment is comprised of the prosthetic valve and the screw 112. An advantage of the delivery apparatus 100 is that the overall length of the semi-rigid segment is minimized because the nut 150 is used rather than internal threads on the outer shaft to affect translation of the sheath. The reduced length of the semi-rigid segment increases the overall flexibility along the distal end portion of the delivery catheter. Moreover, the length and location of the semi-rigid segment remains constant because the torque shaft does not translate axially relative to the outer shaft. As such, the curved shape of the delivery catheter can be maintained during valve deployment, which improves the stability of the deployment. A further benefit of the delivery apparatus 100 is that the ring 128 prevents the transfer of axial loads (compression and tension) to the section of the torque shaft 110 that is distal to the ring.

In an alternative embodiment, the delivery apparatus can be adapted to deliver a balloon-expandable prosthetic valve. As described above, the valve retaining mechanism 114 can be used to secure the prosthetic valve to the end of the delivery apparatus. Since the stent of the prosthetic valve is not self-expanding, the sheath 106 can be optional. The retaining mechanism 114 enhances the pushability of the delivery apparatus and prosthetic valve assembly through an introducer sheath.

FIGS. 23-26 illustrate the proximal end portion of the delivery apparatus 100, according to one embodiment. The delivery apparatus 100 can comprise a handle 202 that is configured to be releasably connectable to the proximal end portion of a catheter assembly 204 comprising catheters 102, 108, 118. It may be desirable to disconnect the handle 202 from the catheter assembly 204 for various reasons. For example, disconnecting the handle can allow another device to be slid over the catheter assembly, such as a valve-retrieval device or a device to assist in steering the catheter assembly. It should be noted that any of the features of the handle 202 and the catheter assembly 204 can be implemented in any of the embodiments of the delivery apparatuses disclosed herein.

FIGS. 23 and 24 show the proximal end portion of the catheter assembly 204 partially inserted into a distal opening of the handle 202. The proximal end portion of the main shaft 104 is formed with an annular groove 212 (as best shown in FIG. 24) that cooperates with a holding mechanism, or latch mechanism, 214 inside the handle. When the proximal end portion of the catheter assembly is fully inserted into the handle, as shown in FIGS. 25 and 26, an engaging portion 216 of the holding mechanism 214 extends at least partially into the groove 212. One side of the holding mechanism 214 is connected to a button 218 that extends through the housing of the handle. The opposite side of the holding mechanism 214 is contacted by a spring 220 that biases the holding mechanism to a position engaging the main shaft 104 at the groove 212. The engagement of the holding mechanism 214 within the groove 212 prevents axial separation of the catheter assembly from the handle. The catheter assembly can be released from the handle by depressing button 218, which moves the holding mechanism 214 from locking engagement with the main shaft. Furthermore, the main shaft 104 can be formed with a flat surface portion within the groove 212. The flat surface portion is positioned against a corresponding flat surface portion of the engaging portion 216. This engagement holds the main shaft 104 stationary relative to the torque shaft 110 as the torque shaft is rotated during valve deployment.

Figure 15:
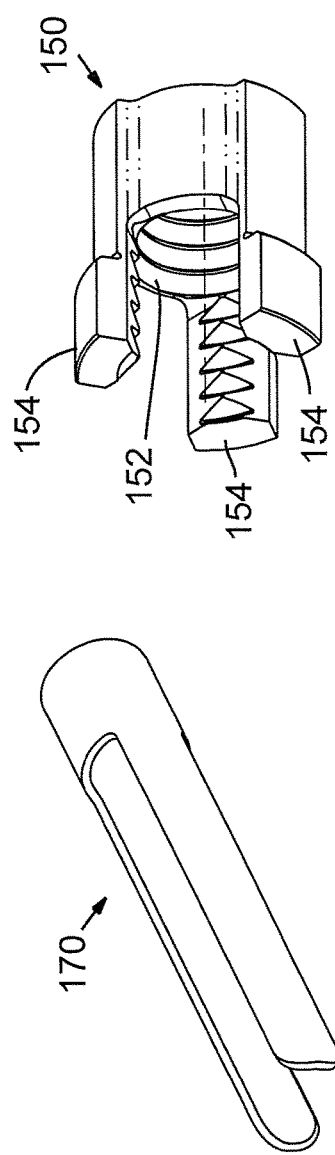
FIG. 15 is an enlarged perspective view of a coupling member disposed at the end of the torque shaft.

The proximal end portion of the torque shaft 110 can have a driven nut 222 (FIG. 26) that is slidably received in a drive cylinder 224 (FIG. 25) mounted inside the handle. The nut 222 can be secured to the proximal end of the torque shaft 100 by securing the nut 222 over a coupling member 170 (FIG. 15). FIG. 26 is a perspective view of the inside of the handle 202 with the drive cylinder and other components removed to show the driven nut and other components positioned within the drive cylinder. The cylinder 224 has a through opening (or lumen) extending the length of the cylinder that is shaped to correspond to the flats of the nut 222 such that rotation of the drive cylinder is effective to rotate the nut 222 and the torque shaft 110. The drive cylinder can have an enlarged distal end portion 236 that can house one or more seals (e.g., o-rings 246) that form a seal with the outer surface of the main shaft 104 (FIG. 25). The handle can also house a fitting 238 that has a flush port in communication with the lumen of the torque shaft and/or the lumen of the main shaft.

The drive cylinder 224 is operatively connected to an electric motor 226 through gears 228 and 230. The handle can also house a battery compartment 232 that contains batteries for powering the motor 226. Rotation of the motor in one direction causes the torque shaft 110 to rotate, which in turn causes the sheath 106 to retract and uncover a prosthetic valve at the distal end of the catheter assembly. Rotation of the motor in the opposite direction causes the torque shaft to rotate in an opposite direction, which causes the sheath to move back over the prosthetic valve. An operator button 234 on the handle allows a user to activate the motor, which can be rotated in either direction to un-sheath a prosthetic valve or retrieve an expanded or partially expanded prosthetic valve.

As described above, the distal end portion of the nose catheter shaft 120 can be secured to an inner fork 132 that is moved relative to an outer fork 130 to release a prosthetic valve secured to the end of the delivery apparatus. Movement of the shaft 120 relative to the main shaft 104 (which secures the outer fork 130) can be affected by a proximal end portion 240 of the handle that is slidable relative to the main housing 244. The end portion 240 is operatively connected to the shaft 120 such that movement of the end portion 240 is effective to translate the shaft 120 axially relative to the main shaft 104 (causing a prosthetic valve to be released from the inner and outer forks). The end portion 240 can have flexible side panels 242 on opposite sides of the handle that are normally biased outwardly in a locked position to retain the end portion relative to the main housing 244. During deployment of the prosthetic valve, the user can depress the side panels 242, which disengage from corresponding features in the housing and allow the end portion 240 to be pulled proximally relative to the main housing, which causes corresponding axial movement of the shaft 120 relative to the main shaft. Proximal movement of the shaft 120 causes the prongs 136 of the inner fork 132 to disengage from the apertures 32 in the stent 12, which in turn allows the retaining arms 30 of the stent to deflect radially outwardly from the openings 140 in the prongs 134 of the outer fork 130, thereby releasing the prosthetic valve.

FIG. 27 shows an alternative embodiment of a motor, indicated at 400, that can be used to drive a torque shaft (e.g., torque shaft 110). In this embodiment, a catheter assembly can be connected directly to one end of a shaft 402 of the motor, without gearing. The shaft 402 includes a lumen that allows for passage of an innermost shaft (e.g., shaft 120) of the catheter assembly, a guide wire, and/or fluids for flushing the lumens of the catheter assembly.

Alternatively, the power source for rotating the torque shaft 110 can be a hydraulic power source (e.g., hydraulic pump) or pneumatic (air-operated) power source that is configured to rotate the torque shaft. In another embodiment, the handle can have a manually movable lever or wheel that is operable to rotate the torque shaft 110.

In another embodiment, a power source (e.g., an electric, hydraulic, or pneumatic power source) can be operatively connected to a shaft, which is turn is connected to a prosthetic valve 10. The power source is configured to reciprocate the shaft longitudinally in the distal direction relative to a valve sheath in a precise and controlled manner in order to advance the prosthetic valve from the sheath. Alternatively, the power source can be operatively connected to the sheath in order to reciprocate the sheath longitudinally in the proximal direction relative to the prosthetic valve to deploy the prosthetic valve from the sheath.

Figure 36:
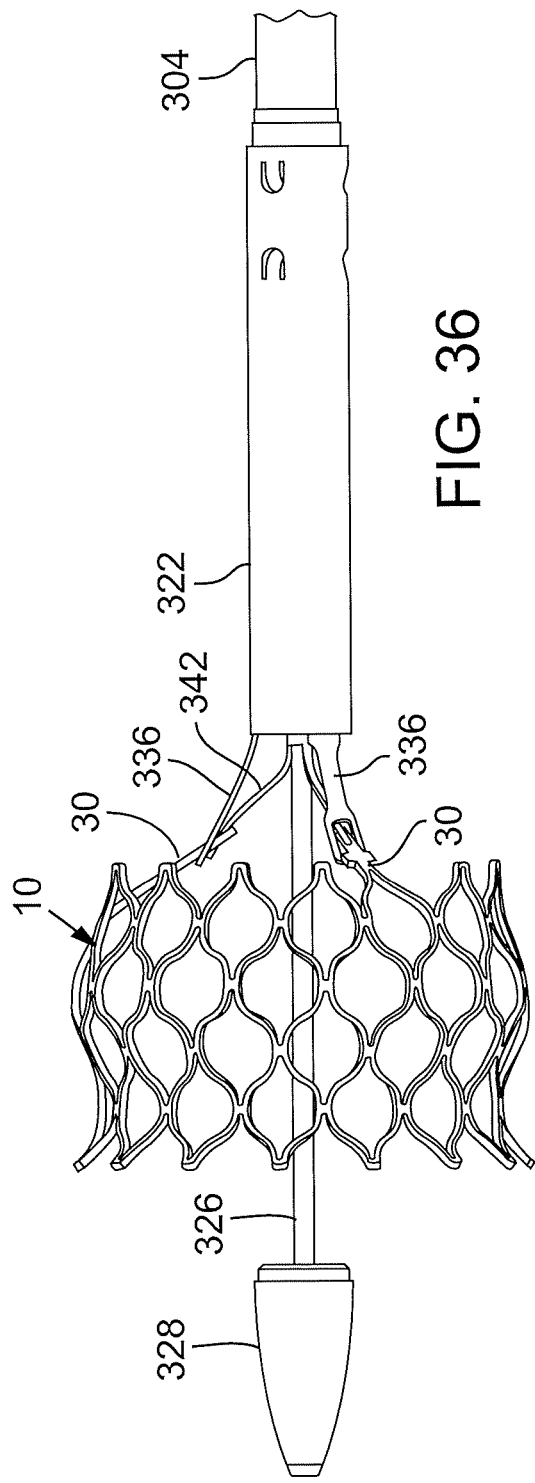
FIG. 36 is a side view illustrating the deployment of a prosthetic valve from the sheath of the delivery apparatus of FIG. 30.
Figure 37:
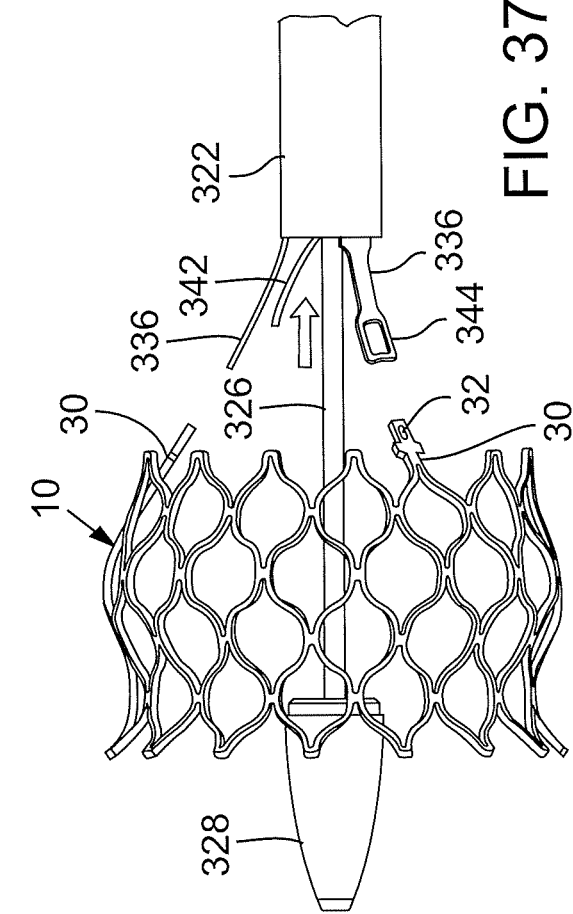
FIG. 37 is a side view illustrating the operation of the valve-retaining mechanism of the delivery apparatus of FIG. 30.

FIGS. 30-37 illustrate a delivery apparatus 300, according to another embodiment. FIGS. 30-33 show the distal end portion of the delivery apparatus 300. FIGS. 34-35 show the proximal end portion of the delivery apparatus 300. FIGS. 36-37 show the deployment of a prosthetic valve 10 from the delivery apparatus 300 (the leaflets of the prosthetic valve are removed for clarify in the figures).

The delivery apparatus 300 comprises a first, outer catheter 302 having an elongated shaft 304 extending between a valve retaining mechanism 306 at the distal end of the apparatus (FIGS. 32 and 33) and a handle portion 308 at the proximal end of the apparatus (FIGS. 34 and 35). The distal end of the main catheter shaft 304 is coupled to the valve-retaining mechanism 306, which in turn is secured to the prosthetic valve 10. The outer catheter 302 can be a guide catheter that is configured to permit selective bending or flexing of a portion of the shaft 304 to facilitate advancement of the delivery apparatus through the patient's vasculature.

The delivery apparatus also includes a second, torque catheter 310 having an elongated torque shaft 312 that extends through the main catheter shaft 304. The distal end of the torque shaft 304 is connected to a flexible screw mechanism 314 comprising a flexible shaft 316 extending through the retaining mechanism 306 and one or more screw members 318 spaced along the length of the shaft 316 (FIGS. 32 and 33). As shown in FIG. 33, the shaft 316 of the screw mechanism 314 exhibits sufficient flexibility to permit bending or flexing to assist in tracking the delivery apparatus through the patient's vasculature. The main catheter shaft 304 can be formed with internal threads that engage the external threads of the screw members 318. For example, a distal end portion of the main shaft 304 (e.g., an 11-mm segment at the distal end of the shaft 304) can be formed with internal threads. The proximal end portion of the torque shaft 312 extends into the handle portion 308 where it is coupled to a control knob 320 to permit rotation of the torque shaft relative to the main catheter shaft 304 (FIGS. 34 and 35), as further described below.

In operation, each screw member 318 passes through and engages the internally threaded portion of the main shaft 304. The screw members 318 desirably are spaced from each other such that a screw member 318 can engage one end of the internally threaded portion of the main shaft 304 before an adjacent screw member 318 disengages from the other end of the internally threaded portion of the main shaft as the screw members pass through the internally threaded portion so as to prevent or at least minimize application of axially directed forces on the torque shaft. In this manner, relatively high unsheathing forces can be applied to the sheath without compromising the overall flexibility of the delivery apparatus.

The delivery apparatus can also include a third, nose catheter 324 having an elongated shaft 326 that is connected at its distal end to a nose piece 328. The nose catheter shaft 326 extends through the torque shaft 312 and has a proximal end portion that extends outwardly from the proximal end of the handle portion 308 (FIGS. 34 and 35). The main catheter shaft 304, the torque shaft 312, and the nose catheter shaft 326 desirably are configured to be moveable axially relative to each other.

As shown in FIGS. 30 and 31, the delivery apparatus can further include a movable sheath 322 that extends over the compressed prosthetic valve 10. The sheath 322 is connected to screw mechanism 314 so that longitudinal movement of the torque shaft 312 and the screw mechanism 314 causes corresponding longitudinal movement of the sheath 322. For example, the sheath can have inwardly extending prongs 358 (FIG. 31) extending into respective apertures 360 of fingers 362 (FIG. 32), which in turn are connected to the distal end of the flexible shaft 316. Fingers 362 desirably are connected to the shaft 316 by a swivel joint that pushes or pulls fingers 362 when the shaft 316 moves distally or proximally, respective, yet allows the shaft 316 to rotate relative to the fingers 362. Consequently, rotation of the torque shaft 312 and the screw mechanism 314 relative to the main shaft 304 is effective to cause the sheath 322 to move in the proximal and distal directions (as indicated by double-headed arrow 330 in FIG. 30) relative to the prosthetic valve to permit controlled deployment of the prosthetic valve from the sheath, as further described below.

Referring to FIGS. 32 and 33, the valve-retaining mechanism 306 comprises an outer fork 330 and an inner fork 332. A portion of the finger 362 is cut away in FIG. 33 to show the inner fork 332. The outer fork 330 comprises a head portion 334 and a plurality of elongated, flexible prongs 336 (three in the illustrated embodiment) extending from the head portion 334. The head portion 334 can be formed with resilient retaining flanges 338 to permit the outer fork to form a snap-fit connection with a stepped shaft portion of the main catheter shaft 304, as described above. The inner fork 332 has a head portion 340 that is fixedly secured to the nose catheter shaft 326 and a plurality of elongated prongs 342 extending from the head portion 340. The distal end portions of the prongs 336 of the outer fork can be formed with apertures 344 sized to receive respective retaining arms 30 of the prosthetic valve 10. The distal ends of the prongs 342 of the inner fork 332 extend through the apertures 32 in the retaining arms 30 to form a releasable connection for securing the prosthetic valve 10, similar to valve-retaining mechanism 114 described above and shown in FIGS. 19-20. After the prosthetic valve is deployed form the sheath 322, the connection between the prosthetic valve and the retaining mechanism 306 can be released by retracting the nose catheter shaft 326 relative to the main catheter shaft 304 to withdrawn the prongs 342 from the apertures 32 in the retaining arms 30. The outer prongs 336 and the shaft 316 of the screw mechanism 314 exhibit sufficient flexibility to allow that portion of the delivery apparatus to bend or flex as the delivery apparatus is advanced through the patient's vasculature to the implantation site, yet are rigid enough to permit repositioning of the prosthetic valve after it is deployed from the sheath 322. The outer fork 330, including prongs 336, can be made from any of various suitable materials, such as metals (e.g., stainless steel) or polymers, that provide the desired flexibility.

Referring to FIGS. 34 and 35, the handle portion 308 comprises a housing 346 that houses a first gear 348 and a second gear 350. The first gear 348 has a shaft that extends through the housing and is connected to the control knob 320 located on the outside of the housing. The second gear 350 is disposed on and fixedly secured to the torque shaft 312. Thus, manual rotation of the control knob 320 causes rotation of the first gear 348, which in turn rotates the second gear 350. The second gear 350 rotates the torque shaft 312 and the screw mechanism 314 relative to the main catheter shaft 304, the valve-retaining mechanism 306, and the prosthetic valve 10. Rotation of the torque shaft 312 and the screw mechanism 314 in turn causes linear movement of the sheath 322 relative to the prosthetic valve.

In use, the prosthetic valve 10 is loaded into the sheath 322 in a radially compressed state (as depicted in FIG. 30), which can be accomplished, for example, by using one of the loading cones described below. The delivery apparatus 300 is then inserted into the patient's vasculature and advanced to a position at or adjacent the implantation site. The prosthetic valve 10 can then be deployed from the sheath by rotating the knob 320 on the handle portion, which in turn causes the torque shaft 312 and the screw mechanism 316 to retract within the main shaft 304, causing the sheath 322 to move in the proximal direction (arrow 352 in FIG. 31) to expose the prosthetic valve, as depicted in FIG. 31. Rotation of the knob 320 enables a controlled and precise retraction of the sheath 322 during valve deployment. Advantageously, the sheath is retracted while the position of the prosthetic valve can be held constant relative to the annulus at the implantation site during the unsheathing process. Rotation of the knob in the opposite direction causes the sheath to move in the distal direction to again cover the prosthetic valve. Thus, after the prosthetic valve has been at least partially advanced from the sheath, it is possible to reverse rotation of the knob to bring the prosthetic valve back into the sheath in a compressed state if it becomes necessary to reposition the delivery apparatus within the body or to completely withdraw the delivery apparatus and the prosthetic valve from the body.

After the prosthetic valve 10 is advanced from the delivery sheath and expands to its functional size (as shown in FIG. 36), the prosthetic valve remains connected to the delivery apparatus via the retaining mechanism 306. Consequently, after the prosthetic valve is advanced from the delivery sheath, the surgeon can reposition the prosthetic valve relative to the desired implantation position in the native valve such as by moving the delivery apparatus in the proximal and distal directions or side to side, or rotating the delivery apparatus, which causes corresponding movement of the prosthetic valve. The retaining mechanism 306 desirably provides a connection between the prosthetic valve and the delivery apparatus that is secure and rigid enough to retain the position of the prosthetic valve relative to the delivery apparatus against the flow of the blood as the position of the prosthetic valve is adjusted relative to the desired implantation position in the native valve. Once the surgeon positions the prosthetic valve at the desired implantation position in the native valve, the surgeon can release the connection between the prosthetic valve and the delivery apparatus by pulling the proximal end 354 of the nose catheter shaft 326 in the proximal direction (as indicated by arrow 356 in FIG. 34) relative to the main catheter shaft 304, which is effective to retract the inner fork 332 to withdraw its prongs 342 from the openings 32 in the retaining arms 30 of the prosthetic valve (FIG. 37). Retraction of the main catheter shaft 304 retracts the outer fork 330 to completely disconnect the prosthetic valve from the retaining mechanism 306 (as shown in FIG. 37). Thereafter, the retaining mechanism can be retraced back into the sheath 322, the delivery apparatus can be withdrawn from the body, leaving the prosthetic valve implanted within the native valve (such as shown in FIGS. 5A and 5B).

Because the prongs 134 of the outer fork 130 (and the prongs 336 of the outer fork 330) are relatively long and add to the rigidity of the semi-rigid segment discussed above, it is desirable to form the prongs 134 as thin as possible. However, relatively thinner prongs, although more flexible, can be more susceptible to collapse if they are subjected to compression and bending loads. To maximize the flexibility of the prongs while maintaining functionality during loading, the prongs of the outer fork can be pre-bent inwardly or outwardly. FIG. 38, for example, show an example of an outer fork 500 that has a similar construction to the outer fork 130 except that the former has a plurality of prongs 502 that are pre-bent radially inwardly toward the torque shaft at about the middle of the prongs. Thus, under compression loading, the prongs can bend inwardly in a controlled manner and are supported by the torque shaft and/or screw (that extends through the outer fork) to maintain the column strength of the prongs. FIG. 39 shows another embodiment of an outer fork 600 that has a plurality of prongs 602 that are pre-bent radially outwardly. An outer sheath (not shown), which can be a proximal extension of a sheath 106 that covers the prosthetic valve, can extend over the prongs 602. Under compression loading, the prongs 602 can bend outwardly and contact the sheath to maintain column strength.

FIG. 40 shows a torque shaft 700 (also referred to as a "necklace" shaft due to its construction that resembles a necklace), according to another embodiment, that can be used in the any of the delivery apparatuses disclosed herein. As shown, the torque shaft 700 comprises one or more sections 701 that comprise a plurality of annular metal links 702 connected to each other in series. Each link 702 comprises a generally circular band having alternating distally extending legs 704 and proximally extending legs 706. The gap between adjacent legs forms a receiving space for receiving a leg of an adjacent link. In the illustrated embodiment, each leg 704, 706 and receiving space has a generally trapezoidal shape, although other shapes can be used. The connection between adjacent links allows the torque shaft to bend in any direction and allows torque to be transmitted along the length of the shaft. FIG. 41 shows a cut pattern for forming the links of the torque shaft. The shaft can be formed by laser cutting the links in a metal tube. Post-cutting etching can be used to widen the gaps between adjacent legs 704, 706 to achieve the desired flexibility of the shaft.

In the embodiment shown in FIG. 40, the torque shaft 700 comprises a distal segment 701a and a proximal segment 701b comprised of a plurality of interconnected links. The illustrated shaft 700 also includes an intermediate section 710 comprising a plurality of slots or gaps laser cut or otherwise formed in the shaft, similar to the distal segment 126 of the outer shaft 104. It should be appreciated that the entire length or substantially the entire length of the torque shaft (from the handle to the screw 112) can be formed from a plurality of interconnected links 702. In alternative embodiments, selected portions of the torque shaft can be formed from interconnected metal links that are connected to portions of the torque shaft that are comprised of one or more polymeric layers.

Figure 43:
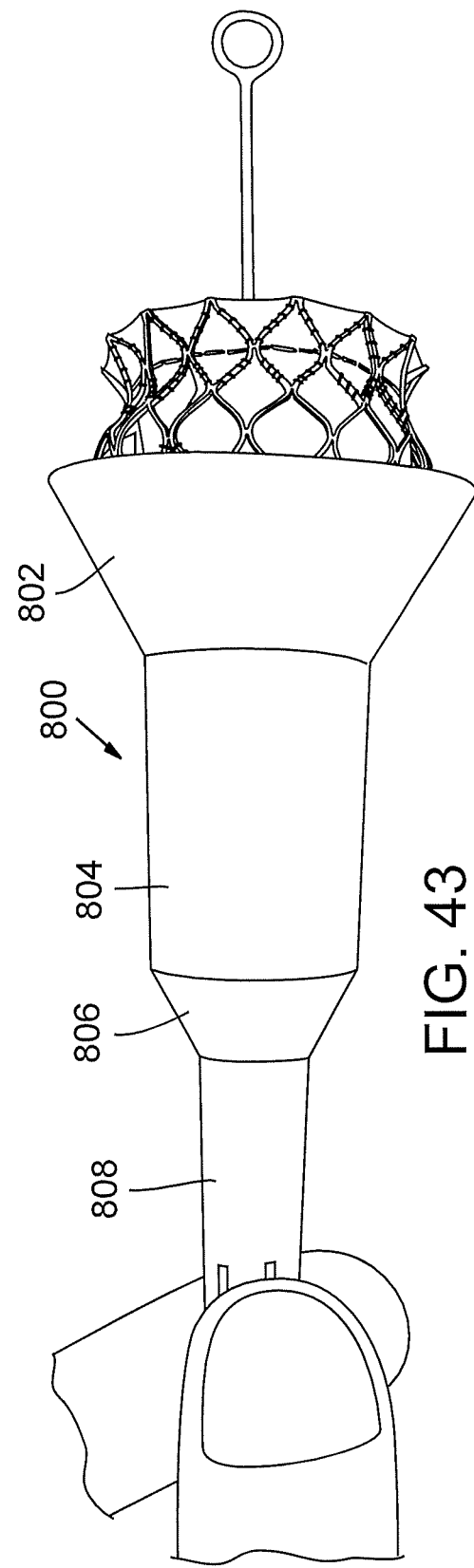

Turning now to FIG. 42, there is shown a prosthetic valve 10 secured to the distal end of a catheter assembly via a valve-retaining mechanism including an outer fork 130 and an inner fork 132. The threaded nut 150 can be seen positioned between the prongs of the outer fork 130. The prosthetic valve 10 is ready to be compressed and loaded into the sheath 106 of a delivery apparatus. FIGS. 43-45 illustrate one embodiment of a loading cone, indicated at 800, and a method for loading the prosthetic valve 10 into the sheath 106 using the loading cone 800.

As shown, the loading cone 800 in the illustrated embodiment has a conical first section 802, an elongated cylindrical second section 804, a relatively short conical third section 806, and an elongated conical fourth section 808. The first section defines the inlet opening of the loading cone while the fourth section defines the outlet opening of the loading cone. The fourth section 808 can be formed with a plurality of axial slits that define flexible legs 810 at the outlet opening of the loading cone.

In use, the proximal end of the catheter assembly is inserted into the inlet opening and pulled through the outlet opening of the loading cone so as to place the prosthetic valve partially in the first section 802, as depicted in FIG. 43. The catheter assembly is then further pulled to pull the prosthetic valve into the second section 804 to partially compress the prosthetic valve. At this point, the user can visually inspect the valve leaflets, valve skirt, the valve-retaining mechanism, and other components and make any adjustments before final compression of the prosthetic valve. For example, the user can remove any folds in the valve leaflets or skirt to minimize damage to these components when the prosthetic valve is fully compressed and to ensure the prosthetic valve is further compressed in an even and predictable manner.

After making any adjustments, the prosthetic valve can be pulled through the third section 806 into the fourth section 808, which compresses the prosthetic valve close to its final compressed size, until the threaded nut 150 is pulled outwardly from the outlet of the loading cone, as depicted in FIG. 44. The flexible legs 810 can expand as the nut 150 is being pulled through the outlet of the loading cone. The third section 806 serves as a transition region that facilitates movement of the prosthetic valve from the second section into the fourth section. At this point, the sheath 106 (positioned outside the cone 800 and to the left of the nut 150 in the figures) can be connected to the threaded nut 150 by sliding the sheath onto the nut until the raised leg portions 154 of the nut snap into corresponding openings 172 in the sheath 106. As shown in FIG. 45, a ring 814 can then be placed over the legs 810 at the outlet of the loading cone to ensure that the diameter of the outlet remains slightly smaller than the inner diameter of the sheath 106 when the prosthetic valve is pulled out of the loading cone and into the sheath. Finally, the distal end of the sheath 106 can be placed against the outlet of the loading cone and the fully compressed prosthetic valve can be pulled into the sheath.

FIG. 46 shows another embodiment of a loading cone, indicated at 900. The loading cone 900 is similar to the loading cone 800 but has more gradual transitions between the different sections of the loading cone.

Figure 48:
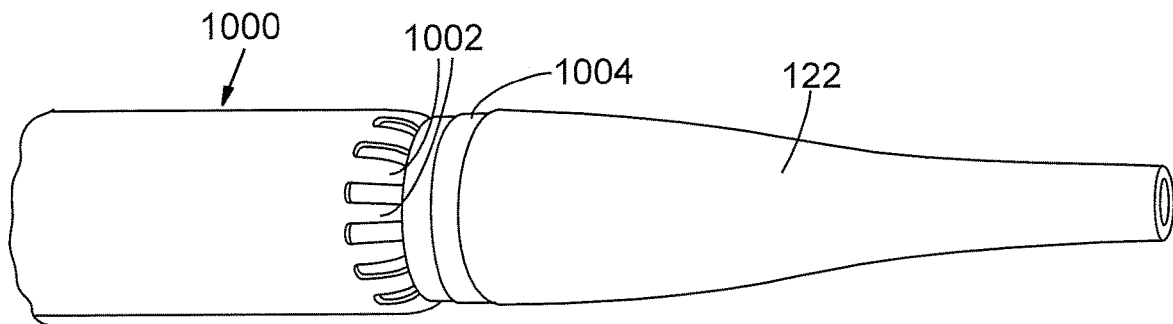
Figure 49:
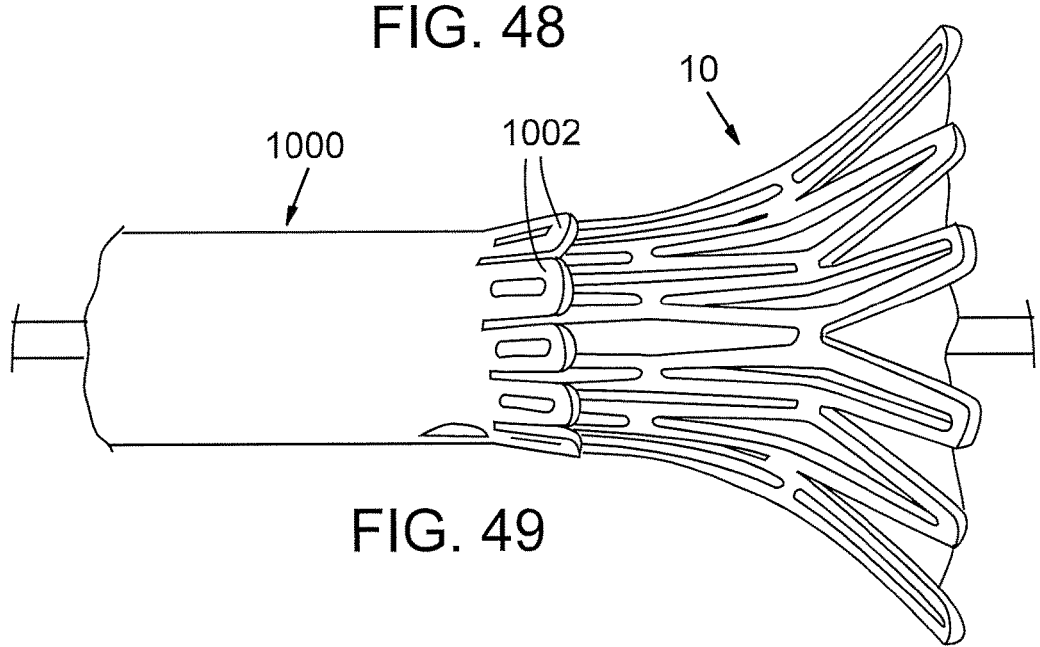
FIG. 49 shows the deployment of a prosthetic valve from the sheath shown in FIGS. 47-48.

FIGS. 47 and 48 show an alternative embodiment of a sheath, indicated at 1000. The sheath 1000 can have a construction similar to the sheath 106 previously described, except that the sheath 1000 has a plurality of circumferentially spaced, flexible flaps 1002 at its distal end. The flaps 1002 desirably are biased inwardly (as shown in FIG. 48) and can expand radially outwardly when a prosthetic valve is deployed through the distal opening of the sheath (FIG. 49). FIG. 48 shows the distal end of the sheath 1000 abutting the end of a nose cone 122 for delivery through a patient's vasculature. The nose cone 122 in this embodiment can have a reinforcing ring 1004 at its proximal end. As the delivery catheter is advanced through the patient's vasculature, the flaps 1002 serve as an atraumatic transition region between the end of the sheath and the nose cone to help prevent damage to surrounding tissue that might otherwise occur from contact with the distal end of the sheath.

Figure 50:
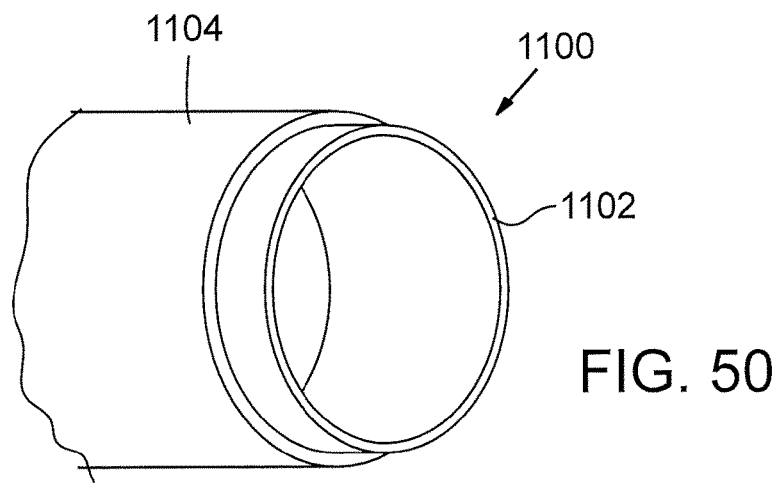
FIG. 50 is a perspective view of another embodiment of a sheath of a delivery apparatus.

FIG. 50 shows another embodiment of a delivery sheath, indicated at 1100. Instead of having distal flaps, the sheath 1100 includes a flexible polymeric sleeve 1102 that is bonded to the inner surface of an outer, cylindrical metal tube 1104 and extends outwardly from the distal end of the metal tube 1104. The sleeve 1102 can made of polyethylene terephthalate (PET) or similar polymeric materials. The sleeve 1102 serves as an atraumatic transition between the sheath and a nose cone that protects surrounding tissue from contacting the metal edge of the sheath. Also, because the sleeve 1102 prevents direct contact between the prosthetic valve and the distal edge of the sheath, the sleeve 1102 reduces sliding friction on the prosthetic valve. As a result, significantly less force is needed retrieve the prosthetic valve after it is deployed from the sheath (i.e., the force required to slide the sheath back over the prosthetic valve after it is deployed in the patient). In some cases it may be necessary to re-track the distal end of the delivery apparatus for proper valve positioning, which may involve withdrawing the distal end of the delivery apparatus from the diseased valve (e.g., withdrawing the distal end back into the aorta) and then advancing the delivery apparatus back into the diseased valve. The sleeve 1102 protects surrounding tissue from contacting the metal edge of the sheath, especially when re-crossing the diseased valve.

Figure 51:
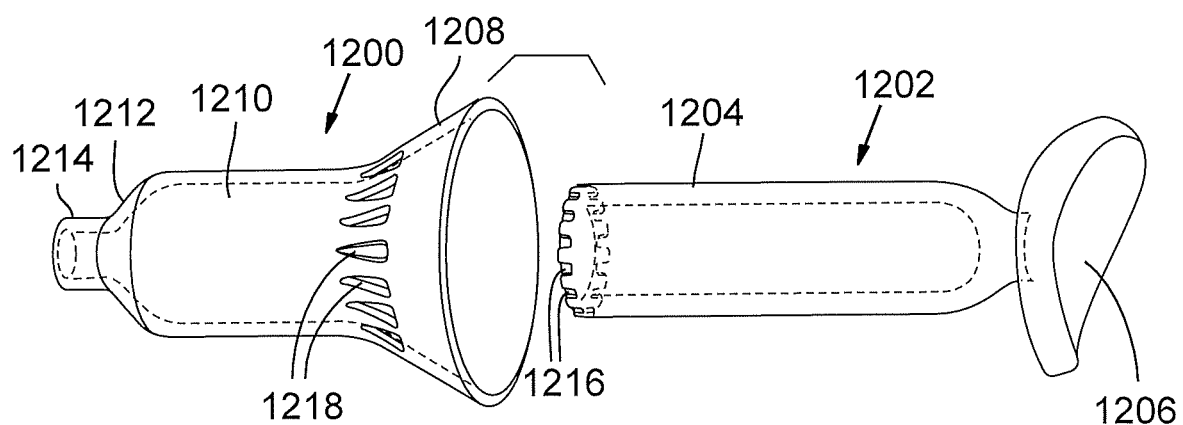
FIG. 51 is a perspective view of a loading cone and plunger assembly for loading a prosthetic valve into a delivery sheath, according to another embodiment.

FIG. 51 shows a loading cone and plunger assembly for loading a prosthetic valve into the sheath of a delivery apparatus, according to another embodiment. The assembly comprises a loading cone 1200 and a plunger 1202 that comprises an elongated shaft 1204 and a handle 1206. The loading cone 1200 in the illustrated embodiment includes a conical first section 1208 defining in the inlet of the loading cone, a cylindrical second section 1210, a conical third section 1212 and a cylindrical fourth section 1214 defining the outlet of the loading cone. In an alternative embodiment (FIG. 52), the loading cone does not have a fourth section 1214 and the outlet opening is provided at the end of tapered third section 1212.

The shaft 1204 has a diameter that is slightly smaller than the inner diameter of the second section 1210 to allow the shaft to slide easily into the second section. Also, the shaft is sized such that its outer diameter is equal to diameter of the valve stent 12 when the stent is in a partially compressed state within the second section 1210 of the loading cone. The distal end of the shaft 1204 is formed with a plurality of circumferentially spaced recesses 1216 on its outer surface that are adapted to receive the apexes of the stent at its inflow end 26 when the stent is partially compressed. Located on the inner surface of the loading cone are a plurality of circumferentially spaced ribs 1218 that can extend partially along the inner surface of the first section 1208 and partially along the inner surface of the second section 1210. The ribs 1218 are adapted to extend partially into the cells of the stent 12 as the stent is urged into the second section 1210. In this manner, the ribs 1218 can prevent the leaflets or skirt of the prosthetic valve from projecting outwardly through the cells of the stent as it is being compressed inside the loading cone, and therefore protect the leaflets and skirt from being pinched by the metal struts 16 of the stent.

In use, a prosthetic valve (e.g., prosthetic valve 10) is mounted on a catheter assembly, the proximal end of which is pulled through the loading cone to place the prosthetic valve in the first section 1208. The prosthetic valve is then pulled into the second section 1210 to partially compress the prosthetic valve. Once the prosthetic valve is partially compressed, the plunger can be used to assist in further advancing through the prosthetic valve through the loading cone. In particular, the end of the plunger shaft is aligned axially with the prosthetic valve and the apexes of the stent are placed in recesses 1216. As the prosthetic valve is pulled through the fourth section 1214 and into a delivery sheath 106 (e.g., by pulling the catheter assembly in a direction away from the loading cone), the prosthetic valve can be simultaneously pushed through the loading cone using the plunger.

As noted above, a delivery apparatus can have a motorized handle to effect movement of the delivery sheath relative to a prosthetic valve. The motorized handle can be used to pull the prosthetic valve through the loading cone and into the delivery sheath. For example, after the catheter assembly is inserted through the loading cone, the proximal end of the catheter assembly is connected to the motorized handle. The prosthetic valve is manually pulled through the loading cone far enough to be able to secure the delivery sheath 106 to its connection at the distal end of the catheter assembly (e.g., nut 150). The motor is then activated to move the sheath distally relative to the catheter assembly and against the outlet end of the loading cone 1200, which pulls the prosthetic valve out of the loading cone and into the sheath.

FIG. 53 illustrates a delivery apparatus 1300, according to another embodiment. The delivery apparatus 1300 in this embodiment includes all of the features of the delivery apparatus 300 of FIGS. 30-33 except that it includes the torque shaft 700 shown in FIG. 40. The use of the torque shaft 700 increases the flexibility of the portion of the delivery apparatus that is positioned in the ascending aorta during valve deployment. This portion of the delivery apparatus typically is subjected to the greatest amount of bending during valve deployment. In particular embodiments, the torque shaft 700 extends from the valve-retaining mechanism to the handle of the delivery apparatus. In other embodiments, the delivery apparatus can comprise a torque shaft that has a distal segment formed from interconnected metal links 702 and a proximal segment formed from other materials (e.g., one or more layers of polymeric tubing).

FIG. 54 illustrates a delivery apparatus 1400, according to another embodiment. The delivery apparatus 1400 in this embodiment includes a torque shaft 700 that extends through an outer fork 330. A screw 1402 is positioned along the length of the torque shaft at a location proximal to the outer fork 330. An outer shaft 304 (not shown in FIG. 54) is formed with internal threads that mate with the threads of the screw 1402 to transform rotation of the torque shaft into axial translation of the sheath 322 (which is connected to the torque shaft via coupling member 362). Desirably, the screw 1402 and the internal threads of the outer shaft are at a location along the length of the torque shaft that is positioned in the descending aorta during valve deployment. The extension of the torque shaft 700 distally into the area occupied by the valve-retaining mechanism increases the overall flexibility of this portion of the delivery apparatus.

Due to the presence of gaps in the links 702 that form the torque shaft (which allows for a limited amount of axial movement between links), the expansion force of the prosthetic valve against the distal end of the sheath 322 can cause the prosthetic valve to "jump" slightly out of the sheath as it is being deployed. To control the expansion of the prosthetic valve as it is being deployed, a spring 1404 can be co-axially mounted over the torque shaft 700. The outer shaft 304 (not shown) extends at least partially over the spring 1404. The proximal end 1406 of the spring is fixed relative to the inner surface of the outer shaft 304. The distal end of the spring 1408 is positioned to contact coupling member 362 when the torque shaft is rotated to cause the sheath 322 to move proximally during valve deployment. In this manner, the spring 1404 compresses and applies a distally directed force against the coupling member 362 and the sheath, which resists sudden movement of the sheath in the proximal direction caused by the expansion of the prosthetic valve.

Figure 55:
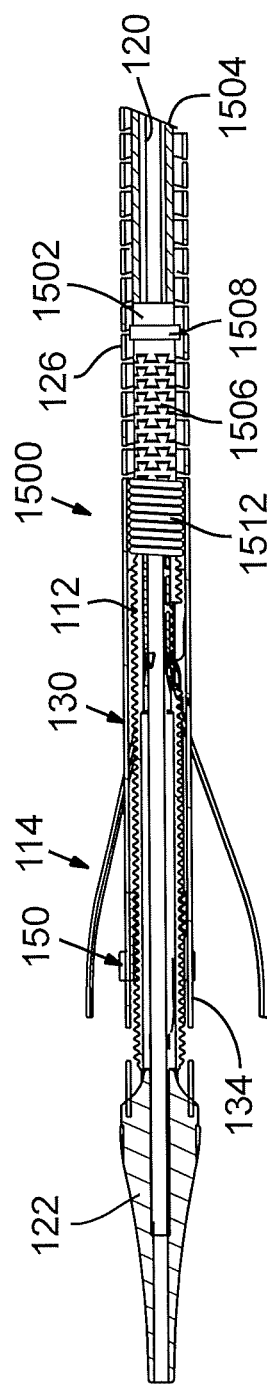

FIG. 55 shows a delivery apparatus 1500, according to another embodiment, which is a modification of the delivery apparatus. This embodiment is similar to the embodiment 1300 shown in FIG. 53 except that a ring, or anchoring disc, 1508 (similar to ring 128) is placed on the torque shaft 1502 proximal to the screws. As shown, the torque shaft 1502 can include a distal segment 1506 having the same construction of shaft 700 shown in FIG. 40 and a proximal segment 1504 that can comprise one or more layers of polymeric tubing. The ring 1508 can be mounted near the distal end of the proximal segment 1504. The ring is received by a feature formed on the inner surface of the outer shaft 126 to allow rotation of the torque shaft but prevent axial translation of the torque shaft relative to the outer shaft. A threaded nut 150 can be mounted on the screw 112 in a manner similar to that shown in FIG. 21 to transform rotation of the torque shaft into axial movement of the sheath 106. A spring 1512 can be mounted on the distal segment 1506 of the torque shaft to contact the nut 150 and minimize valve jumping during valve deployment.

Figure 56:
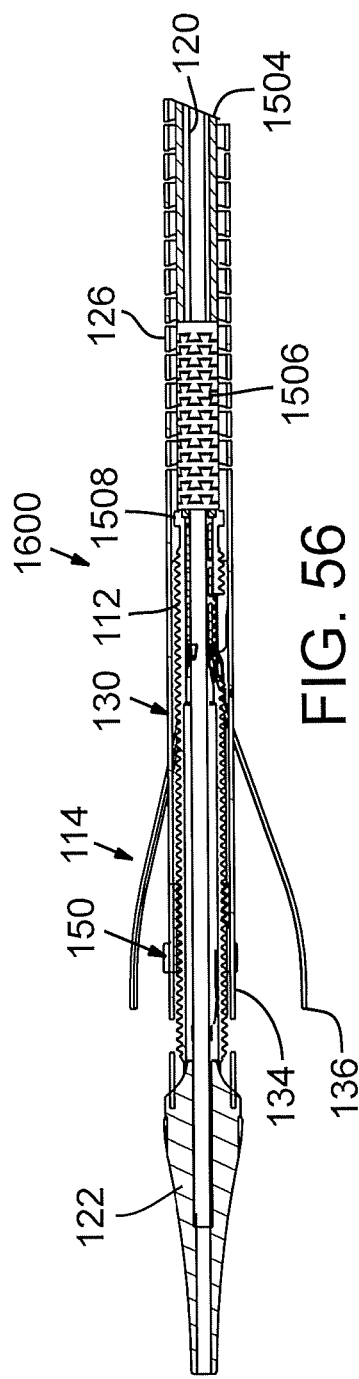

FIG. 56 shows a delivery apparatus 1600, according to another embodiment. This embodiment is similar to the embodiment 1500 shown in FIG. 55, except that the ring 1508 can be placed distal to the distal segment 1506 of the torque shaft. In the embodiment of FIG. 56, the spring 1512 can be excluded because the ring 1508 prevents the axial force of the expanding prosthetic valve from being transmitted to the links in the distal segment 1506 of the torque shaft.

Figure 57:
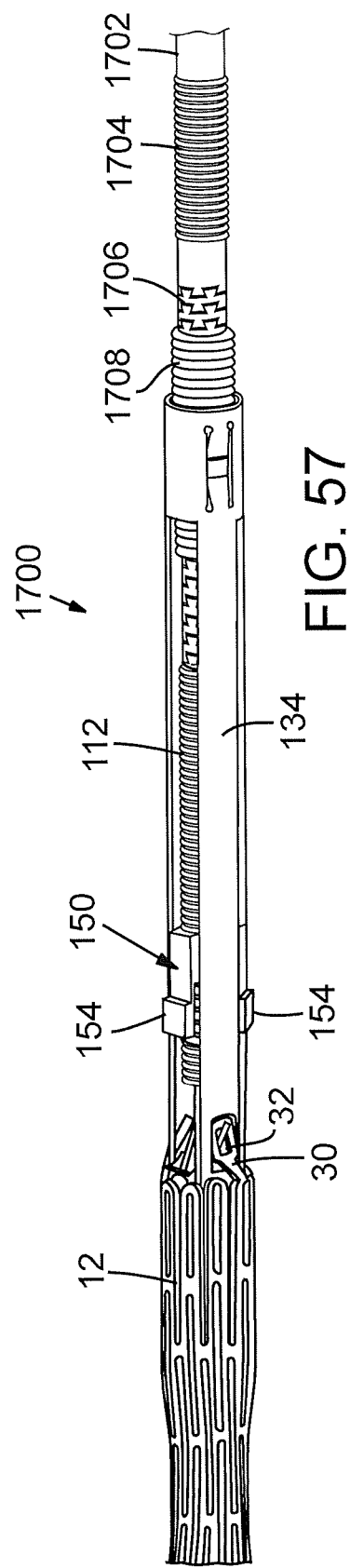

FIG. 57 shows a delivery apparatus 1700, according to another embodiment. This embodiment is similar to the embodiment 1500 shown in FIG. 55, except that it comprises a torque shaft that includes a distal segment 1706 having the same construction of shaft 700 shown in FIG. 40 and a proximal segment 1702 that includes a screw 1704 that engages internal threads on an outer shaft 104 (not shown). The distal segment 1706 extends partially into the area occupied by the outer fork 330. A spring 1708 can be mounted on the distal segment 1706 to minimize valve jumping as previously described. This embodiment allows the distal screw/screws (the screw/screws distal to the segment 1706) to rotate and translate the nut 150 while allowing the torque shaft to translate axially. This mechanism drives the nut 150 twice as fast as compared to the embodiments described above. Consequently, this embodiment can use a shorter length of screw/screws to move the nut 150, and therefore can reduce the overall length of the semi-rigid segment. Moreover, this embodiment allows the portion of the delivery apparatus occupied by the distal segment 1706 to bend during tracking of the delivery apparatus through the patient's vasculature.

Known introducer sheaths typically employ a sleeve made from polymeric tubing having a radial wall thickness of about 0.010 to 0.015 inch. FIG. 58A shows another embodiment of an introducer sheath, indicated at 2000, that employs a thin metallic tubular layer that has a much smaller wall thickness compared to known devices. In particular embodiments, the wall thickness of the sheath 2000 is about 0.0005 to about 0.002 inch. The introducer sheath 2000 includes a proximally located housing, or hub, 2002 and a distally extending sleeve, or cannula, 2004. The housing 2002 can house a seal or a series of seals as known in the art to minimize blood loss. The sleeve 2004 comprises a tubular layer 2006 that is formed from a metal or metal alloy, such as Nitinol or stainless steel, and desirably is formed with a series of circumferentially extending or helically extending slits or openings to impart a desired degree of flexibility to the sleeve.

As shown in FIG. 58B, for example, the tubular layer 2006 is formed (e.g., laser cut) with an "I-beam" pattern of alternating circular bands 2007 and openings 2008 with axially extending connecting portions 2010 connecting adjacent bands 2007. Two adjacent bands 2007 can be connected by a plurality of angularly spaced connecting portions 2010, such as four connecting portions 2010 spaced 90 degrees from each other around the axis of the sleeve, as shown in the illustrated embodiment. The sleeve 2004 exhibits sufficient flexibility to allow the sleeve to flex as it is pushed through a tortuous pathway without kinking or buckling. FIG. 59 shows another pattern of openings that can be laser cut or otherwise formed in the tubular layer 2006. The tubular layer in the embodiment of FIG. 59 has a pattern of alternating bands 2012 and openings 2014 with connecting portions 2016 connecting adjacent bands 2012 and arranged in a helical pattern along the length of the sleeve. In alternative embodiments, the pattern of bands and openings and/or the width of the bands and/or openings can vary along the length of the sleeve in order to vary stiffness of the sleeve along its length. For example, the width of the bands can decrease from the proximal end to the distal end of the sleeve to provide greater stiffness near the proximal end and greater flexibility near the distal end of the sleeve.

As shown in FIG. 60, the sleeve can have a thin outer layer 2018 extending over the tubular layer 2006 and made of a low friction material to reduce friction between the sleeve and the vessel wall into which the sleeve is inserted. The sleeve can also have a thin inner layer 2020 covering the inner surface of the tubular layer 2006 and made of a low friction material to reduce friction between the sleeve and the delivery apparatus that is inserted into the sleeve. The inner and outer layers can be made from a suitable polymer, such as PET, PTFE, and/or FEP.

In particular embodiments, the tubular layer 2006 has a radial wall thickness in the range of about 0.0005 inch to about 0.002 inch. As such, the sleeve can be provided with an outer diameter that is about 1-2 Fr smaller than known devices. The relatively smaller profile of the sleeve 2004 improves ease of use, lowers risk of patient injury via tearing of the arterial walls, and increases the potential use of minimally invasive procedures (e.g., heart valve replacement) for patients with highly calcified arteries, tortuous pathways or small vascular diameters.

In a modification of the introducer sheath 2000, the sheath can have inner and outer layers 2020, 2018, respectively, which are secured to a metal sleeve (e.g., sleeve 2004) only at the proximal and distal ends of the metal sleeve. The inner and outer polymeric layers can be bonded to the metal sleeve (or to each other through the gaps in the metal sleeve), for example using a suitable adhesive. In this manner, the metal sleeve is unattached to the inner and outer polymeric layers between the proximal and distal ends of the sleeve along the majority of the length of the sleeve, and therefore is "free-floating" relative to the polymeric layers along the majority of the length of the sleeve. This construction allows the adjacent bands of metal to bend more easily relative to the inner and outer layers, providing the sheath with greater flexibility and kink-resistance than if the inner and outer layers are bonded along the entire length of the sleeve.

Figure 61:
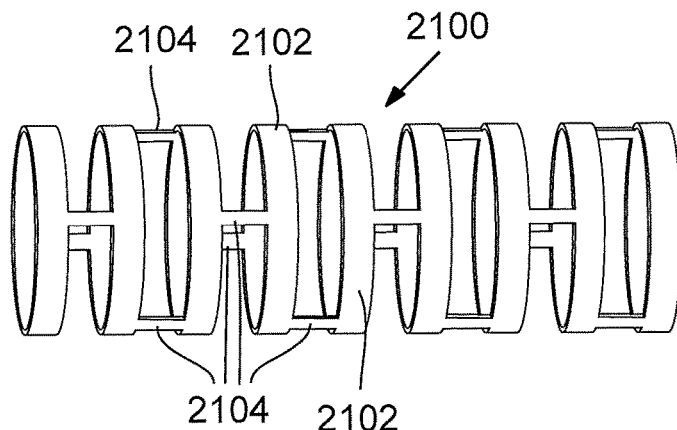
FIG. 61 is a perspective view of a segment of a sleeve of an introducer sheath, according to another embodiment.

FIG. 61 shows a segment of an alternative metal sleeve, indicated at 2100, that can be used in the introducer sheath 2000. The sheath 2000 in this embodiment desirably includes inner and outer polymeric layers, which desirably are secured to the metal sleeve only at its proximal and distal ends as discussed above. The sleeve 2100 includes circular bands 2102 connected by two links, or connecting portions, 2104, extending between two adjacent rings. Each pair of links connecting two adjacent bands 2102 desirably are spaced 180 degrees from each other and desirably are rotationally offset 90 degrees from an adjacent pair of links, which allows for multi-axial bending.

Figure 62:
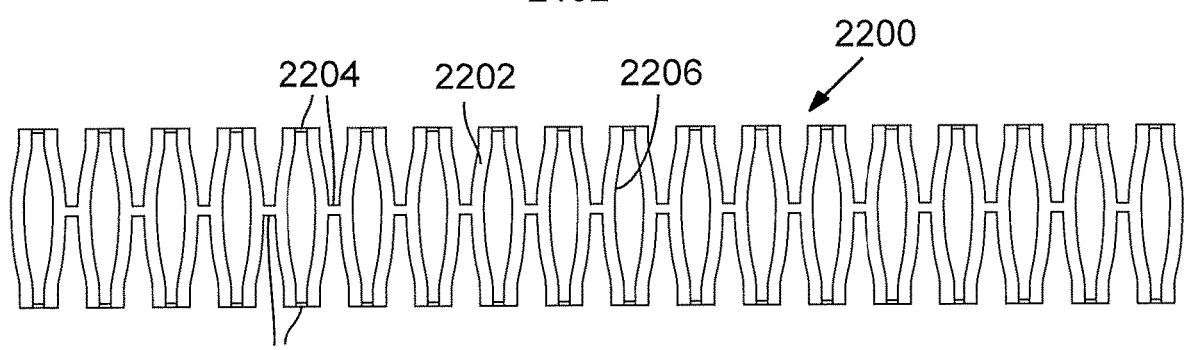
FIG. 62 is a side elevation view of a metal sleeve for an introducer sheath, according to another embodiment.

FIG. 62 shows a segment of another embodiment of a metal sleeve, indicated at 2200, that can be used in the introducer sheath 2000. The sleeve 2200 has the same cut pattern as the sleeve 2100, and therefore has circular bands 2202 and two links 2204 connecting adjacent bands, and further includes two cutouts, or apertures, 2206 formed in each band 2202 to increase the flexibility of the sleeve. The cutouts 2206 desirably have a generally elliptical shape, but can have other shapes as well. Each cutout 2206 desirably extends about 180 degrees in the circumferential direction of the sleeve and desirably is rotational offset about 90 degrees from a cutout 2206 in an adjacent band 2202.

Figure 63:
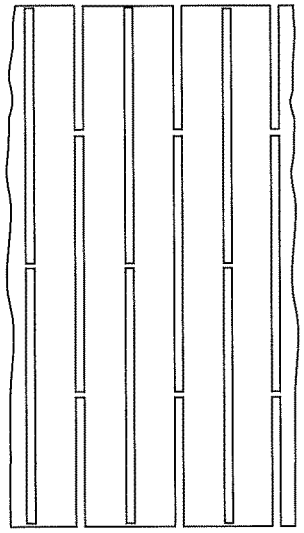
FIG. 63 shows the cut pattern for forming the metal sleeve of FIG. 61.
Figure 64:
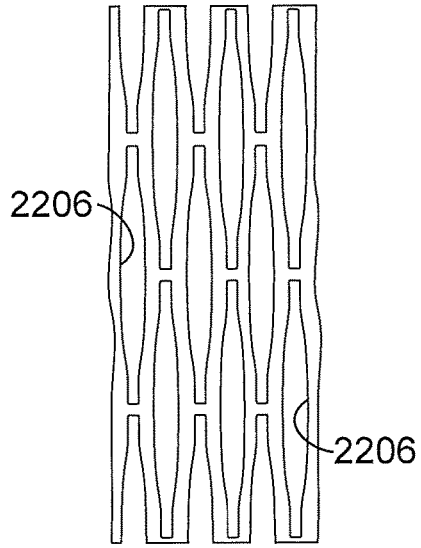
FIG. 64 shows the cut pattern for forming the metal sleeve of FIG. 62.
Figure 65:
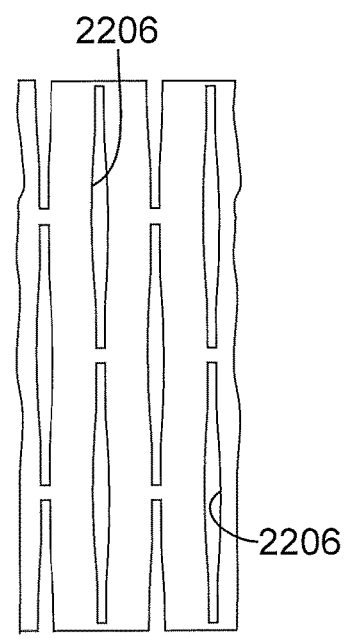
FIG. 65 shows a cut pattern similar to FIG. 64 but having narrower apertures.

In particular embodiments, the metal sleeve of an introducer sheath has a wall thickness in the range of about 0.002 inch to about 0.006 inch. In one implementation, a sheath has a metal sleeve having a wall thickness of about 0.002 inch and an inner diameter of about 0.229 inch, an inner polymeric layer having a wall thickness of about 0.0025 inch, an outer polymeric layer having a wall thickness of about 0.001 inch, and a total wall thickness (through all three layers) of about 0.0055 inch. In another implementation, a sheath has a metal sleeve having a wall thickness of about 0.004 inch and an inner diameter of about 0.229 inch, an inner polymeric layer having a wall thickness of about 0.0025 inch, an outer polymeric layer having a wall thickness of about 0.001 inch, and a total wall thickness (through all three layers) of about 0.0075 inch. FIG. 63 shows the cut pattern for forming the metal sleeve 2100 of FIG. 61. FIG. 64 shows the cut pattern for forming the metal sleeve 2200 of FIG. 62. FIG. 65 shows the same cut pattern as FIG. 64 but includes cutouts 2206 that are narrower than shown in FIG. 64.

TABLE 1

| Wall thickness of metal sleeve | Material | Minimum bend radius without visual kink | Minimum bend radius allowing passage of 16-Fr dilator |
|---|---|---|---|
| .004" | Nitinol | 1" | 1" |
| .004" | Stainless steel | 1" | 1" |
| .002" | Nitinol | 6" | 1" |
| .002" | Stainless steel | 6" | 1" |
| .002" | Stainless steel (wide rings) | 2" | 1" |

Table 1 above demonstrates the bend performance of several metal sleeves. Each metal sleeve had an inner diameter of about 0.229 inch. Each sleeve was formed with the cut pattern shown in FIG. 62, except for the last sleeve in Table 1, which was formed with the cut pattern shown in FIG. 61. Table 1 indicates that all of the sleeves providing deliverability at a relatively small bend radius (1 inch). Furthermore, it was found that the metal sleeves can recover their circular cross-sectional shapes even after passing a delivery device through a visibly kinked section of the sleeve.

Figure 66:
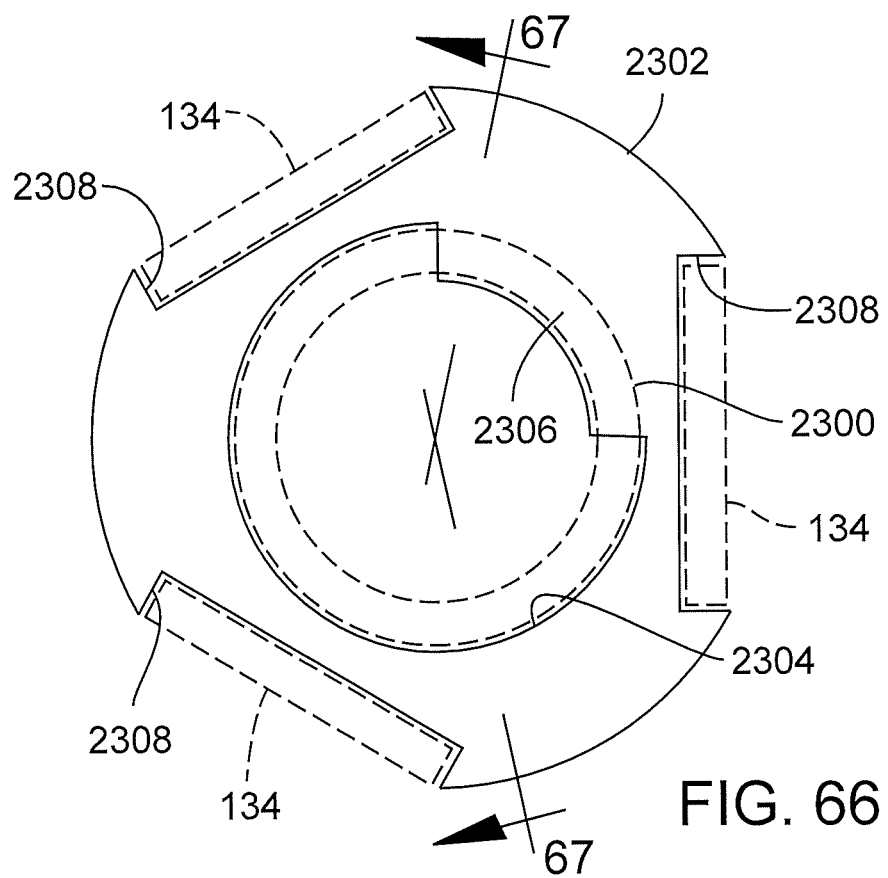
FIG. 66 is a front elevation view of a wire coil and washer assembly that can be incorporated in a torque shaft in place of the screw and nut assembly shown in FIG. 13.
Figure 67:
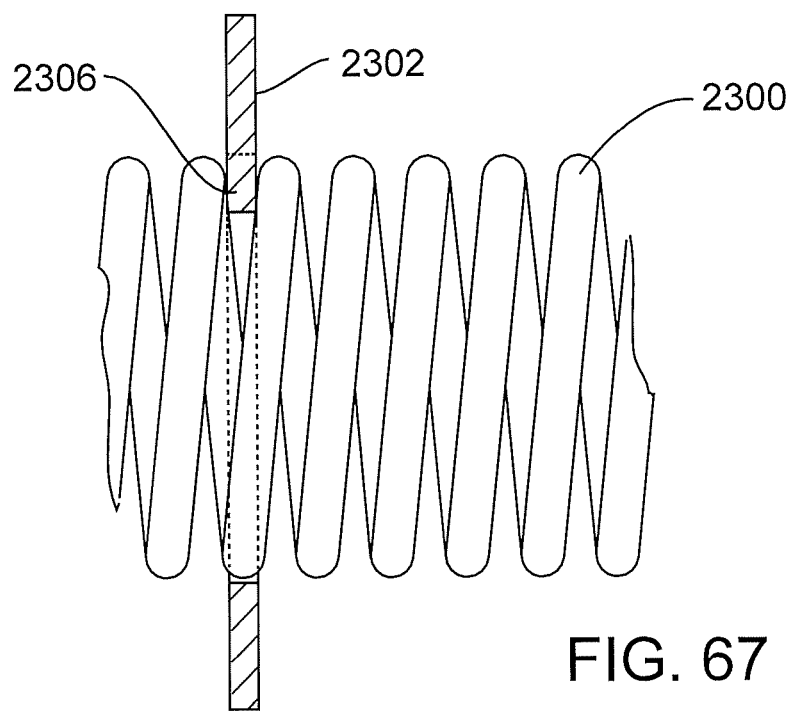
FIG. 67 is a side view of the wire coil and washer assembly of FIG. 66 shown partially in section.

FIGS. 66-67 show an alternative configuration for the screw 112 and nut 150 of the delivery apparatus 100. In this embodiment, the screw 112 is replaced with a helical coil 2300 (which can be, for example, a metal compression or tension spring), and the nut 150 is replaced with a sheath retaining ring in the form of a washer, or blade, 2302 mounted on the coil 2300. The proximal end of the coil is fixedly secured to the distal end of the torque shaft 110 (for example by welding or a suitable adhesive). The coil 2300 can be made of any of various suitable metals (e.g., stainless steel, Nitinol, etc.) or polymeric materials.

The washer 2302 has a central aperture 2304 that receives the coil 2300 and an internal tooth 2306 that engages the grooves defined on the outer surface of the coil and desirably extends radially inwardly between adjacent turns or loops of the coil. The outer circumferential edge of the washer 2302 can be formed with a plurality of recesses, or grooves, 2308, each of which is sized to receive a prong 134 of the outer fork 130, which prevents rotation of the washer upon rotation of the torque shaft 110. The sheath 106 can be secured to the outer circumferential edge of the washer 2302 in any convenient manner. For example, the portions between recesses 2308 can extend into the openings 172 of the sheath (FIG. 18) to fix the sheath axially and rotationally relative to the washer. Alternatively, the washer can be welded or adhesively secured to the sheath.

When incorporated in the delivery apparatus 100, the coil 2300 and washer 2302 operate in a manner similar to the screw 112 and nut 150. Thus, when the torque shaft 110 is rotated, the washer 2302 is caused to move axially along the length of the coil 2300 to effect corresponding axial movement of the sheath, either to deploy a prosthetic valve or recapture a prosthetic valve back into the sheath. An advantage of the coil and washer configuration is that it allows the distal portion of the delivery apparatus occupied by the coil to bend or flex to facilitate tracking through the patient's vasculature, especially in patients with relatively small aortic arches and short ascending aortas. The coil also allows the sheath to be moved (proximally or distally) upon rotation of the torque shaft when the coil is in a flexed or curved state inside the patient's vasculature. In particular embodiments, the distal portion of the delivery apparatus occupied by the coil can be flexed from a straight configuration to a curved configuration having a radius of curvature of about 1 cm. In addition, the coil can change its pitch under dynamic loading (compression or tension), which reduces the build-up of tensile forces along the length of the delivery apparatus and avoids galling of the washer when subjected to bending forces.

The coil and washer configuration can be implemented in other delivery apparatuses that are used to implant various other types of prosthetic implants within body ducts. For example, the coil and washer configuration can be incorporated in a delivery apparatus used to implant stents or similar implants within the coronary sinus. The coil and washer configuration can also be utilized in various non-medical applications to replace a screw and nut assembly where the screw is subjected to bending forces.

Figure 68:
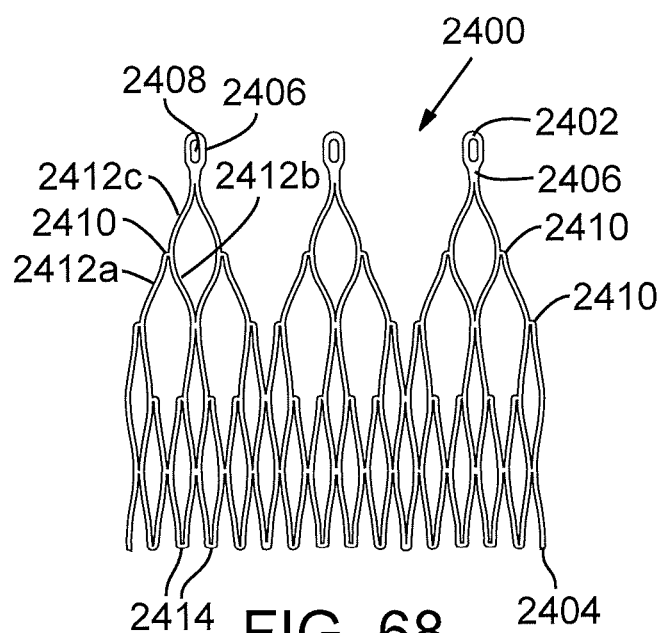
FIGS. 68-72 are flattened views of various embodiments of stents for prosthetic heart valves.
Figure 69:
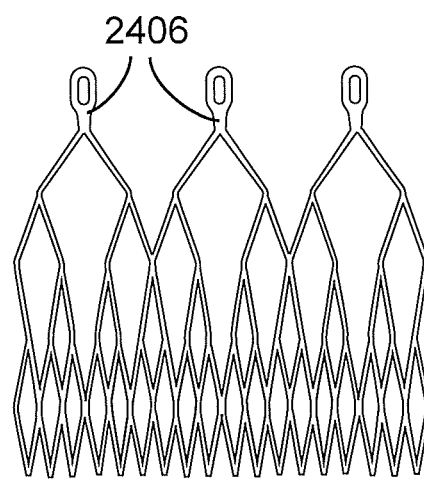
Figure 70:
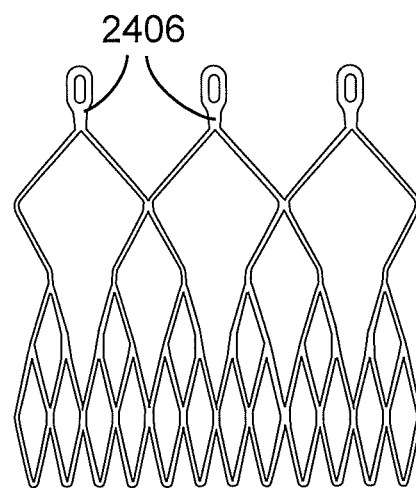
Figure 71:
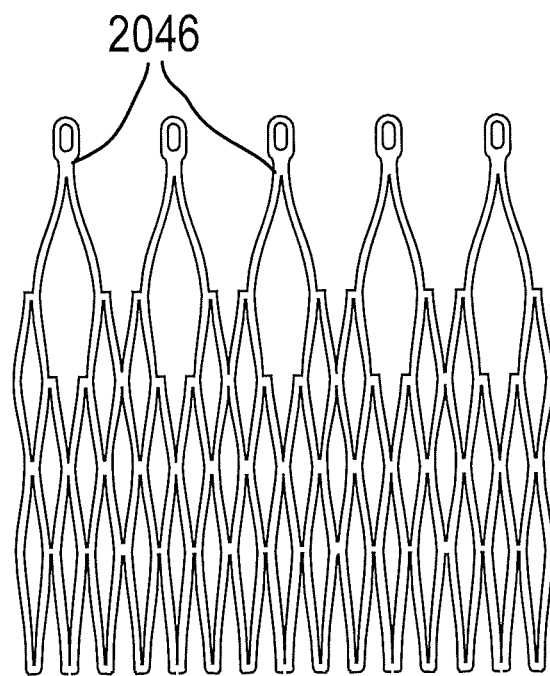
Figure 72:
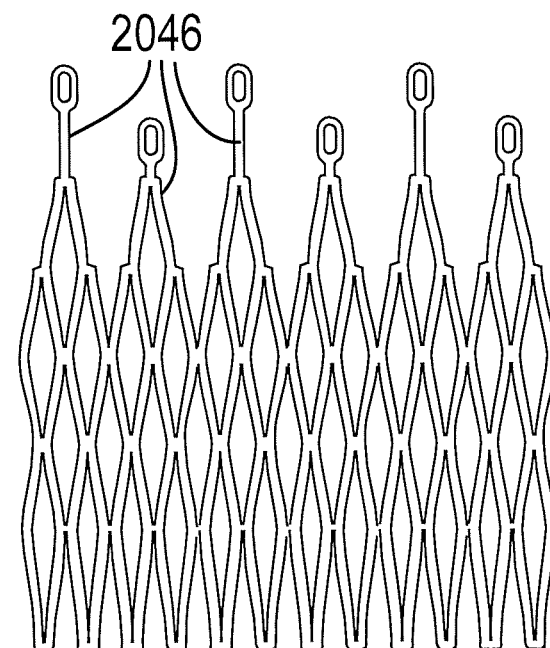

FIG. 68 shows an alternative embodiment of a stent 2400 that can be incorporated in a prosthetic heart valve, such as prosthetic valve 10. Thus, a leaflet assembly (e.g., leaflet assembly 14) can be mounted to the stent to form a prosthetic heart valve. Although FIG. 68 shows a flattened view of the stent, one skilled in the art will appreciate that the stent has an annular configuration, which can be substantially cylindrical or can be shaped to have a diameter that varies along the length of the stent (similar to stent 12). The stent 2400 can be made of various self-expandable materials (e.g., Nitinol) or plastically expandable materials (e.g., stainless steel), as known in the art.

The stent 2400 is configured to facilitate recapture of a prosthetic valve once fully deployed from a delivery sheath (e.g., sheath 106). As shown in FIG. 68, the stent has a first end 2402 (typically the outflow end of the stent) and a second end 2404 at the opposite end of the stent (typically the inflow end of the stent). The first end 2402 is configured to be releasably connected to a delivery apparatus. Thus, similar to stent 12, the stent 2400 has a plurality of retaining arms 2406, each having a corresponding opening 2408. The retaining arms 2406 of the stent 2400 can be releasably secured to the delivery apparatus 100 using the valve-retaining mechanism 114 comprised of the outer and inner forks 130, 132 described above. As can be seen, the stent 2400 is formed without any struts that form free apexes that point in the direction of the first end 2402, except for the retaining arms 2406. In other words, except for the retaining arms 2406, the stent comprises a plurality of apexes 2410 pointing in the direction of the first end, with each such apex 2410 being formed by two struts 2412a, 2412b in the same row of struts and at least a third strut 2412c in an adjacent row. Thus, each apex 2410 pointing in the direction of the first end 2402 are retained from flexing or bending outwardly relative to adjacent apexes. In contrast, the stent also can be formed with a plurality of free apexes 2414 pointing in the direction of the second end 2404 of the stent. The free apexes 2414 are not restrained from relative flexing like fixed apexes 2410.

In use, the retaining arms 2406 of the stent can be secured to the delivery apparatus 100 in the manner described above for delivery to an implantation site within a patient. When the delivery sheath 106 is retracted, the prosthetic valve self-expands to its expanded configuration (similar to prosthetic valve 10 shown in FIG. 36 or FIG. 42). If it becomes necessary to recapture the prosthetic valve back into the delivery sheath, such as to reposition the prosthetic valve or fully withdraw the prosthetic valve from the patient, the delivery apparatus can be operated to pull the prosthetic valve back into the sheath or move the sheath distally over the prosthetic valve. Because the stent 2400 does not include any free apexes pointing in the direction of the first end 2402, except for the retaining arms (which are secured to the delivery apparatus), the sheath can slide easily over the stent without catching any apexes of the stent. In other words, all of the apexes pointing toward the distal end of the delivery sheath are restricted from flexing or bowing outward into the path of travel of the delivery sheath as it is pushed back over the stent.

The stent 2400 is shown as having three free apexes/retaining arms 2406 at the first end of the stent, although this is not a requirement. The number of free apexes at the first end can vary, but desirably is equal to the number of prongs on each of the inner and outer forks of the valve-retaining mechanism so that each free apex at the first end 2402 can be secured to the valve-retaining mechanism. Also, the number of free apexes 2414 at the second end 2404 can vary. Table 2 below shows various combinations of inflow free apexes 2414, number of rows of struts, and outflow free apexes 2406 that can be implemented in a stent. As mentioned above, the stent of a prosthetic valve typically is secured to a delivery apparatus at the outflow end of the stent (in which case the first end 2402 is the outflow end of the stent). If the prosthetic valve and the delivery catheter are designed to secure the inflow end of the stent to the delivery catheter, then the stent can have the same construction except that the first end 2402 is the inflow end of the stent and the second end 2404 is the outflow end of the stent. In any case, the number of struts and apexes in each row of struts generally increases moving in a direction from the first end 2402 to the second end 2404.

If the prosthetic valve is intended to be secured to a delivery apparatus at the inflow or outflow end of the stent, then the stent can have a configuration in which the number of apexes in each row increases from the first end 2402 to the middle of the stent and then decreases from the middle to the second end 2404 of the stent. In particular embodiments, the stent can have a configuration that is symmetrical with respect a line that extends through the middle of the stent (perpendicular to the flow axis) and the number of apexes in each row increases from the first end 2402 to the middle of the stent and then decreases from the middle to the second end 2404 of the stent.

FIGS. 69-72 show alternative embodiments of stents formed from a plurality of struts without any free apexes pointing in a direction toward one end of the stent, except for retaining arms 2406. The stents illustrated in FIGS. 68-72 also can be implemented in prosthetic implants other than prosthetic valves, such as stent grafts or bare stents implanted in various ducts or lumens within the body.

TABLE 2

| Inflow Cell # (Inflow Free Apexes) | # of Rows of Struts | Outflow Cell # (Outflow Free Apexes/retaining arms) |
|---|---|---|
| 9 | 5 | 3 |
| 9 | 5 | 6 |
| 12 | 5 | 3 |
| 12 | 6 | 3 |
| 12 | 5 | 6 |
| 15 | 5 | 3 |
| 15 | 6 | 3 |
| 15 | 5 | 6 |
| 18 | 5 | 3 |
| 18 | 5 | 6 |
| 15 | 7 | 5 |

Figure 76:
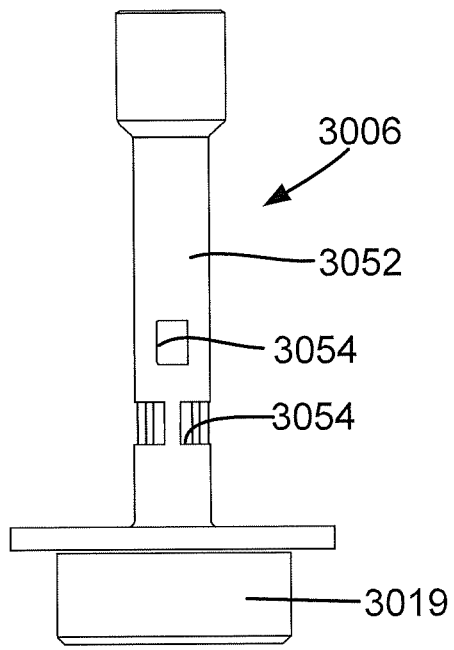
FIG. 76 is a side elevation view of a prosthetic valve transfer tube, according to one embodiment, that can be used to transfer a partially crimped prosthetic valve into a storage tube.
Figure 77:
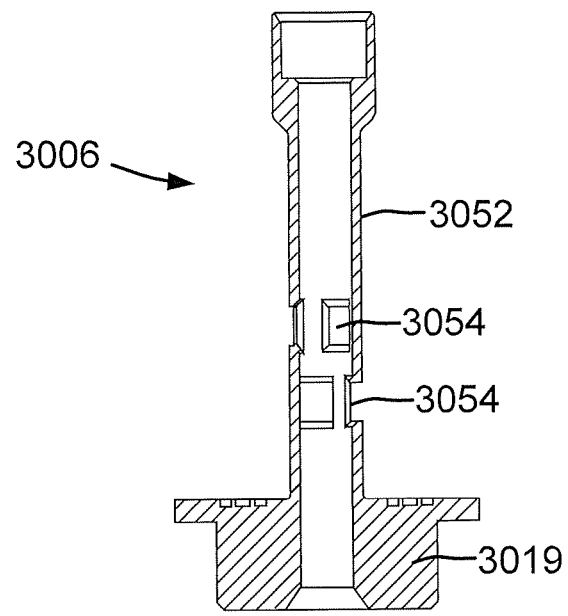
FIG. 77 is a cross-sectional view of the transfer tube of FIG. 76.
Figure 81:
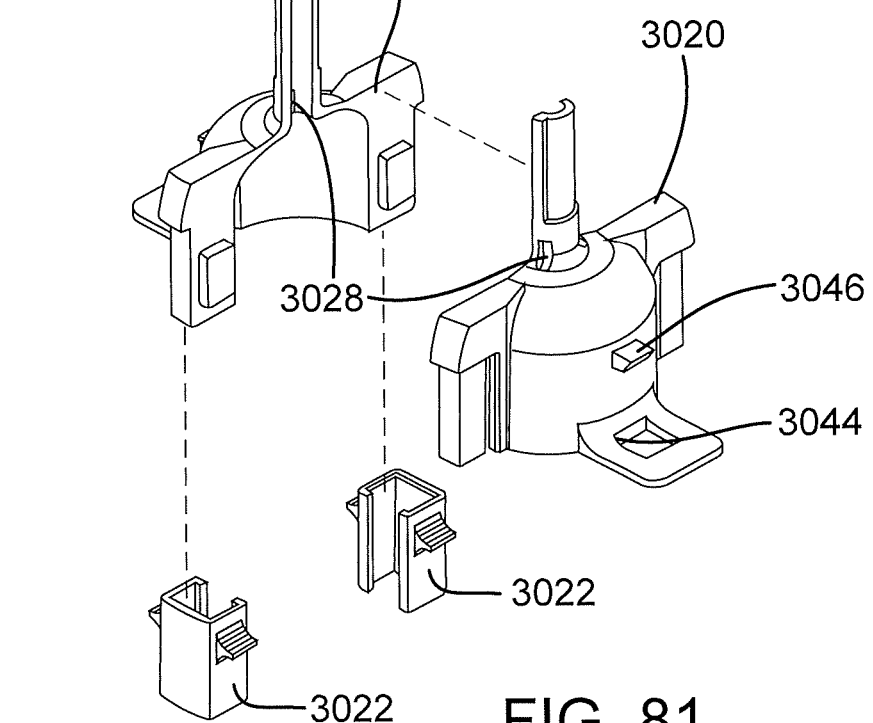
FIG. 81 is an exploded, perspective view of a valve attachment tool, according to one embodiment, that can be used to secure a prosthetic valve to a delivery apparatus.
Figure 82:
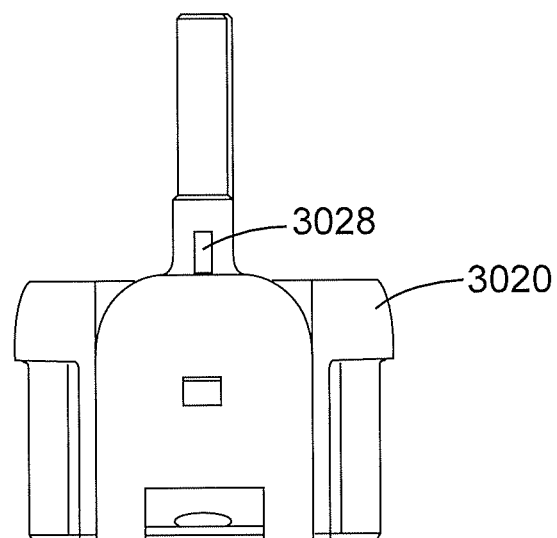
FIGS. 82 and 83 are elevation views showing the outside and inside surfaces, respectively, of a housing portion of the valve attachment tool shown in FIG. 81.
Figure 84:
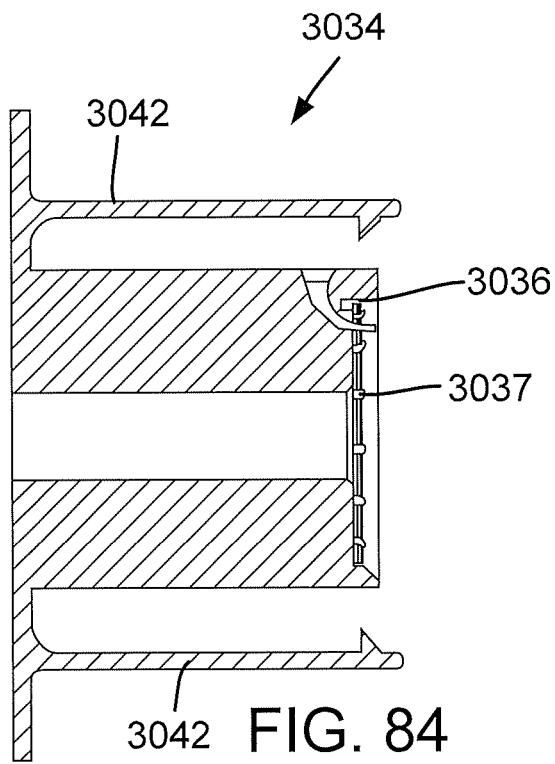
FIG. 84 is a cross-sectional view of a valve plunger, according to one embodiment, that is adapted to be used with the attachment tool of FIG. 81.
Figure 85:
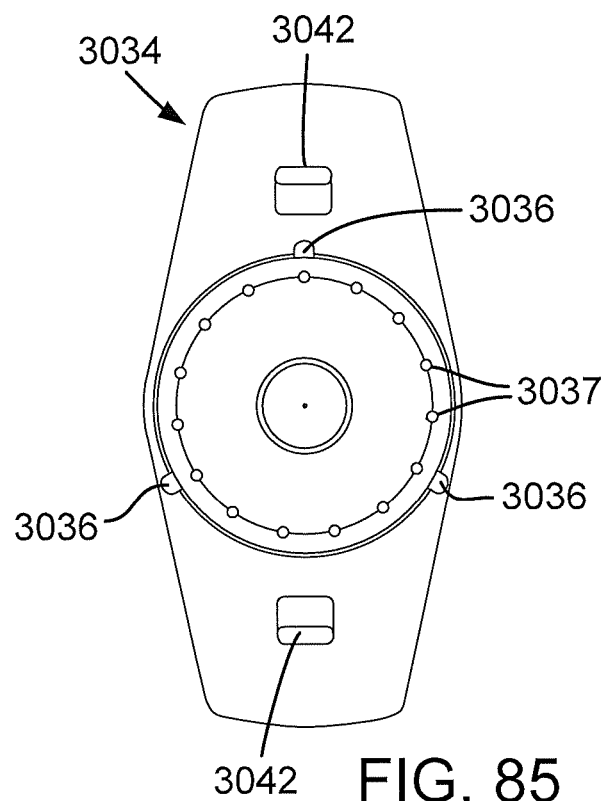
FIG. 85 is a bottom plan view of the valve plunger of FIG. 84.
Figure 86:
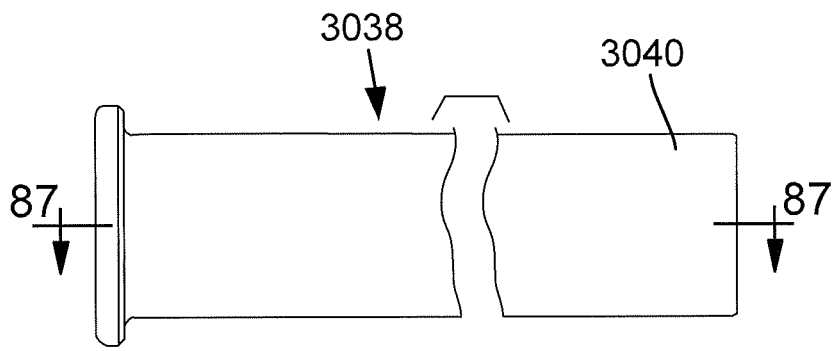
FIGS. 86 and 87 are side and cross-sectional views, respectively, of a protective sleeve or tube adapted to be used with the valve plunger of FIG. 84.
Figure 87:
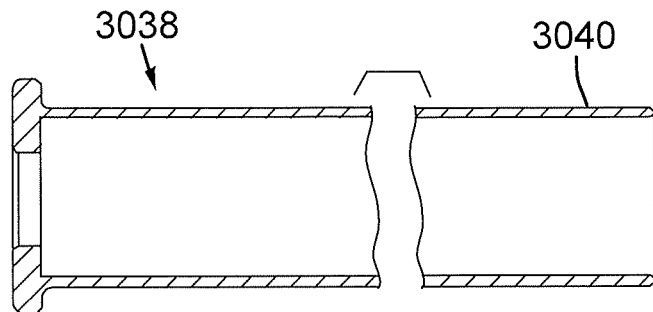

FIGS. 73-87 show the components of a system that can be used to connect a prosthetic valve 10 to a delivery apparatus 100 and to partially crimp the prosthetic valve for packaging the prosthetic valve and delivery apparatus assembly. The system generally includes a storage tube assembly 3000 (FIGS. 73-75), a transfer tube 3006 (FIGS. 76-77), an attachment spacer 3008 (FIGS. 78-80), an attachment tool 3018 (FIGS. 81-83), an attachment plunger 3034 (FIGS. 84-85), and a sleeve 3038 (FIGS. 86-87).

Figure 88:
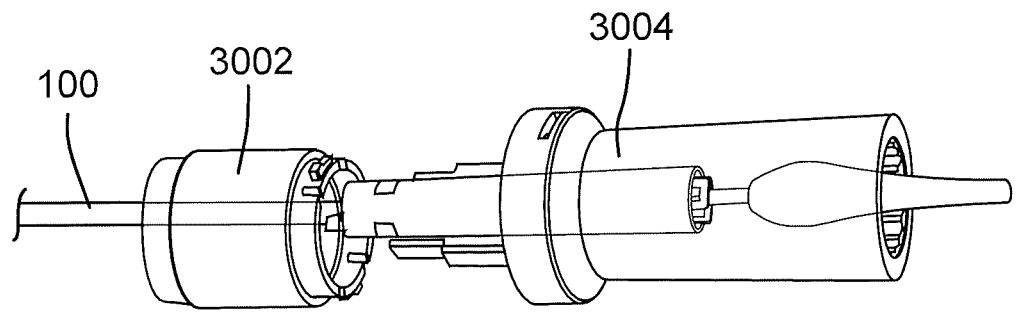
FIGS. 88-101 are various views illustrating an exemplary method for attaching a prosthetic valve to a delivery apparatus.
Figure 89:
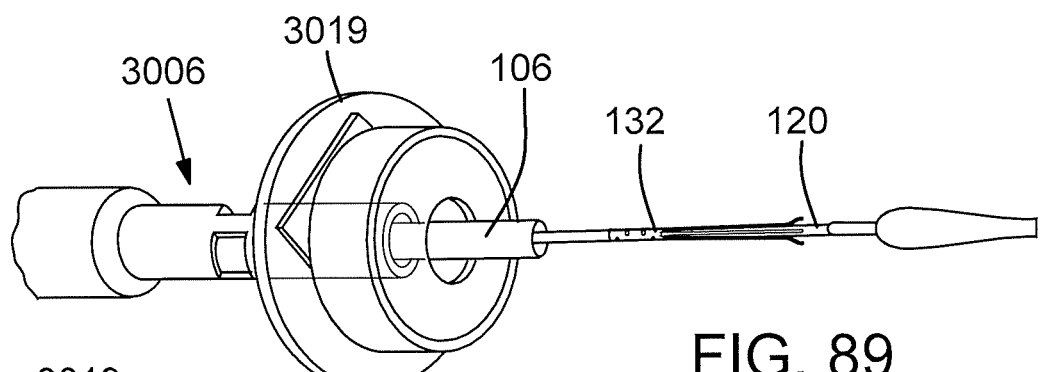

These components will be described in detail below in connection with a method for attaching the prosthetic valve 10 to the delivery apparatus 100 and a method for partially crimping the prosthetic valve and storing the prosthetic valve in the partially crimped state for final packaging of the prosthetic valve and delivery apparatus assembly. Referring first to FIG. 88, the storage tube assembly 3000, which comprises a front storage portion 3002 and a back storage tube portion 3004, is slid onto the distal end portion of the delivery apparatus. The storage tube assembly 3000 will be used later to store the prosthetic valve 10 in a partially crimped state for final packaging of the prosthetic valve and delivery apparatus assembly. Referring next to FIG. 89, following the storage tube assembly, the transfer tube 3006 is slid onto the distal end portion of the delivery apparatus and the nose catheter shaft 120 is pulled distally away from the sheath 106 a few inches.

Figure 78:
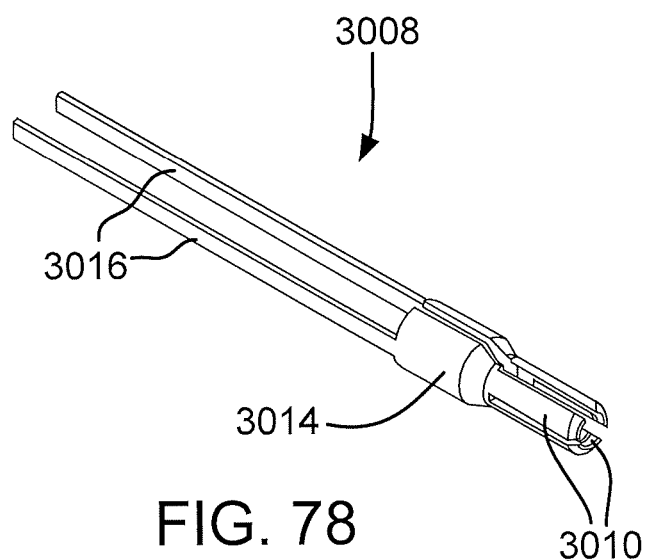
FIG. 78 is a perspective view of an attachment spacer device that can be used in connecting a prosthetic valve to a delivery apparatus.
Figure 79:
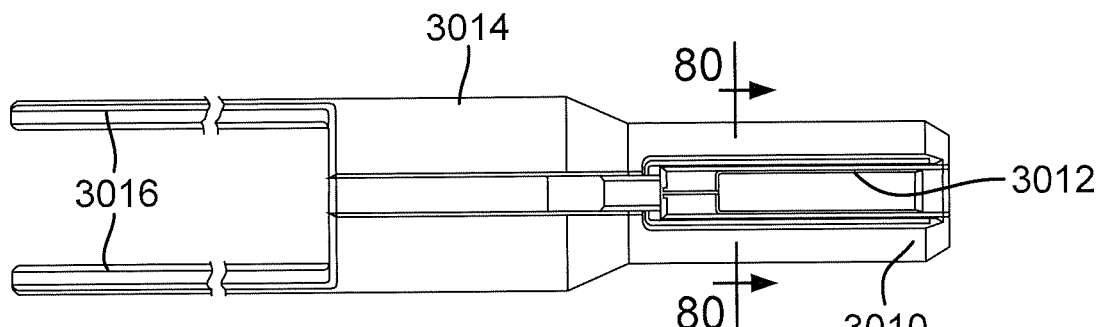
FIG. 79 is a side elevation view of the attachment spacer device of FIG. 78.
Figure 80:
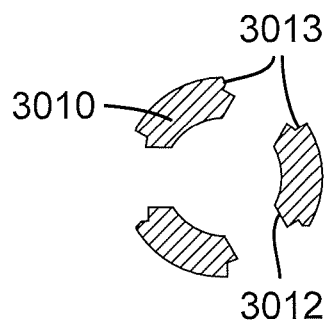
FIG. 80 is a cross-sectional view taken along line 80-80 of FIG. 79.
Figure 90:
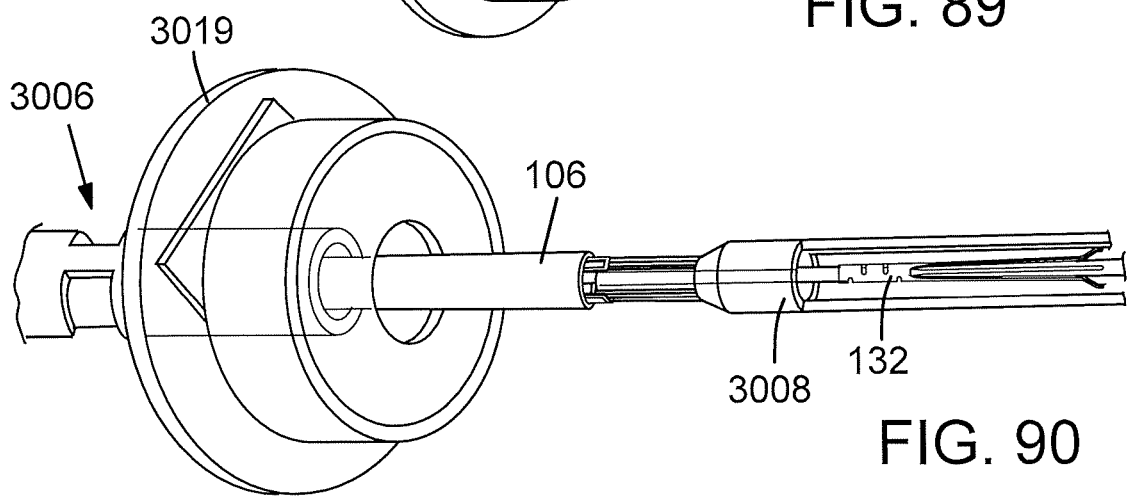
Figure 91:
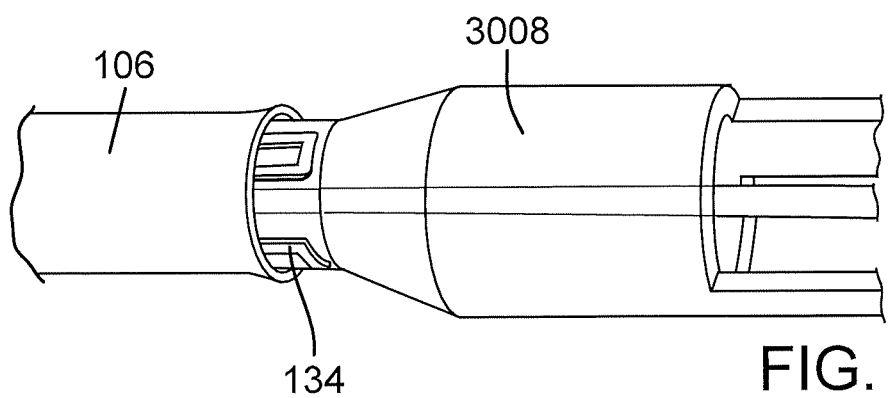

Referring next to FIGS. 90-91, the attachment spacer 3008 is placed on the nose cone shaft 120. As best shown in FIGS. 78-80, the attachment spacer 3008 comprises a plurality of proximal prongs, or tridents, 3010 extending from an intermediate hub portion 3014, and a plurality of longitudinally extending slots 3012 defined between adjacent prongs 3010. Extending from the opposite end of the hub portion are two elongated distal prongs 3016. As shown in FIGS. 90-91, the proximal prongs 3010 are radially compressed slightly by squeezing them toward each other and slid underneath the distal end portions of the prongs 134 of the outer fork 130. The distal end portion of each prong 134 is aligned with a respective slot 3012 and placed between a pair of adjacent prongs 3010 such that the side edges of each prong 134 can rest within recessed portions 3013 of the pair of adjacent prongs 3010 of the attachment spacer (see FIGS. 80 and 91).

Figure 92:
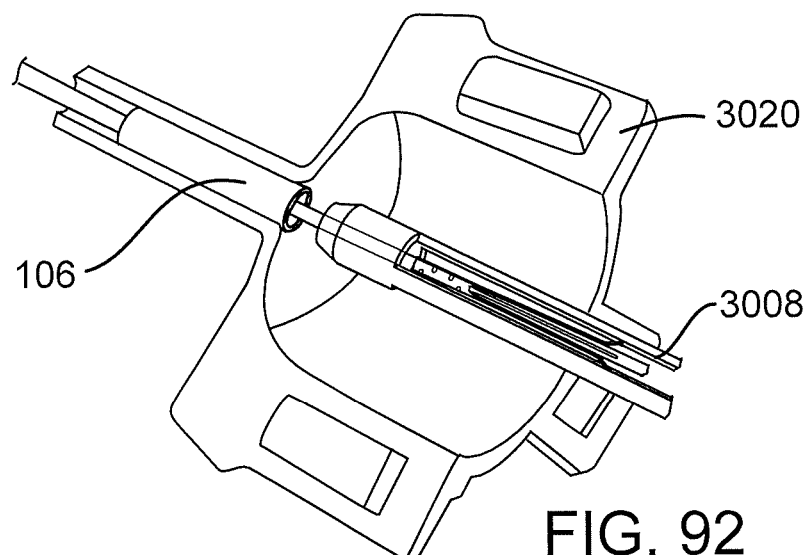
Figure 93:
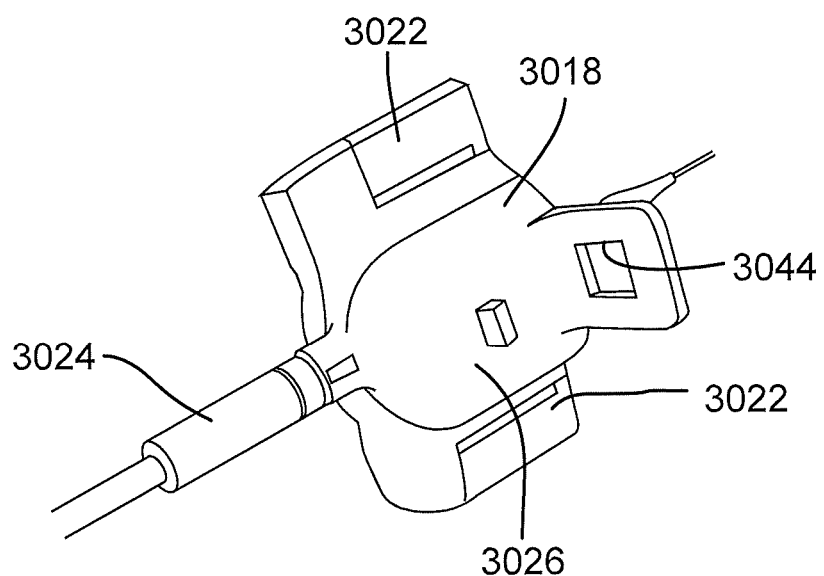
Figure 94:
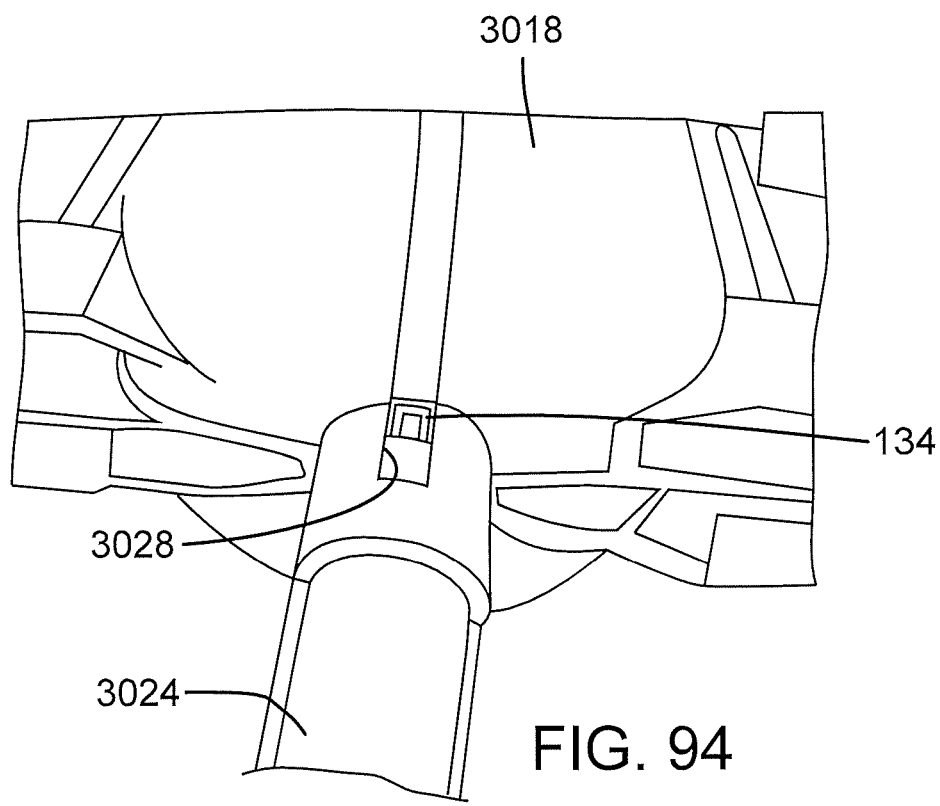
Figure 95:
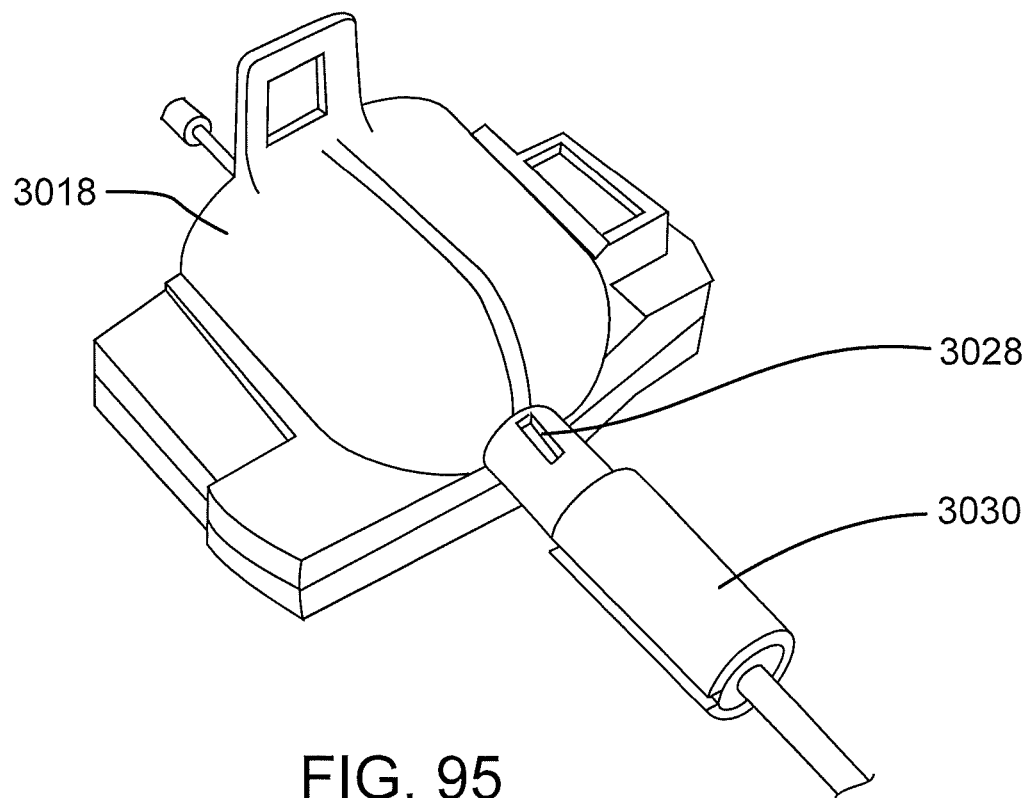
Figure 96:
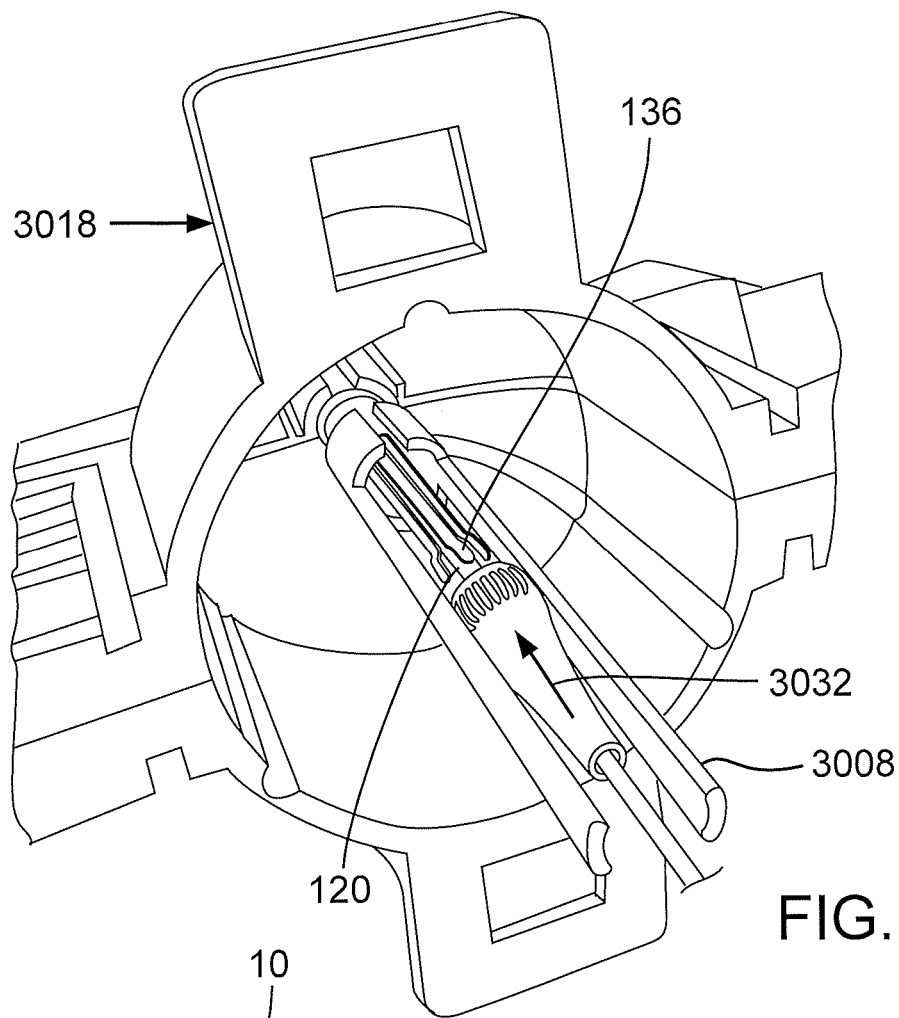
Figure 112:
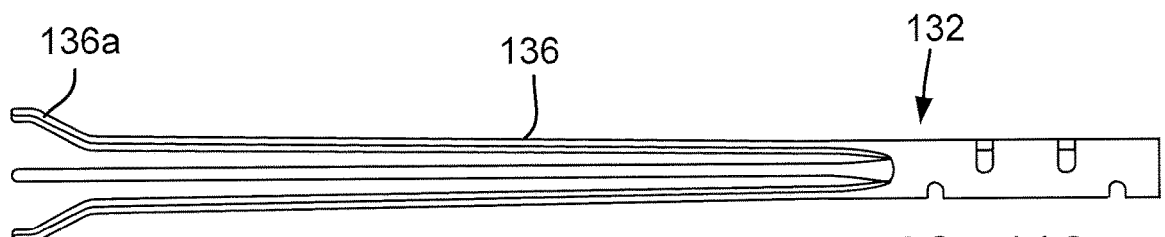

Referring next to FIGS. 92-93, the attachment tool 3018 is placed around the sheath 106 and the attachment spacer 3008. The attachment tool 3018 can comprise two separable housing portions 3020. When the two housing portions 3020 are placed together (FIG. 93), two locking clips 3022 can be placed on opposite side edges on the tool to hold the two housing portions together. The assembled attachment tool 3018 defines a generally cylindrical proximal portion 3024 that surrounds the delivery sheath 106 and a generally cylindrical, enlarged distal portion 3026 sized to receive the prosthetic valve 10 when the prosthetic valve is in an expanded state. As shown in FIG. 94, the attachment tool 3018 has three angularly spaced apertures, or windows, 3028 located at the area where the proximal portion 3024 begins to transition into the enlarged distal portion 3026. Each prong 134 of the outer fork 130 is aligned within a respective window 3028 such that the opening 140 of each prong 134 is centered within a corresponding window 3028, as shown in FIG. 94. As shown in FIG. 95, a bottom locking component 3030 is slid over and placed around the proximal portion 3024. The locking component 3030 can apply sufficient pressure to the proximal portion to retain the attachment tool relative to the sheath 106. As shown in FIG. 96, the prongs 136 of the inner fork 132 are rotational aligned with the prongs 134 of the outer fork. The shaft 120 is then pulled in the proximal direction (toward the proximal portion 3024 of the attachment tool, as indicated by arrow 3032) until the inner prongs 136 are at a location proximal to the windows 3028 in the attachment tool. As shown in FIG. 112, the prongs 136 of the outer fork 132 can have outwardly curved distal end portions 136a that generally define a cone shape to facilitate insertion of the outer prongs 136 to the stent retaining arms 30.

Figure 97:
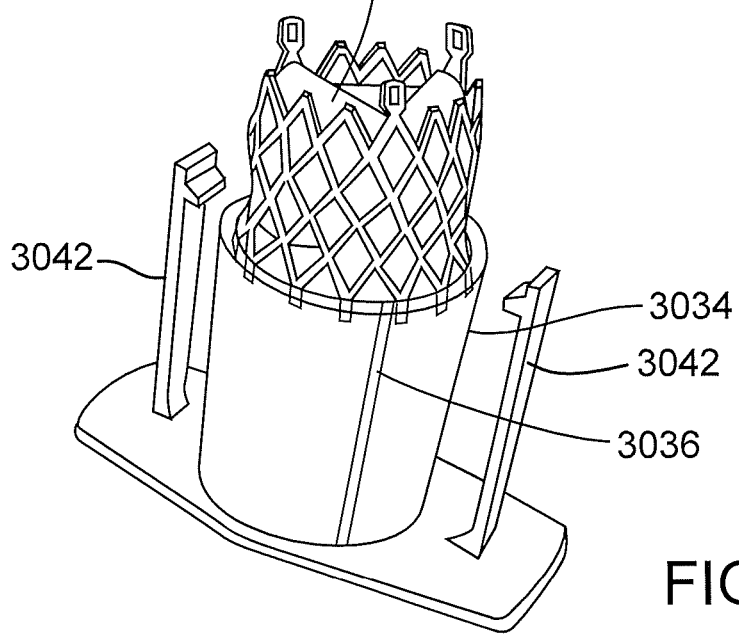
Figure 98:
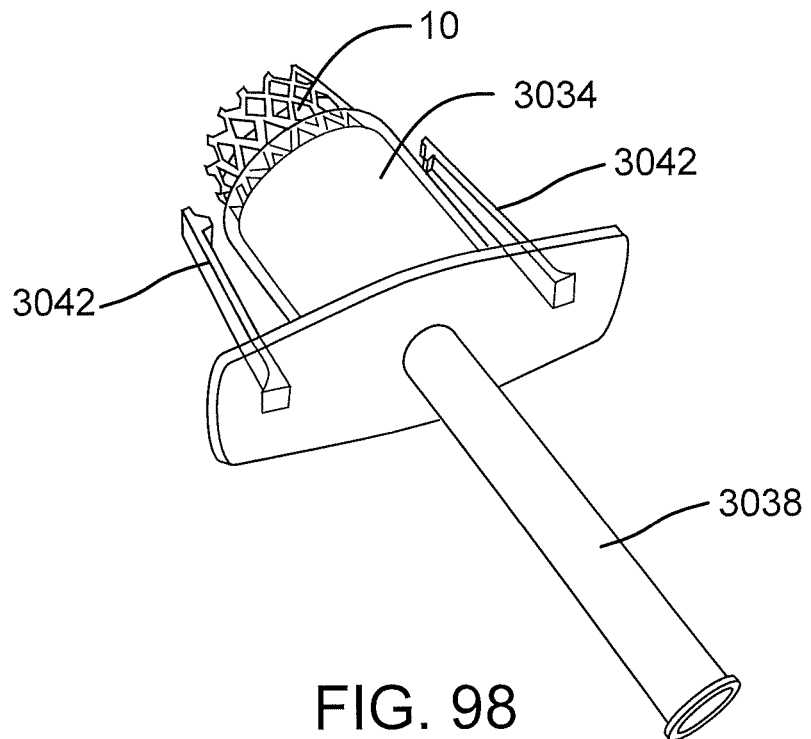
Figure 99:
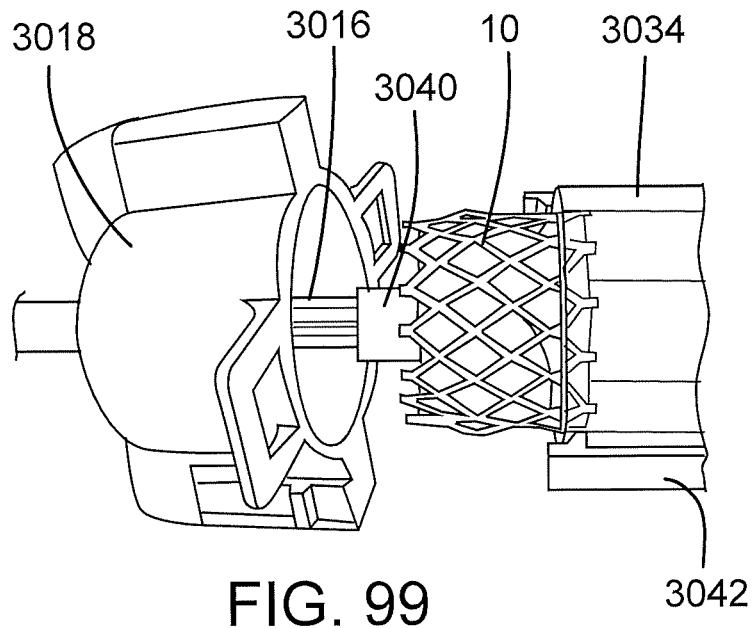

Referring next to FIG. 97, the prosthetic valve 10 is mounted on an attachment plunger 3034 by aligning the commissures of the prosthetic valve with respective guide rails 3036 (see also FIG. 85) of the plunger and partially inserting the inflow end of the prosthetic valve into an opening at the proximal end of the plunger. The inside surface adjacent the opening of the plunger can be formed with small recesses 3037 (FIG. 85) sized to receive the apexes of the stent 12 of the prosthetic valve. The prosthetic valve 10 can pressed into the plunger so that the apexes of the stent snap into the recesses in the plunger. Referring to FIG. 98, the protective tubular sleeve 3038 is inserted through the plunger 3034 and the prosthetic valve 10 until a proximal end portion 3040 of the sleeve extends slightly beyond the outflow end of the prosthetic valve 10 (FIG. 99). The sleeve 3038 shields the leaflets of the prosthetic valve during the subsequent step of securing the prosthetic valve to the delivery apparatus.

Figure 83:
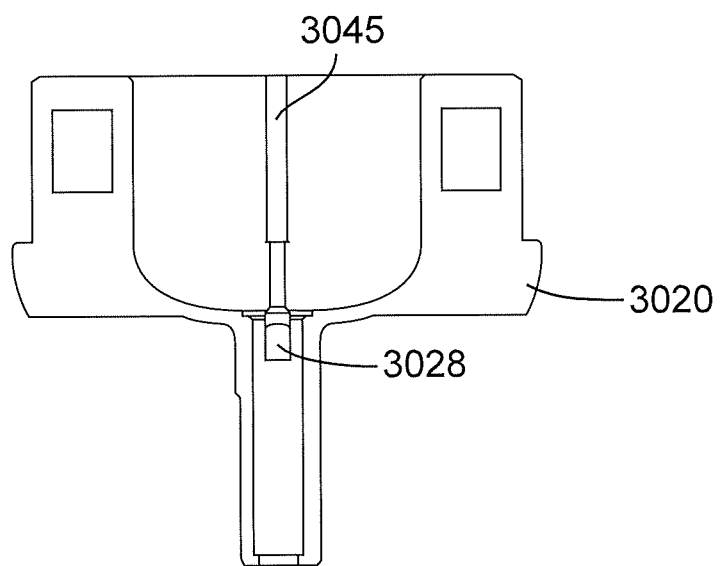
Figure 100:
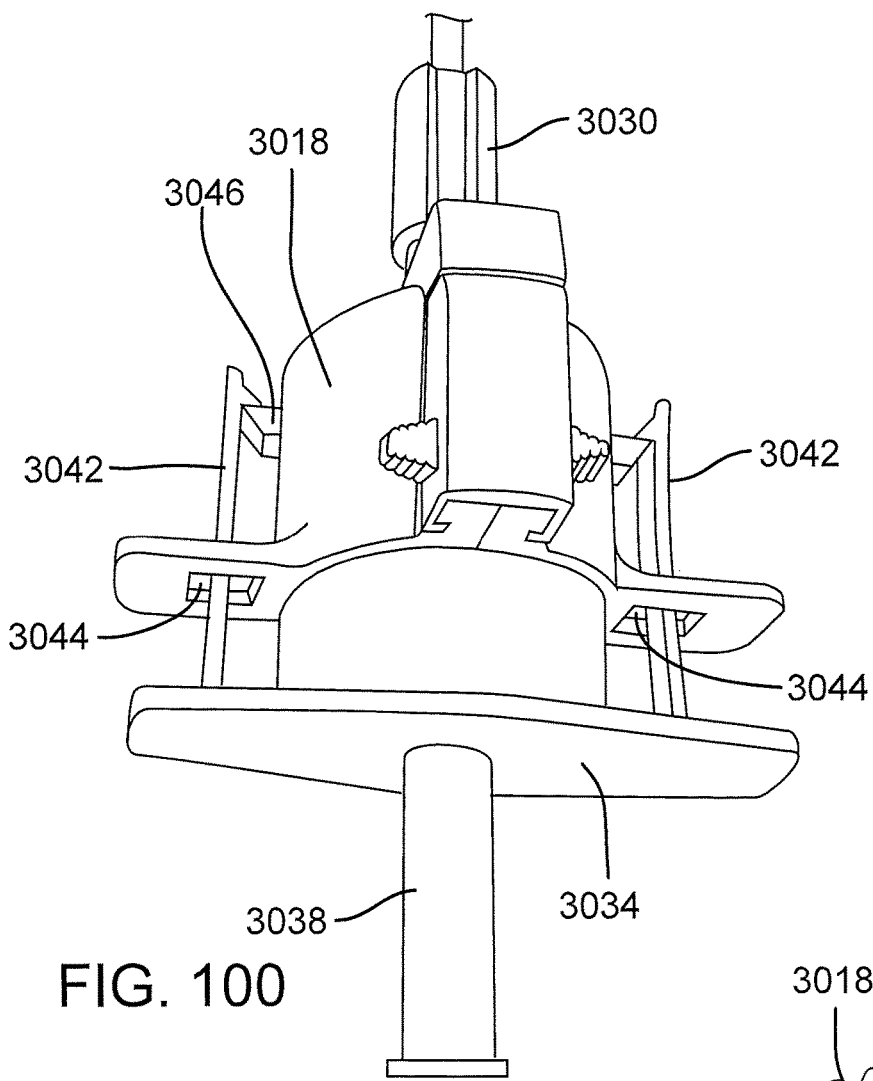
Figure 101:
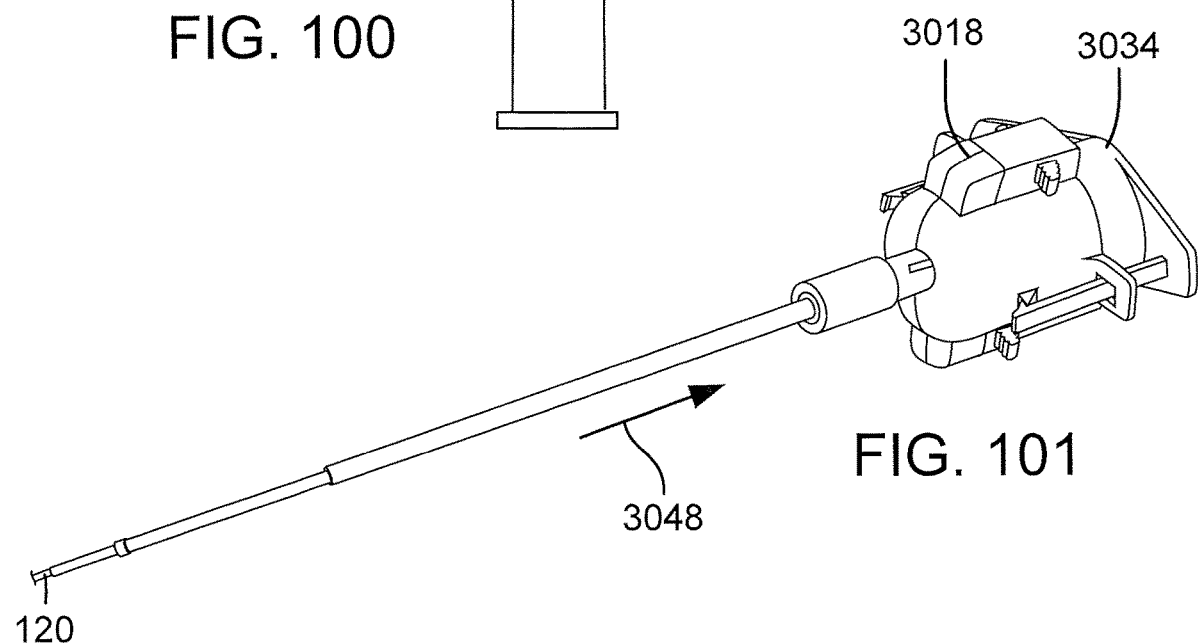
Figure 113:
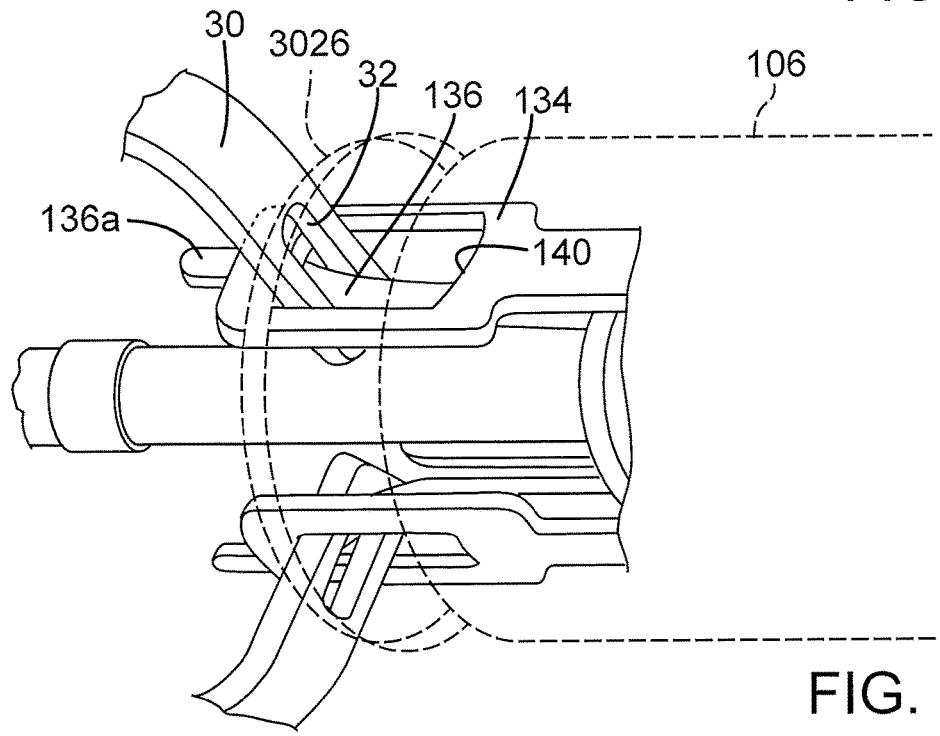

FIGS. 99 and 100 show the plunger and the attachment tool being used to secure the prosthetic valve 10 to the delivery apparatus. As shown in FIG. 99, the distal prongs 3016 of the attachment spacer 3008 are inserted into the proximal end portion 3040 of the sleeve 3038, and resilient locking arms 3042 of the plunger are rotational aligned with mating openings 3044 of the attachment tool. Thereafter, as shown in FIG. 100, the prosthetic valve 10 and the plunger 3034 are pressed into the attachment tool 3018 until the locking arms 3042 extend over and snap into place behind locking tabs 3046 on the attachment tool. The action of pushing the prosthetic valve into the attachment tool causes the retaining arms 30 of the prosthetic valve to slide along the inner surface of distal portion 3026 of the attachment tool and then inwardly through respective openings 140 in the prongs 134 of the outer fork (see FIG. 113). As best shown in FIG. 83, the inside surface of the attachment tool can be formed with three angularly spaced grooves 3045 aligned with windows 3028 to assist in guiding the retaining arms 30 of the stent along the inner surface of the attachment tool and through the openings 140 of the prongs 134. At this stage, as shown in FIG. 101, the nose cone shaft 120 is advanced distally (in the direction of arrow 3048, which causes the prongs 136 of the inner fork to extend through the openings 32 in the retaining arms 30 of the prosthetic valve, thereby securing the prosthetic valve to the delivery apparatus (see also FIG. 113). Once the prosthetic valve is secured to the delivery apparatus, the attachment tool, the plunger, and the attachment spacer can be removed from the delivery apparatus.

Figure 102:
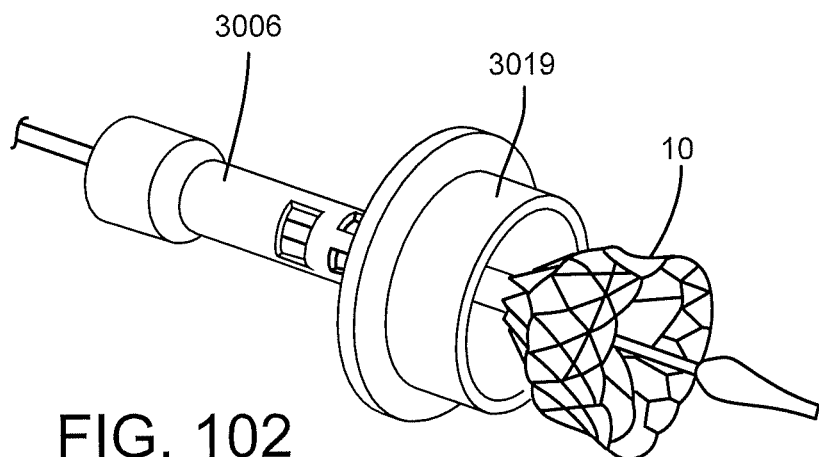
Figure 103:
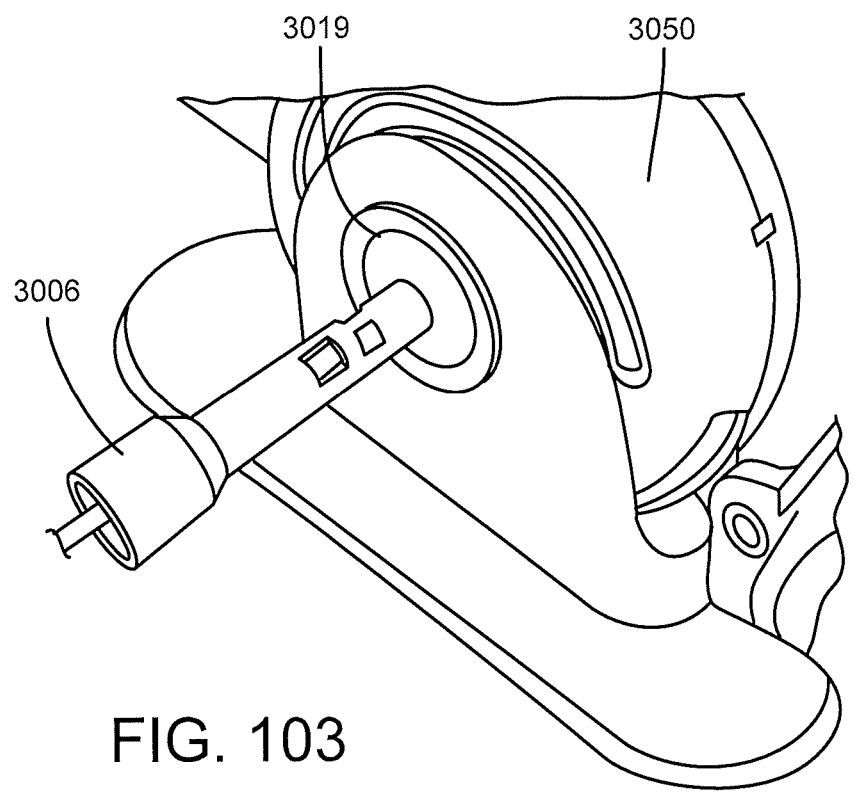
Figure 104:
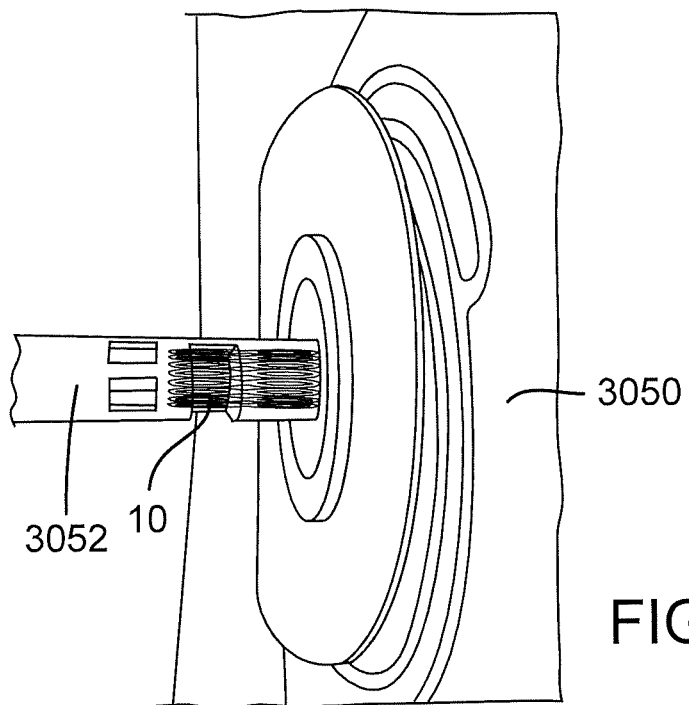

Referring next to FIG. 102, the transfer tube 3006 (previously placed on the delivery apparatus), is moved to a position adjacent the prosthetic valve. Then, as shown in FIG. 103, the prosthetic valve 10 and an enlarged end portion 3019 of the transfer tube are inserted into the aperture of a valve crimper 3050. The valve crimper 3050 is used to crimp (radially compress) the prosthetic valve to a partially crimped state so that the partially crimped prosthetic valve can be pulled into the main cylinder 3052 of the transfer tube. A partially crimped state means that the prosthetic valve is radially compressed from its fully expanded state to a state between its fully expanded state and its fully compressed state in which the prosthetic valve can fit inside the delivery sheath 106.

Figure 105:
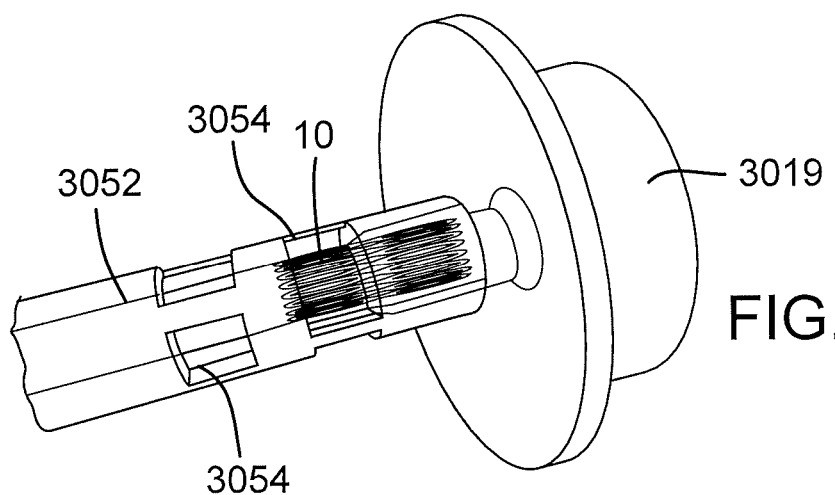
Figure 106:
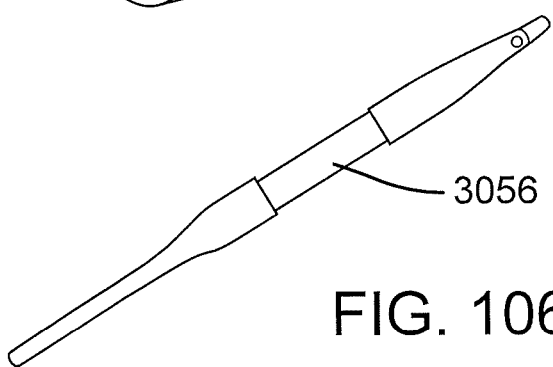
Figure 107:
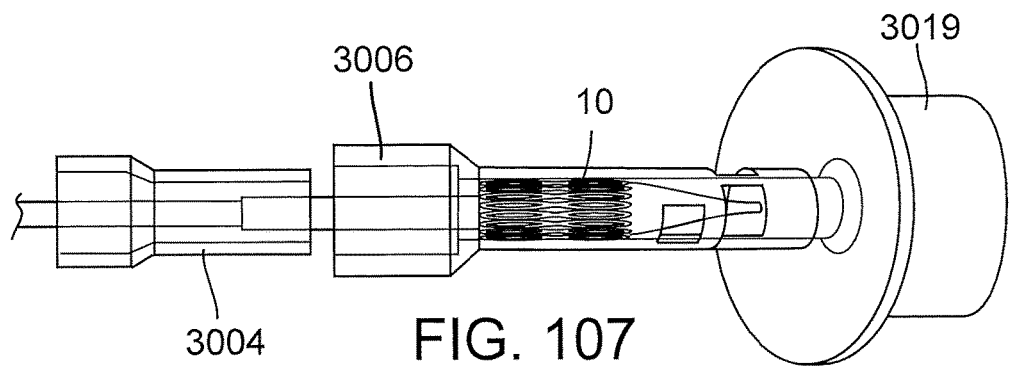
Figure 108:
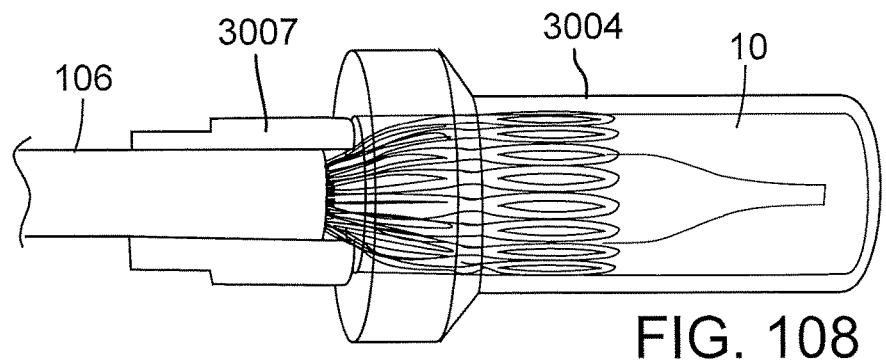
Figure 109:
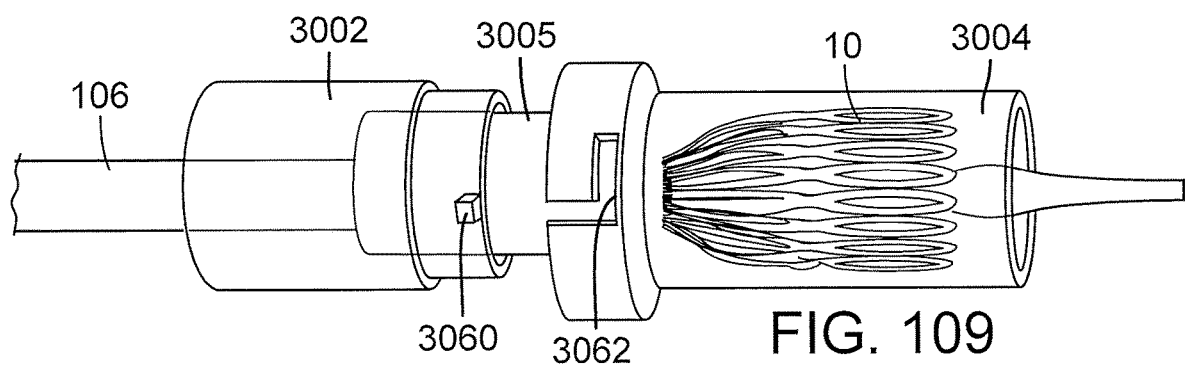
Figure 110:
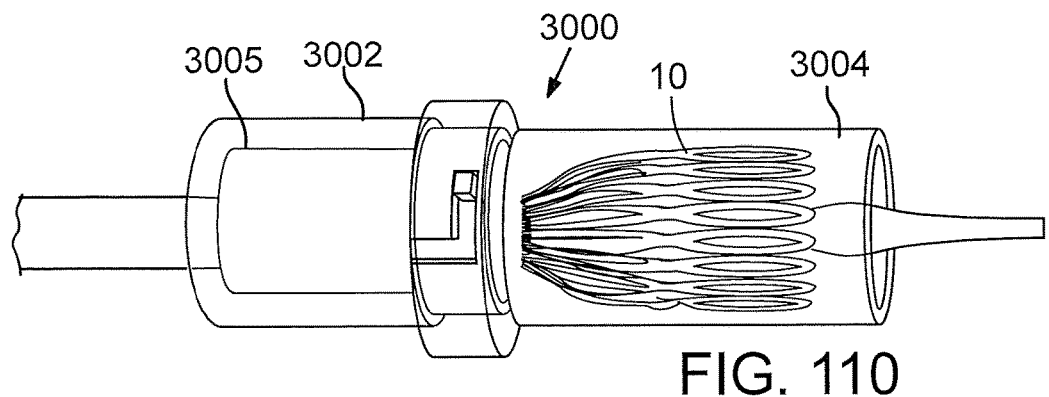

As shown in FIG. 105, the main cylinder 3052 has a plurality of leaflet tucking windows 3054. Using a tucking tool 3056 (FIG. 106), a user can insert the tucking tool 3056 through windows 3054 and into the individual cells of the stent 12 to make sure all leaflet and skirt material is "tucked" inside of the metal struts of the stent. As shown in FIGS. 107 and 108, the back storage tube portion 3004 is then inserted into the main cylinder 3052 of the transfer tube. Finally, as shown in FIGS. 109 and 100, a cap portion 3005 is placed on an extension portion 3007 of the back storage tube portion 3004, and the front storage tube portion 3002 is secured to the back storage tube portion 3004. As best shown in FIG. 74, the front storage tube portion 3002 can have locking tabs 3060 that are received in corresponding slots 3062 on the back storage tube portion 3004. Portions 3002 and 3004 can be secured together by inserting tabs 3060 into slots 3062 and twisting portion 3002 to establish a snap fit connection between these two components.

Figure 111:
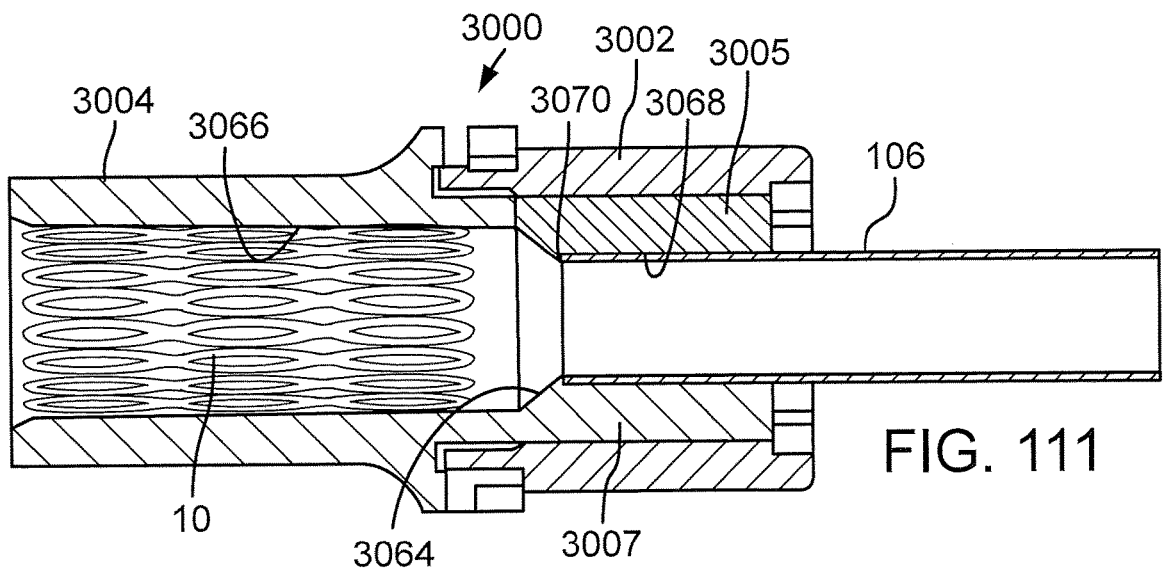

FIG. 111 shows the prosthetic valve 10 inside the back storage tube portion 3004 and the delivery sheath 106 extending partially into the opposite end portion of the back storage tube portion. As shown, the inner surface of the storage tube assembly is formed with a tapered surface 3064 extending from an inner bore 3066 containing the prosthetic valve to an inner bore 3068 having a reduced diameter containing the sheath 106. The tapered surface 3064 helps guide and fully crimp the prosthetic valve as it is pulled within the sheath 106. The opening of the bore 3068 closest to the tapered surface is formed with an annular lip 3070 that abuts the distal end of the sheath 106.

In particular embodiments, the assembly comprising the delivery apparatus 100, the storage tube assembly 3000, and the partially crimped prosthetic valve 10 (inside bore 3066) can be packaged together in a sterile package enclosing all of these components. The package containing these components can be supplied to end users for storage and eventual use. In particular embodiments, the leaflets 34 of the prosthetic valve (typically made from bovine pericardium tissue or other natural or synthetic tissues) are treated during the manufacturing process so that they are completely or substantially dehydrated and can be stored in a partially or fully crimped state without a hydrating fluid. In this manner, the package containing the prosthetic valve and the delivery apparatus can be free of any liquid. Methods for treating tissue leaflets for dry storage are disclosed in U.S. Pat. No. 8,007,992 and U.S. Patent Publication No. 2009/0164005, filed Dec. 18, 2008, both of which documents are incorporated herein by reference.

When the surgeon is ready to implant the prosthetic valve in a patient, the delivery apparatus 100, the partially crimped prosthetic valve 10, and the storage tube assembly 3000 can be removed from the package while inside the operating room. The prosthetic valve 10 can be loaded into the sheath 106 by rotating the torque shaft 110 in a direction to urge the sheath 106 against the annular lip 3070, which causes the prosthetic valve to slide into the sheath 106. If a motorized handle is provided (as described above), the torque shaft can be rotated by actuating the motor of the handle. Once the prosthetic valve is inside the sheath, the storage tube assembly 3000 can be removed from the delivery apparatus, which is now ready for insertion into the patient. As can be appreciated, storing the prosthetic valve in a partially crimped state inside the storage tube assembly eliminates the task of connecting the prosthetic valve to the delivery apparatus and greatly simplifies the crimping process for the surgeon.

Figure 52:
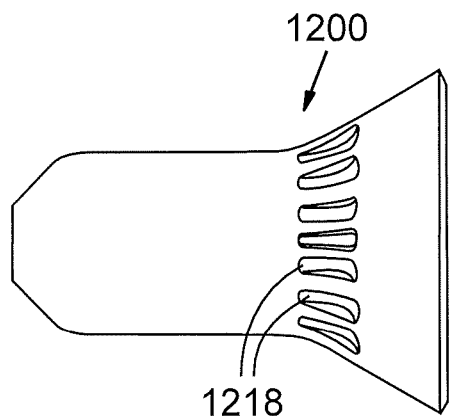
FIG. 52 is a perspective view of an alternative embodiment of the loading cone of FIG. 51.

In an alternative embodiment, the prosthetic valve, once attached to the delivery apparatus, can be partially crimped using a loading cone tool, such as shown in FIGS. 51-52. The prosthetic valve can be stored in a partially crimped state inside the loading cone (e.g., with the section 1210 of cone 1200), which can be packaged together with the delivery apparatus. When the delivery apparatus and prosthetic valve are to be used, the surgeon can remove the assembly from the package and load the prosthetic valve into the sheath 106, such as by activating the torque shaft, which causes the prosthetic valve to be pulled from the loading cone into the sheath.

In additional embodiments, the leaflets of the prosthetic valve can be treated for wet storage of the prosthetic valve, in which case the partially crimped prosthetic valve along with the component retaining the prosthetic valve in the partially crimped state (e.g., a loading cone or the storage tube assembly described above) can be placed in a sealed storage container containing a hydrating fluid for the leaflets. If the prosthetic valve is pre-mounted to the delivery apparatus as described above, the packaging for the delivery apparatus and the prosthetic valve can include a sealed storage container with a hydrating fluid (a wet storage compartment) containing the prosthetic valve, the component retaining the prosthetic valve, and the distal end portion of the delivery apparatus. The remaining portion of the delivery apparatus can extend out of the wet storage compartment into a dry storage compartment of the packaging. A method for treating tissue leaflets for wet storage are disclosed in U.S. Pat. No. 7,579,381, which is incorporated herein by reference.

In other embodiments, the prosthetic valve can be pre-mounted on the delivery apparatus as described above but is not pre-crimped, and instead is packaged together with the delivery apparatus with the prosthetic valve in its fully expanded state (either in a wet or dry storage compartment).

In view of the many possible embodiments to which the principles of the disclosed invention may be applied, it should be recognized that the illustrated embodiments are only preferred examples of the invention and should not be taken as limiting the scope of the invention. Moreover, additional embodiments are disclosed in U.S. Patent Application Publication No. 2010/0049313 (U.S. application Ser. No. 12/429,040), which is incorporated herein by reference. Accordingly, the scope of the invention is defined by the following claims. We therefore claim as our invention all that comes within the scope and spirit of these claims.

The invention claimed is:

1. A prosthetic heart valve delivery system, comprising:
a catheter portion comprising a sheath and an inner shaft, at least a portion of the inner shaft positioned within a lumen of the sheath, the inner shaft configured to support a radially collapsible prosthetic heart valve and having a nose cone attached to a distal end thereof, the inner shaft and the nose cone having a guidewire lumen extending therethrough, the sheath configured to cover and uncover the prosthetic heart valve mounted on the inner shaft;
a handle comprising a sheath actuator operatively coupled to a proximal portion of the sheath, the inner shaft extending through the handle; and
a shaft retractor coupled to a proximal portion of the handle such that the shaft retractor has a locked position relative to the handle and an unlocked position where the shaft retractor is disengaged from the handle and is movable axially relative to the handle, wherein the shaft retractor comprises a portion that is pressed radially inwardly to unlock the shaft retractor from the handle, and wherein the shaft retractor is fixedly coupled to a proximal portion of the inner shaft such that axial motion of the shaft retractor effects corresponding axial motion of the inner shaft;
wherein the sheath actuator is operable move the sheath axially relative to the inner shaft when the shaft retractor is coupled to the handle, wherein proximal movement of the sheath relative to the inner shaft causes the sheath to uncover the prosthetic heart valve mounted on the inner shaft to allow the prosthetic heart valve to radially expand; and
wherein the shaft retractor is operable to retract the inner shaft and the nosecone proximally relative to the sheath when the shaft retractor is unlocked from the handle.

2. The system of claim 1, wherein the shaft retractor is operable to retract the nosecone proximally through the prosthetic heart valve after the prosthetic heart is uncovered by the sheath and allowed to radially expand.

3. The system of claim 1, wherein the shaft retractor is operable to translate the inner shaft through the handle when the shaft retractor is unlocked from the handle.

4. The system of claim 1, wherein the shaft retractor is manually translatable relative to the handle when the shaft retractor is unlocked from the handle.

5. The system of claim 1, wherein the portion of the shaft retractor a that is pressed radially inwardly to unlock the shaft retractor is biased radially outwardly toward a position where the shaft retractor is attached to the handle.

6. The system of claim 1, wherein the portion of the shaft retractor that is pressed radially inwardly to unlock the shaft retractor comprises two opposing parts that are pressed radially inwardly toward each other to unlock the shaft retractor from the handle.

7. The system of claim 1, wherein a distal end of the sheath flares radially outwardly.

8. The system of claim 7, wherein the distal end of the sheath can radially expand to accommodate a partially radial expanded prosthetic heart valve.

9. The system of claim 1, further comprising the prosthetic heart valve mounted on the inner shaft within the sheath.

10. A prosthetic heart valve delivery system, comprising:
a main shaft comprising a sheath;
a nose cone shaft that extends axially through the main shaft, wherein the nose cone shaft supports a radially collapsible prosthetic heart valve, and the sheath is configured to cover and uncover the prosthetic heart valve mounted on the nose cone shaft;
a nose cone attached to a distal end of the nose cone shaft, the nose cone shaft and the nose cone having a guidewire lumen extending therethrough;
a handle assembly comprising:
a main housing;
a sheath actuator operatively coupled to a proximal portion of the main shaft, and
an end portion positioned proximal to the sheath actuator and fixedly coupled to a proximal end of the nose cone shaft such that axial motion of the end portion effects corresponding axial motion of the nose cone shaft, the proximal end portion of the handle assembly being coupled to a proximal portion of the main housing such that the end portion has a locked position relative to the main housing and an unlocked position where the end portion is disengaged from the main housing and is movable axially relative to the main housing, and wherein the end portion comprises a part that is pressed inwardly to unlock the end portion from the main housing;

wherein the sheath actuator is operable move the sheath axially relative to the nose cone shaft, wherein proximal movement of the sheath relative to the nose cone shaft causes the sheath to uncover the prosthetic heart valve mounted on the nose cone shaft to allow the prosthetic heart valve to radially expand; and wherein the end portion of the handle assembly is operable to retract the nose cone proximally relative to the sheath when the end portion is unlocked from the main housing and moved proximally relative to the main housing.

11. The system of claim 10, wherein the end portion of the handle assembly is operable to retract the nose cone proximally through the prosthetic heart valve after the prosthetic heart is uncovered by the sheath and allowed to radially expand.

12. The system of claim 10, wherein the end portion of the handle assembly is operable to translate the nose cone shaft through the main housing when the end portion is unlocked from the main housing.

13. The system of claim 10, wherein the end portion of the handle assembly is manually translatable relative to the main housing when the end portion is unlocked from the main housing.

14. The system of claim 10, wherein the part of the end portion of the handle assembly that is pressed inwardly to unlock the end portion from the main housing is biased outwardly toward a position where the end portion is attached to the main housing.

15. The system of claim 10, wherein the part of the end portion of the handle assembly that is pressed inwardly to unlock the end portion from the main housing comprises two opposing portions that are pressed radially inwardly toward each other to unlock the end portion from the main housing.

16. The system of claim 10, wherein a distal end of the sheath flares radially outwardly.

17. The system of claim 16, wherein the distal end of the sheath can radially expand to accommodate a partially radial expanded prosthetic heart valve.

18. The system of claim 10, further comprising the prosthetic heart valve mounted on the nose cone shaft within the sheath.

\* \* \* \* \*